United States Patent
Farrington et al.

(10) Patent No.: US 6,294,366 B1
(45) Date of Patent: Sep. 25, 2001

(54) COMPOSITIONS AND METHODS FOR TREATING CELLULOSE CONTAINING FABRICS USING TRUNCATED CELLULASE ENZYME COMPOSITIONS

(75) Inventors: Graham K. Farrington, Acton; Paige Anderson, Medford, both of MA (US); Peter Bergquist, Chatswood (AU); Roy Daniels, Hamilton (NZ); Moreland David Gibbs, Lane Cove (AU); Hugh Morgan, Hamilton (NZ); Diane P. Williams, Hopkinton, MA (US)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 09/136,574

(22) Filed: Aug. 19, 1998

Related U.S. Application Data

(63) Continuation-in-part of application No. 08/932,571, filed on Sep. 19, 1997, now abandoned.

(51) Int. Cl.[7] .................................................. C12N 9/42
(52) U.S. Cl. .............................................................. 435/209
(58) Field of Search ............................................... 435/209

(56) References Cited

U.S. PATENT DOCUMENTS

| | | | |
|---|---|---|---|
| 4,832,864 | 5/1989 | Olson | 252/174.1 |
| 4,912,056 | 3/1990 | Olson | 435/263 |
| 5,122,159 | 6/1992 | Olson | 8/401 |
| 5,213,581 | 5/1993 | Olson | 8/401 |

FOREIGN PATENT DOCUMENTS

| | | |
|---|---|---|
| WO 91/10732 | 7/1991 | (WO) . |
| WO 91/17243 | 11/1991 | (WO) . |
| WO 92/06183 | 4/1992 | (WO) . |
| WO 92/17574 | 10/1992 | (WO) . |
| WO 94/29426 | 12/1994 | (WO) . |
| WO 96/23928 | 8/1996 | (WO) . |

OTHER PUBLICATIONS

Jauris, S., et al. Mol. Gen. Genet. 223: 258–267 (1990).

Henrissat B. (1991) A classification of glycosyl hydrolases based on amino acid sequence similarities. Biochem. J. 280:309–316.

Gibbs, M.D., D.J. Saul, E. Lüthi and P.L. Bergquist. The beta–mannanase from 'Caldocellum saccharolyticum' is part of a multidomain enzyme. Appl. Env. Microbiol., 58, 3864–3867 (1992).

C. R. Mackenzie and R. E. W. Williams, Can. J. Microbiol. 30, 1522 (1984).

Giorda, R., Ohmachi,T., Shaw, D.R. and Ennis, H.L. (1990) A shared internal threonine–glutamic acid–threonine–proline repeat defines a family of *Dictyostelium discoideum* spore germination specific proteins Biochemistry 29:7264–7269. Accession No. M33862.

Gilkes N. R., Henrissat B., Kilburn D. G., Miller M. C. and Warren R. A. J. (1991) Domains in microbial beta–1,4–glycanases: Sequence conservation, function, and enzyme families. Microbiological Reviews 55:2303–2315.

Lao,G., Ghangas, G.S., Jung, E.D. and Wilson, D.B. (1991) DNA sequences of three beta–1,4–endoglucanase genes from *Thermomonospora fusca*. J. Bacteriol. 173:3397–3407. Accession No. M73322.

Meinke,A., Braun,C.J., Gilkes,N.R., Kilburn,D.G., Miller, R.C.Jr. and Warren,R.A. J. (1991) Unusual sequence organization in CenB, a inverting endoglucanase from *Cellulomonas fimi*. J. Bacteriol. 173:308–314. Accession No. M64644.

Matsudaria, P. (1987) Sequence from picomole quantities of proteins electroblotted onto polyvinydifluoride membranes, J . Biol. Chem. 262 10035–10038.

Messing, J. (1983) Methods in Enzymology 101 (partC); Recombinant DNA, 20–78. Wu, R., Grsssman, L., Moldave, K. (eds) Academic Press, New York.

Morris, D., R. A. Reeves, M. D. Gibbs, D. S. Saul and P. L. Bergquist (1995). Correction of the ce/C pseudogene from *Caldicellulosiruptor saccharolyticus* and the activity of the gene product on kraft pulp. Appl. Environ. Microbiol. 61, 2262–2269 (1995).

Rainey F., Ward N., Morgan H., Toalster R. and Stackebrandt E. (1993). Phylogenetic analysis of anaerobic thermophilic bacteria: Aid for their reclassification. J. Bact. 175:4772–4779.

Sakka K., Yoshikawa K., Kojima Y., Karita S., Ohmiya K. and Shimada K. (1993). Nucleotide sequence of the *Clostridium stercorarium* xylA gene encoding a bifunctional protein with beta–xylosidase and alpha–L–arabinofuranosidase activities, and properties of the translated product. Biosci. Biotech. Biochem. 57:268–272.

Sambrook J., Fritsch E. F. and Maniatis T. (1989). Molecular cloning: A laboratory manual. Cold Spring Harbor Laboratory Press, New York, U.S.A.

(List continued on next page.)

*Primary Examiner*—Jon P. Weber
(74) *Attorney, Agent, or Firm*—Hesna J. Pfeiffer; Scott E Hanf

(57) ABSTRACT

Alkalophilic and thermophilic cellulases having high stability to elevated temperatures and pH have been isolated from an organism of unknown species, which most closely resembles those in the Caldicellulosiruptor genus and which has been called by us, Tok7B.1, These cellulases have been cloned and expressed in a recombinant system, so that they can be produced in quantity. These are particularly useful in treating cellulosic materials including cotton-containing fabrics, as detergent additives, and in aqueous compositions. We also provide genomic DNA which can be used in recombinant expression vectors and expression systems to produce enhanced alkali and/or temperature stability properties in cellulases other than those specifically described.

1 Claim, 20 Drawing Sheets

OTHER PUBLICATIONS

Saul D. J., Williams L. C., Grayling R. A., Chamley L. W., Love D. R. and Bergquist P. L. (1990). celB, a gene coding for a bifunctional cellulase from the extreme thermophile "*Caldocellum saccharolyticum*". Appl. Environ. Microbiol. 56:3117–3124.

Studier, F.W. and Moffat, B. A. (1986) Use of a bacteriophage T7 RNA polymerase to direct selective high–level expression of cloned genes. J. Mol. Biol. 189:113–130.

Teather R. M. and Wood P. J. (1982) Use of Congo Red polysaccharide interaction in enumeration and characterization of cellulolytic bacteria from the bovine rumen. Appl. Environ. Microbiol. 43:777–780.

Teo V.S.J., Saul D.J., Bergquist P.L. (1995) cela, another gene coding for a multidomain cellulase from the extreme thermophile *Caldocellum saccharolyticum*. Appl. Microbiol. Biotechnol. 43:291–296. Accession No. L32742.

Tomme P., Warren, R. A. J. and Gilkes, N. R. (1995). Cellulose Hydrolysis by bacteria and fungi. Adv. Microbiol. Physiol. 37:1–81.

Tucker, M.L. and Milligan, S.B. (1991) Sequence analysis and comparison of avocado fruit and bean abscission cellulases. Plant Physiol. 95:928–933. Accession No. M57400.

Winterhalter C., Heinrich P., Candussio A., Wich G. and Liebl W. (1995) Identification of a novel cellulose–binding domain within the multidomain 120kDa xylanase XynA of the hyperthermophilic bacterium *Thermotoga maritima*. Mol. Microbiol. 15:431–444.

FIG. 1A.

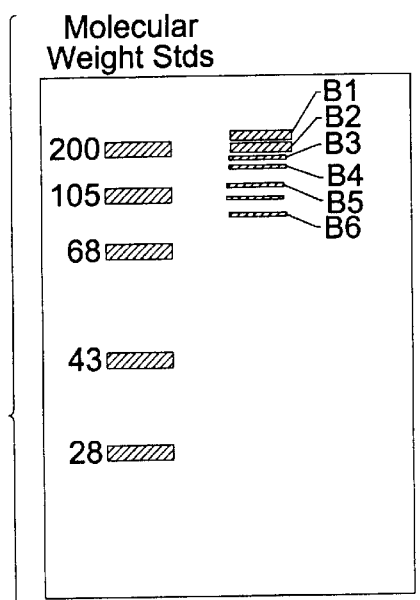

FIG. 1B.

N-terminal sequence found:

B1 AAYNYGEALQKAIMFYEFXM
B2 APDWSIPSLWESYKND
B3 AAYNYGEALQ
B4 APDWSIPSLW
B5 GAYNYGEALQ
B6 GAYNY

A) A composite diagram of protein bands that contained cellulase activity from the Tok7B.1 supernatant purified on either S-sepharose or Q sepharose. The protein bands were designated B1 through B6 each of the designated bands was N-terminally sequenced.

B) The N-terminal sequence found for each band is shown above. Two seperate N-terminal sequences were identified corresponding to the N-terminus of the Cel E and Cel B genes shown in Figure 3.

Blast sequence homology search with the identified N-terminal peptides shows the proteins have homology with Families 9 & 10 from Glycosyl hydrolases. Areas of homology between sequenced N-termini are shown in shaded boxes.

| Peptide No. | Amino-terminal amino acid sequence | Glycosyl Hydrolase Family based on amino acid homology comparisons |
|---|---|---|
| B1 | AAYNYGEALQKAIMFYEFXM | Glycosyl hydrolase Family 9 |
| B3 | AAYNYGEALQ | |
| B5 | GAYNYGEALQ | |
| B6 | GAYNY | |
| B2 | APDWSIPSLWESKYND | Glycosyl hydrolase Family 10 |
| B4 | APDWSIPSLW | |

FIG. 2.

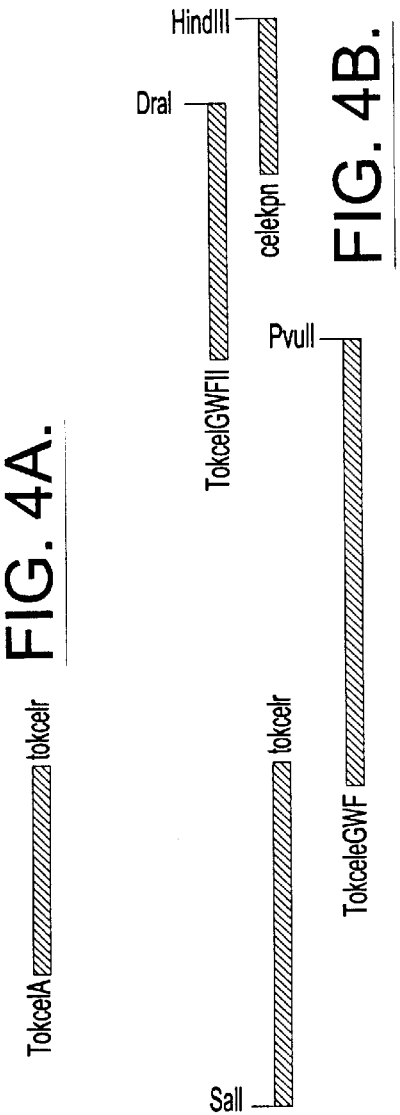
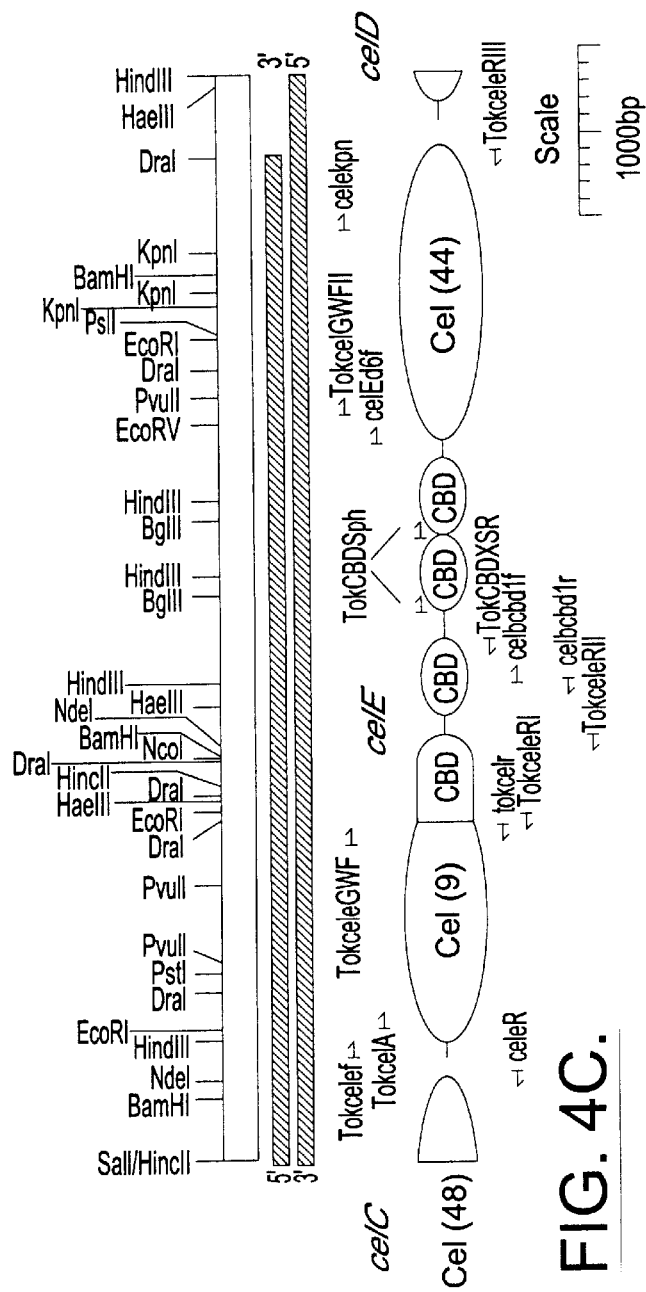
FIG. 4A.  FIG. 4B.  FIG. 4C.

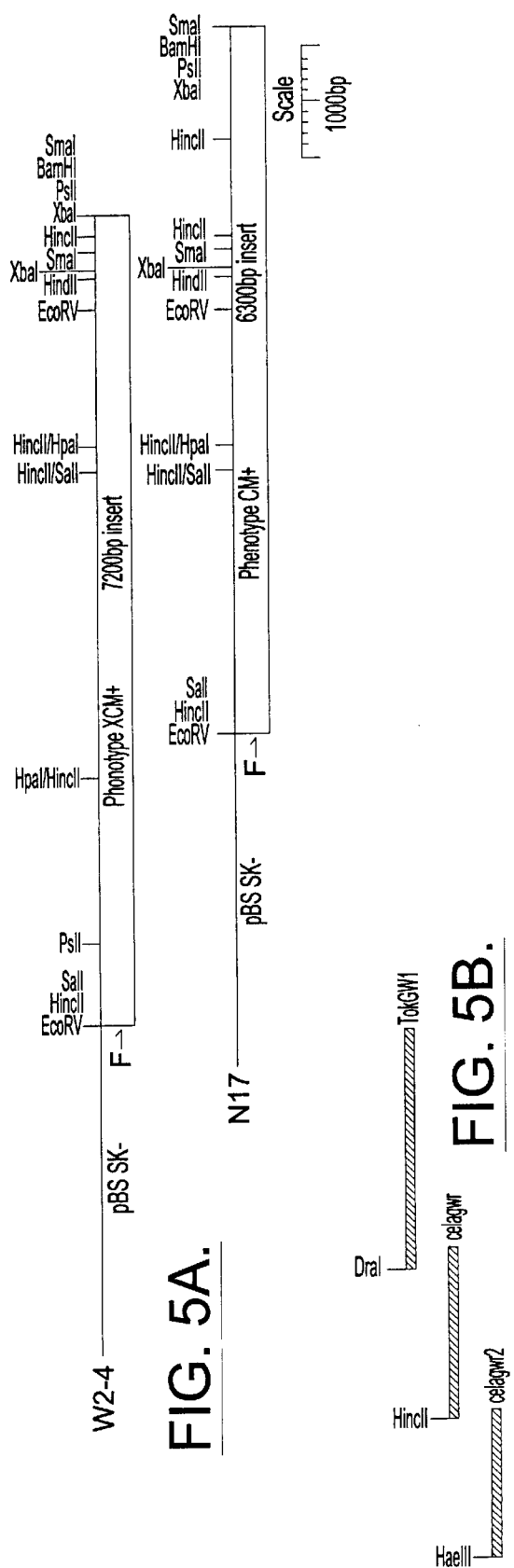
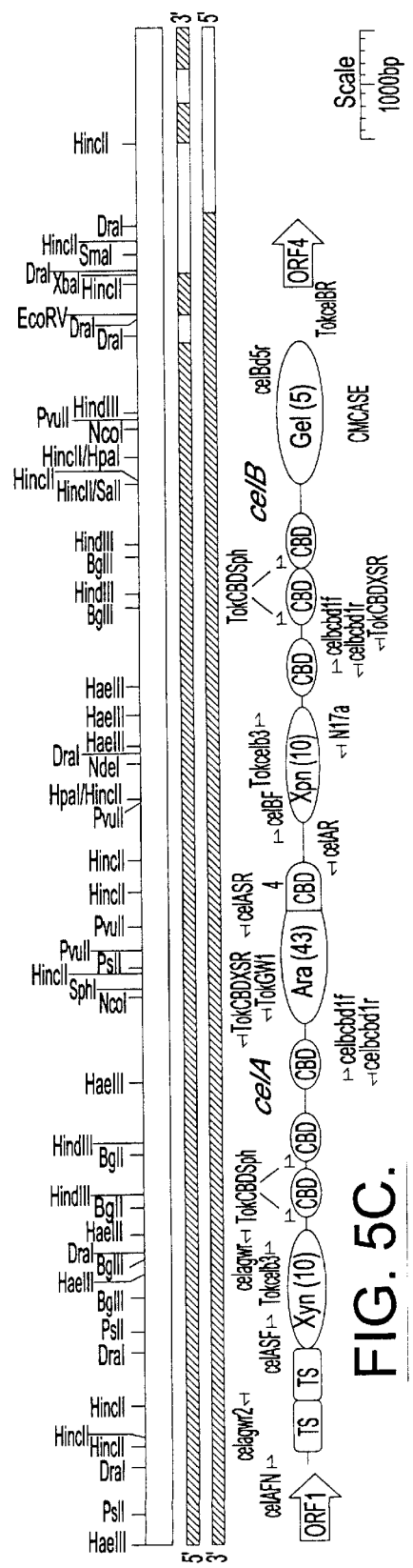
FIG. 5A.  FIG. 5B.  FIG. 5C.

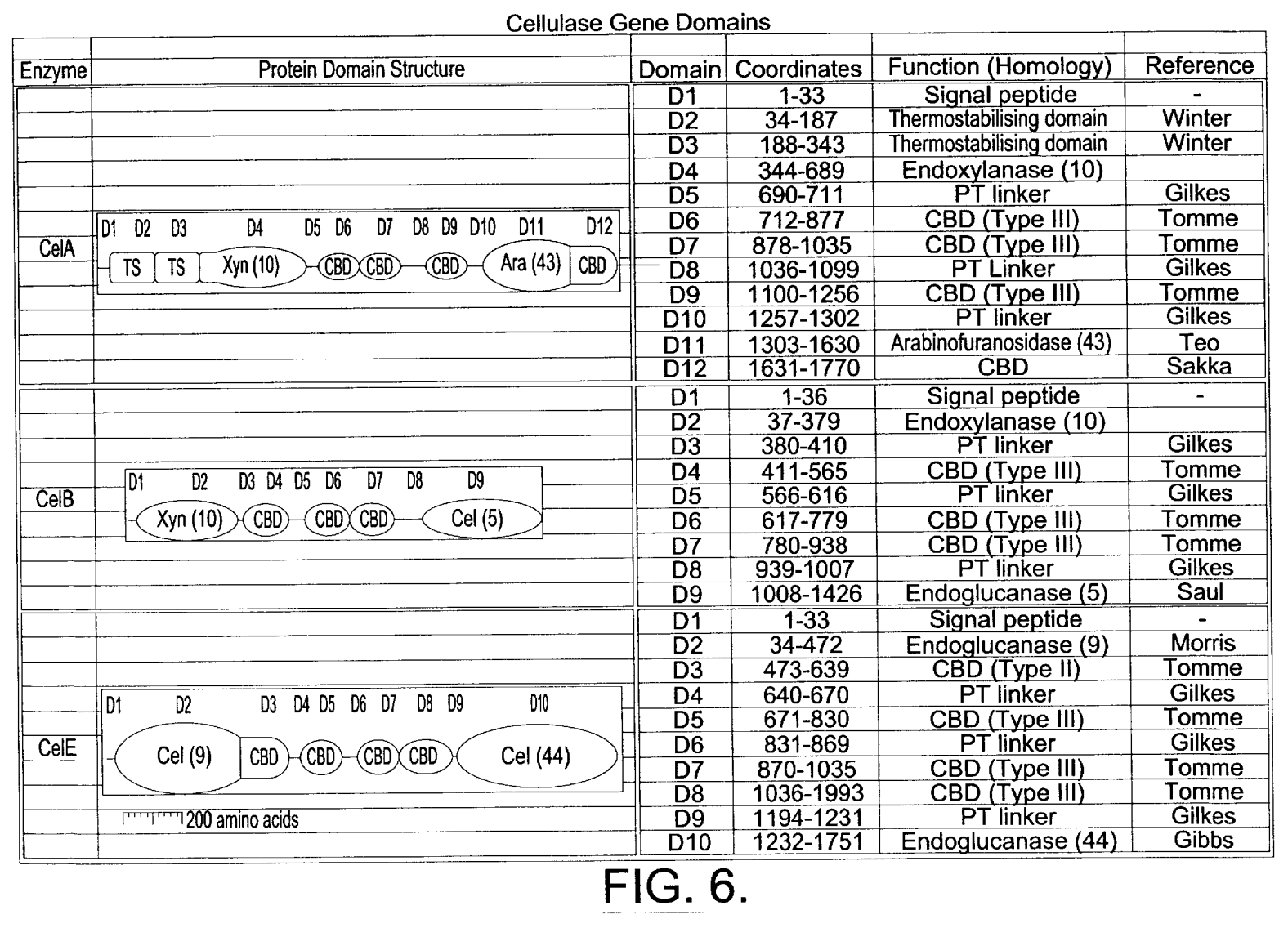

Cellulase Gene Domains

| Enzyme | Protein Domain Structure | Domain | Coordinates | Function (Homology) | Reference |
|---|---|---|---|---|---|
| CelA | | D1 | 1-33 | Signal peptide | - |
| | | D2 | 34-187 | Thermostabilising domain | Winter |
| | | D3 | 188-343 | Thermostabilising domain | Winter |
| | | D4 | 344-689 | Endoxylanase (10) | Gilkes |
| | | D5 | 690-711 | PT linker | Tomme |
| | | D6 | 712-877 | CBD (Type III) | Tomme |
| | | D7 | 878-1035 | CBD (Type III) | Tomme |
| | | D8 | 1036-1099 | PT Linker | Gilkes |
| | | D9 | 1100-1256 | CBD (Type III) | Tomme |
| | | D10 | 1257-1302 | PT linker | Gilkes |
| | | D11 | 1303-1630 | Arabinofuranosidase (43) | Teo |
| | | D12 | 1631-1770 | CBD | Sakka |
| CelB | | D1 | 1-36 | Signal peptide | - |
| | | D2 | 37-379 | Endoxylanase (10) | Gilkes |
| | | D3 | 380-410 | PT linker | Tomme |
| | | D4 | 411-565 | CBD (Type III) | Gilkes |
| | | D5 | 566-616 | PT linker | Tomme |
| | | D6 | 617-779 | CBD (Type III) | Tomme |
| | | D7 | 780-938 | CBD (Type III) | Tomme |
| | | D8 | 939-1007 | PT linker | Gilkes |
| | | D9 | 1008-1426 | Endoglucanase (5) | Saul |
| CelE | | D1 | 1-33 | Signal peptide | - |
| | | D2 | 34-472 | Endoglucanase (9) | Morris |
| | | D3 | 473-639 | CBD (Type II) | Tomme |
| | | D4 | 640-670 | PT linker | Gilkes |
| | | D5 | 671-830 | CBD (Type III) | Tomme |
| | | D6 | 831-869 | PT linker | Gilkes |
| | | D7 | 870-1035 | CBD (Type III) | Tomme |
| | | D8 | 1036-1993 | CBD (Type III) | Tomme |
| | | D9 | 1194-1231 | PT linker | Gilkes |
| | | D10 | 1232-1751 | Endoglucanase (44) | Gibbs |

FIG. 6.

FROM FIG. 7A.

Sequence Analysis of the Cloned Cellulases

| Cellulase Construct | N-terminal Sequence | | MALDI-TOF Analysis | |
|---|---|---|---|---|
| | Expected | Found | Expected | Found |
| E1 | AAYNYGEA | AAYNYGEA | | |
| E1/2 | | | 67,425 | 67,425 (a) 67,245 (b) |
| B4/5 | MKVWYANG | MKVWYANG (c) (X)PTPTPTP(T)I (d) | | |
| B5 | ATPSTPTPS | ATPSTPTPS | 48,991 | 48,691 (e) |

(a) N-terminal amino acids were changed from GT→AA in order to facilitate cloning of the protein and based on the found N-terminal sequence of the protein.
(b) N-terminal clipping of the two alanines would result in a 179 dalton decrease in the molecular weight of the protein.
(c) Sequences gave approximately equal picomolar quantities of signal.
(d) Internal cleavage site matching a site in the P-T linker region, (X) indicates that there was no amino acid was detected during the first cycle.
(e) C-terminal clipping of the the final two amino acids, lysine and asparagine, would give the correct molecular weight of 46,691.

FIG. 15.

Oligonucletotide primers designed and synthesized for PCR amplification, genomic walking, and sequenceing of cellulase genes from Tok7B.1.

| Primer Name | Seq # | Nucleotide Sequence | Length |
|---|---|---|---|
| avicelr | 21 | 5' - TGTATCCCATGCCGTCTT -3' | 18 |
| TokcelA | 22 | 5' - CAAAAAGCAATTATGTTTTATGAATT -3' | 26 |
| celagwr | 23 | 5' - TGGTGCTGGCAATGTTGAGTTGGC -3' | 24 |
| celagwr2 | 24 | 5' - TCGGTAGTGCCACTTTCAAATCCA -3' | 24 |
| celasf | 25 | 5' - CAAAGCAGACGAATCTGT -3' | 18 |
| celasr | 45 | 5' - GCGTGGTATGCAATATAC -3' | 18 |
| celbcbd1f | 26 | 5' - AGCTGAGCAGCGGAGTGA -3' | 18 |
| celbcbd1r | 27 | 5' - TCCACTCACTCCGCTGCT -3' | 18 |
| celbd5r | 28 | 5' - GTTCTGATACTGTCCAAG -3' | 18 |
| celekpn | 29 | 5' - ACAGGCGGCGTACAACAT -3' | 18 |
| celggwf | 30 | 5' - TTGAGGGATATGGTGACC -3' | 18 |
| celhgwf | 31 | 5' - GAGAAACATATCCTGCAA -3' | 18 |
| celhgwr | 32 | 5' - CCCATTTTATACCCAGGC -3' | 18 |
| celhgwr2 | 33 | 5' - TCTTGAGCAGCCATTGGA -3' | 18 |
| n17a | 34 | 5' - GATGGCCAGTTCACGTTTATATGG -3' | 24 |
| tokcelegwf | 35 | 5' - AGCACTGGTTGGTGGTCCTGGTAG -3' | 24 |
| tokcelgwfii | 36 | 5' - GATTGACGGGTTACAATTGGGAGAAC -3' | 26 |
| tokcelr | 37 | 5' - AGVGCACCNACAAATCCGGCATTGTARTC -3' | 29 |
| tokgw1 | 38 | 5' - CTCCAGAATGTCATTTGTAAGATACAT -3' | 27 |

TABLE I.

Oligonucleotide primers designed and synthesized for PCR amplification and directional cloning of cellulase genes from Tok7B.1. The sequence number for each primer is shown in column two.

| Primer Name | Seq # | Nucleotide Sequence/Engineered restriction sites (Reverse text) | Length | Target Gene | Restriction site | Orientation |
|---|---|---|---|---|---|---|
| celar | 3 | 5'- CCTTTATGAATTCATTTACTGACTGCTA-3' | 28 | celA | EcoRI | Reverse |
| celcr | 4 | 5'- CTTCCCTCGAGAATTCACACACCACTTTTG-3' | 31 | celC | XhoI, EcoRI | Reverse |
| celdr | 5 | 5'- TACCCTCGACAATTCCTATTTACTCATTA-3' | 30 | celG | XhoI, EcoRI | Reverse |
| celed6f | 6 | 5'- CTACACCCATCCTAACCCCGATGTTAA-3' | 28 | celE | NcoI | Forward |
| celff | 7 | 5'- AAATCTCCACTAAAAGTGAACAAGCA-3' | 27 | celF | XhoI | Forward |
| celgf | 8 | 5'- ATGTGTCCATGGCATTAATTATTTTGTTG-3' | 30 | celC | NcoI | Forward |
| tok7bcelef | 9 | 5'- ATGCAAGCCATCCAAGCAATTAAGAGGGTTG-3' | 31 | celE | SphI | Forward |
| tok7bceleri | 10 | 5'- TCAACAAAGATCTAATCATTTGTGGGTGTTC-3' | 32 | celE | BhlII | Reverse |
| tokcbdxsr | 11 | 5'- GTGCAGCTCGAGAAGCTCCCAGCTCCTGCCCCA-3' | 34 | celA-celH | XhoI, SacI | Reverse |
| tptcbdf | 12 | 5'- GAGGAACGTCATATGAAGGTATGGTATGCGAATGGGAA-3' | 39 | celA-celH | NdeI | Forward |
| tokcbdfsph | 13 | 5'- GAGGAGGACCATGCAGATCAAGGTATGGTATGCGAATG -3' | 38 | celA-celH | SphI | Forward |
| tokcelb3 | 14 | 5'- TTTACCATCCTGAGGAAATACAAAG -3' | 25 | celB-celF | SphI | Forward |
| tokcelbf | 15 | 5'- AGTTAGTGGATGGAAAAGAGAGTTTAAGG -3' | 31 | celB | SphI | Forward |
| tokcelbr | 16 | 5'- GAAGTATGGATCCATTTATTAATTCTTTGGG -3' | 31 | celB | BamHI | Reverse |
| tokceldf | 17 | 5'- TACAATTTTAGTCATGGTAACATACTTTTAG -3' | 35 | celD | NcoI | Forward |
| tokceler3 | 18 | 5'- GCAGCAGTCGACACTTTTTATTCTTAATCTAC -3' | 34 | celE | SalI | Reverse |
| tokcelerii | 19 | 5'- GTGGATGACATCTAACCCGGCTCTAAACCCCA -3' | 32 | celE | BhlII | Reverse |
| tokcelhf | 20 | 5'- TTGAACTTCCCCATCCCAGAATTTTACAAATTGG -3' | 35 | celH | NcoI | Forward |
| tokcbdf | 39 | 5'- GGGAATTCCATATGCGGCGTATAATTACGGTGAG -3' | 35 | celE | NdeI | Forward |
| tokcelecf | 41 | 5'- CCAGAGTATCACAGACAC -3' | 18 | celE | none | Forward |
| tokcelebamr | 42 | 5'- CCTGGATCGCTACGCTCCTCCCGGCTC -3' | 27 | celE | BamHI | Reverse |
| tokcel | 40 | 5'- TATTATTATCATATGCGG -3' | 15 | celE | NdeI | Reverse |

TABLE II.

Gene constructs expressed in E. coli by a T-7 promoter.

| Gene (1) | Gene Seq ID # | Protein (2) Designation | Domains Expressed | Amino Acids | Protein Seq ID # | Genetic Domains |
|---|---|---|---|---|---|---|
| celE | 2 | CelE1 | | MAAY39-D481 (3) | 44 | D2 |
| celE | 2 | CelE1/2 | | MAAY39-G635 (3) | 44 | D2/3 |
| celE | 2 | CelE1/2/3 | | MAAY39-G812 (3) | 44 | D2/3/4/5 |
| celB | 1 | CelB4/5 | | MK635-N426 (4) | 43 | D7/8/9 |
| celB | 1 | CelB5 | | A1001-P424 | 43 | D9 |

(1) Gene from which the clone was originally isolated.
(2) Designations of the expressed proteins.
(3) The MAA amino acids contained in the expressed proteins. The single amino acid designations reflect changes in the amino acid sequence resulting from incorporation of a NdeI restriction site at the start of the sequence.
(4) The M is preceeding the gene is a result of the addition of an AUG start codon for expression in E. coli.

TABLE III.

| Genes constructed | Protein Construct Purified | Thermal Stability °C (1) | pH rate profile (2) | Stonewash Effect |
|---|---|---|---|---|
| E1 | E1 | 55 | 5-9 | + |
| E1/2 | E1/2 | 80 | 4-11 | + |
| E1/2/3 | E1/2/3 | ND | 4-11 | - |
| B4/5 | B4/5 | 55 | 4-10 | - |
|  | B5 | 70 | 4-10 | + |

(1) Thermal Stability - the highest temperature at which the protein maintains 100% of it's activity for 45 minutes at pH 7.0.
(2) The protein maintains greater than or equal to 20% of it's maximum activity at 50° C.
ND = not determined

TABLE IV.

COMPOSITIONS AND METHODS FOR TREATING CELLULOSE CONTAINING FABRICS USING TRUNCATED CELLULASE ENZYME COMPOSITIONS

A. CROSS-REFERENCE TO RELATED APPLICATIONS

This application is a continuation-in-part application of application U.S. Ser. No. 08/932,571, filed Sep. 19, 1997, now abandoned.

B. FIELD OF THE INVENTION

The present invention is directed to improved methods for treating cellulosic materials, including cotton-containing fabrics and non-cotton containing cellulose fabrics with novel truncated cellulase enzymes. In addition, this invention relates to novel truncated cellulase enzymes which exhibit cellulase activity, DNA constructs encoding the enzymes, cellulolytic agents comprising the enzymes, and detergent and water purifying or conditioning compositions containing the enzymes. In particular, this invention provides thermophilic cellulases isolated from a thermophilic anaerobic bacterial strain found in New Zealand. The cellulase genes from this organism are identified and sequenced, and the cellulases expressed from this bacterium are shown to be particularly useful in the abrasion of denim, and in the manufacture of clothing having a "stone wash" look. Most importantly, the cellulases of this invention possess unexpected proteolytic and chemical stability, as well as thermal and pH stability in hot alkaline solutions, thereby rendering them important to as laundry detergent additives in many industrial and home washing applications.

C. BACKGROUND OF THE INVENTION

During or shortly after their manufacture, cotton-containing fabrics can be treated with cellulase enzymes in order to impart desirable properties to the fabric. For example, in the textile industry, cellulase has been used to improve the feel and/or appearance of cotton-containing fabrics, to remove surface fibers from cotton-containing knits, for imparting a stone washed appearance to cotton-containing denims and the like.

Clothing made from cellulose fabric, such as cotton denim, is stiff in texture due to the presence of sizing compositions used to ease manufacturing, handling and assembling of clothing items. It typically has a fresh dark dyed appearance. One desirable characteristic of indigo-dyed cloth is the alteration of dyed threads with white threads, which give denim a white on blue appearance.

After a period of extended wear and laundering, the clothing items, particularly denim, can develop in the clothing panels and on the seams, localized areas of variation in the form of a lightening, in the depth and density of color. In addition, a general fading of the clothes, some pucker in the seams and some wrinkling in the fabric panels can often appear. Additionally, after laundering, sizing is substantially removed from the fabric resulting in a softer feel. In recent years such a distressed or "stonewashed" look, particularly in denim clothing has become very desirable to a substantial proportion of the public.

Previous methods for producing the distressed look included stonewashing of a clothing item or items in a large tub with pumice stones having a particle size of about 1 by 1 inches and with smaller pumice particles generated by the abrasive nature of the process. Typically the clothing item is tumbled with the pumice while wet for a sufficient period such that the pumice abrades the fabric to produce in the fabric panels, localized abraded areas of lighter color and similar lightened areas in the seams. Additionally the pumice softens the fabric and produces a fuzzy surface similar to that produced by the extended wear and laundering of the fabric. This method also enhances the desired white on blue contrast described above.

The use of pumice stones has several disadvantages, including overload damage to the machine motors, mechanical damage to transport mechanisms and washing drums, environmental waste problems from the grit produced and high labor costs associated with the manual removal of the stones from the pockets of the garments.

In view of the problems associated with pumice stones in stonewashing, cellulase solutions are used as a replacement for the pumice stones under agitating and cascading conditions, i. e., in a rotary drum washing machine, to impart a "stonewashed" appearance to the denim.

Cellulases are enzymes which hydrolyze cellulose ($\beta$-1, 4-D-glucan linkages) and produce as primary products glucose, cellobiose, cello-oligosaccharides and the like. Cellulases are produced by a number of microorganisms and comprise several different enzyme classifications including those identified as exo-cellobiohydrolases (CBH), endoglucanases (EG), and $\beta$-glucosidases (BG). Enzymes within these classifications can be separated into individual components. The complete cellulase system comprising CBH, EG, and BG components synergistically act to convert crystalline cellulose to glucose.

A problem with the use of complete cellulase compositions from previously described microorganism sources for stonewashing dyed denim is the incomplete removal of colorant caused by redeposition or "backstaining" of some of the dye back onto the cloth during the stonewashing process. In the case of denim fabric, this causes recoloration of the blue threads and blue coloration of the white threads, resulting in less contrast between the blue and white threads and abrasion points (i.e., a blue on blue look rather than the preferred white on blue.)This redeposition is objectionable to some users.

Some cellulases are used commercially even though they result in backstaining because of their higher activity in denim material. Either high specific activity or a high level of purity results in a higher degree of abrasion in a significantly shorter processing time and therefore is preferable to commercial denim processors.

Attempts to reduce the amount of redeposition of dye included the addition of extra chemicals or enzymes, such as surfactants, proteases, or other agents, into the cellulase wash to help disperse the loosened dye. In addition, processors have used less active whole cellulase, along with extra washings. However this results in additional chemical costs and longer processing times. Finally the use of enzymes and stones together leave the processor with all the problems caused by the use of the stones alone. Accordingly, it would be desirable to find a method to prevent redeposition of colorant during stonewashing with cellulases.

There have been previous attempts to prevent backstaining. Patent WO 92/06221 of Genecor pertains to backstaining and indicates that the cellulose biohydralase (CBH) found in fungal cellulases is largely responsible for strength loss of the fabric and that a 5 to 1 ratio of endoglucanase to CBH is desirable. WO 96/23928, also to Genencor, relates to use of a truncated cellulase core enzyme. Both of these references emphasize the use of buffers to stabilize the cellulase solution in the wash environment. In the art it is recognized that cellulase activity is pH dependent. Most cellulases will exhibit cellulolytic activity within an acidic to neutral pH range, and the pH of an unbuffered cellulase solution could be outside the range required for cellulolytic activity. This can be undesirable and requires the addition of reagents to lower the pH of the denim following the wash cycle increasing the processing expense.

Applications of cellulases for textile processing and in commercial detergents demand proteins which are stable under highly alkaline conditions in the presence of surfactants as well as elevated temperatures.

D. BRIEF DESCRIPTION OF THE INVENTION

Microorganisms from New Zealand hot springs are a recognized potential source of alkalophilic and thermophilic enzymes. We have examined numerous of these microorganisms isolated from thermal pools for their cellulase activity under alkaline conditions. The approach used was to grow the isolated bacterial cultures on cotton in order to enrich for strains that contain cellulase activity. Selected strains were grown on a larger scale and culture supernatants were then individually screened for the desired stone-wash effect. A particular strain of unknown species, but most closely resembles those in the Caldicellulosiruptor genus and which has been called by us, Tok7B.1, was identified from this testing. Further investigation resulted in the discovery, in accord with this invention, of six different glycosidase containing genes, designated A through F, which were identified and sequenced. These genes, or gene fragments, were selected for cellulase activity, cloned and expressed. The expressed proteins, especially those designated E1, E1/2, B5, B4/5, and E3/B5 were purified and characterized. These enzymes were shown to have alkaline activity profiles with maximal activity near pH 8.0. These proteins were tested in the textile processing applications including stone washing, and anti-staining or anti-graying, as well as other applications using alkaline pH and/or elevated temperatures, and demonstrated excellent properties in these applications. These highly active cellulase proteins, the DNA encoding these cellulase genes, and recombinant production methods and means for such production of the highly active cellulases are all provided by the invention.

This invention demonstrates that intact gene products are not required or necessarily desirable for use in many textile processing applications, and that the stability and functionality of these proteins can be varied dramatically by selective combination different genetic fragments, thereby enhancing the activity of the novel proteins herein claimed. The stability enhancing gene fragments can also be expressed with other cellulase genes to confer the improved thermal or high alkaline stability on previously described cellulase proteins.

E. SUMMARY OF THE INVENTION

This invention describes thermophilic bacterial genes that encode multidomain genes containing combinations of cellulase, xylanase or cellobiohydralase activities. Truncated forms of these genes have demonstrated useful stonewash and detergent application activities with cotton cloth. Specific oligonucleotide sequences were identified that when used as PCR primers were shown to amplify genetic sequences that encode a series of protein domains containing glycohyrolase, thermal stabilizing and cellulose binding activities. A specific protein domain designated CelE2 was shown to function as a thermal stabilizing domain. The addition of this domain to an endoglucanase increased the thermostability by 25° C. This activity could be widely applicable for enhancing the thermal stability of other genes.

The genes were obtained from the thermophilic obligate anaerobic bacterium by PCR amplification of the genomic DNA. The synthetic oligonucleotide primer sequences used for the gene amplification reactions were based on either N-terminal protein sequence data, from which degenerate probes were designed, or from genomic expression library constructs that had been screened for cellulase, cellolobiosidase or xylanase activities. These specific oligonucleotide probes can serve to amplify genes useful in stone washing and/or detergent applications from other unknown bacteria that have cellulase genes.

Encoded gene fragments from the amplified genes identified as having cellulase activity were expressed in E. coli either singly or in combination with cellulose binding domains and/or thermal stabilizing domains. The expressed proteins were and purified to homogeneity and characterized. Cotton containing cloth treated with certain of these truncated gene constructs having endoglucanase domains and/or cellulose binding domains gave a stonewash appearance, and with other endoglucanase constructs a soil antiredeposition effect.

F. BRIEF DESCRIPTION OF DRAWINGS

FIGS. 1A and 1B are a composite drawing of protein bands containing cellulase activity purified from the supernatant broth of the Tok7B.1 organism, and their N-terminal sequences.

FIG. 2 shows the results of the BLAST sequence homology search with the sequenced protein N-termini.

FIGS. 4A and 4B show the genomic walking primers and the regions amplified to obtain the complete celE gene and flanking regions. FIG. 4C depicts a restriction map and the genetic domain structure of the celE gene sequence, including flanking upstream and downstream sequences.

FIG. 5A is a map of W2-4 and N-17 genomic DNA fragments isolated from the Tok7B.1 genome that express cellulase activity. FIG. 5B depicts the genomic walking primers and the regions amplified to obtain the complete celA and celB genes. The genetic domain structure and restriction map of celA and celB is shown in FIG. 5C.

FIG. 6 is a complete summary of the genetic domain structure of celA, celB and celE genes.

Figure 7A:
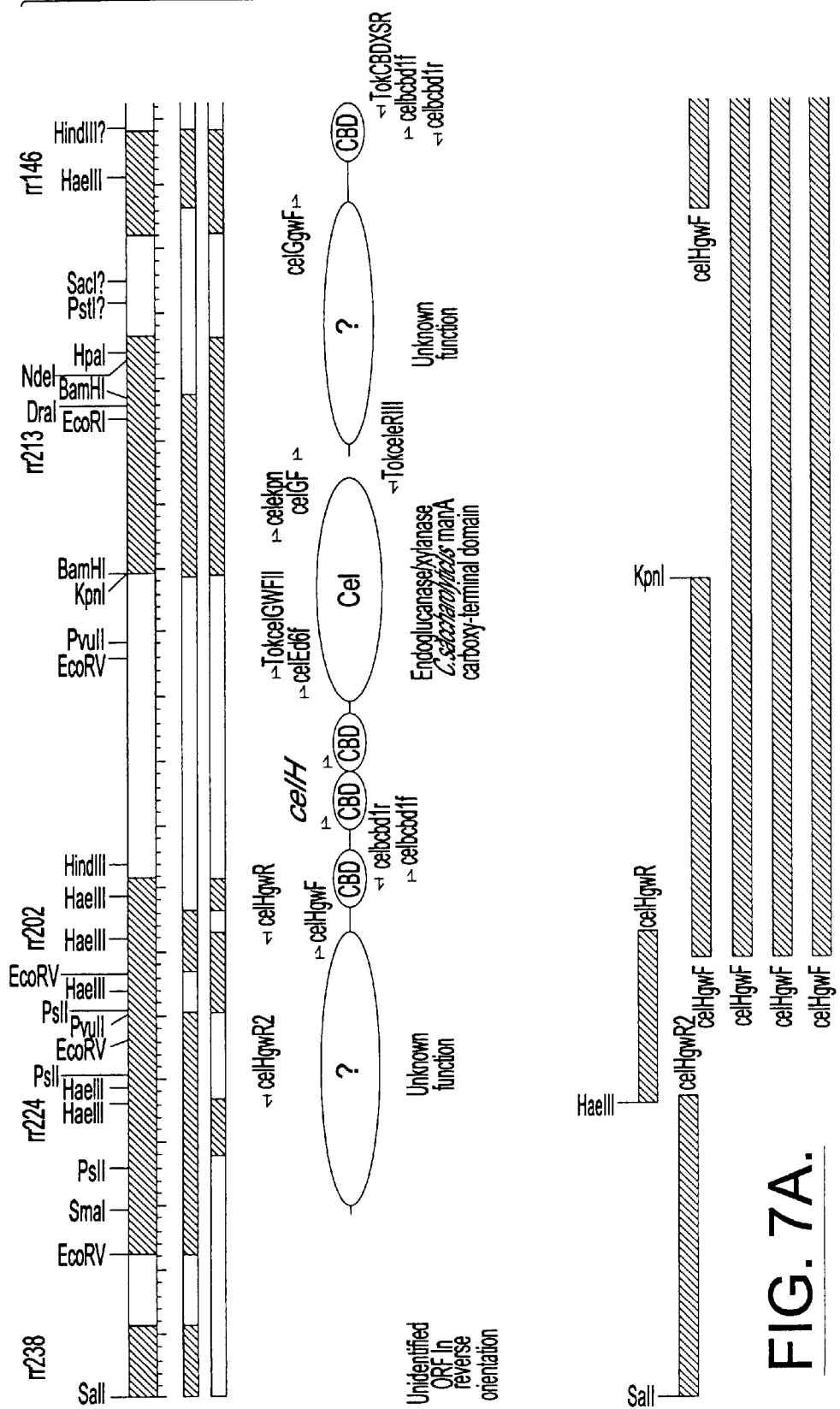
Figure 7B:
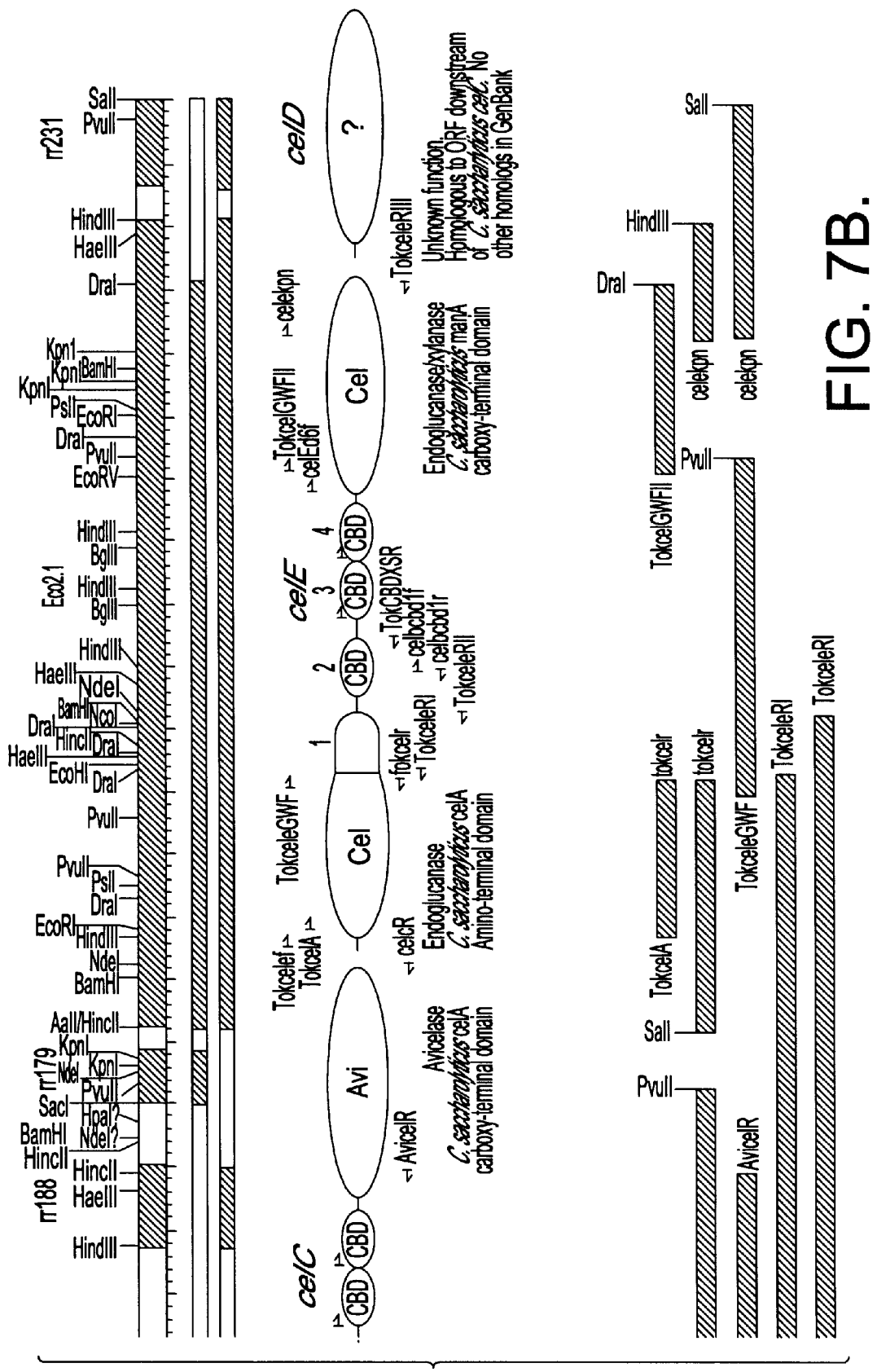
Figure 7C:
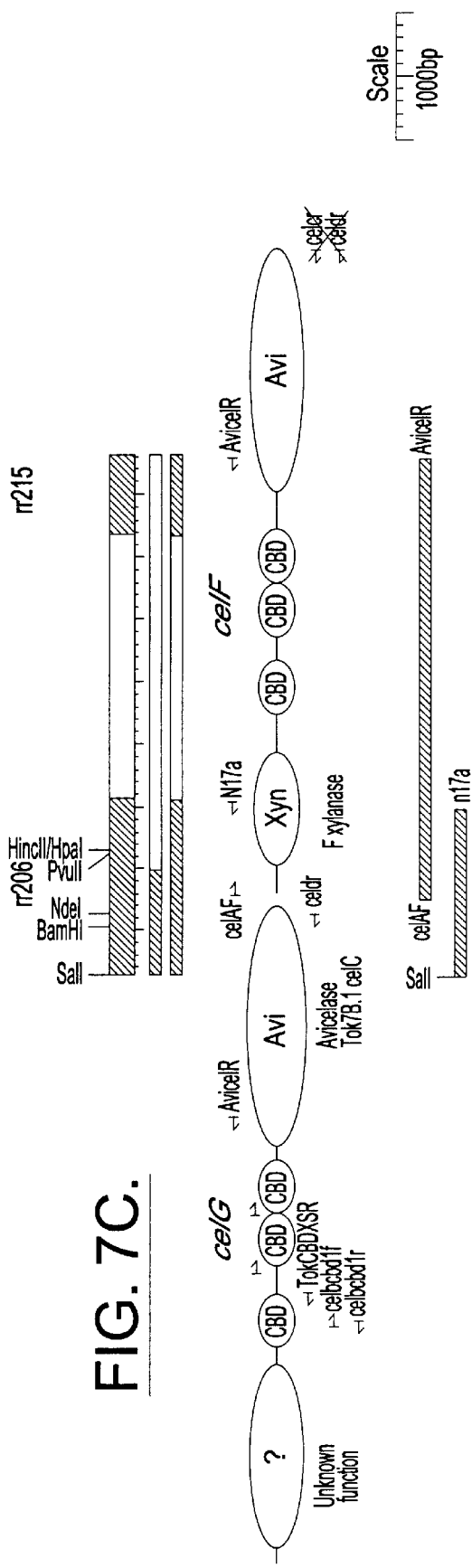

FIGS. 7a and 7b are a map of the restriction sites and domain structure of the Tok7B.1 genes celC, celD, celE, celF, celG and celH genes. Also the genomic walking primers used to amplify and identify each of these genes and the genetic regions amplified are indicated.

Figure 8:
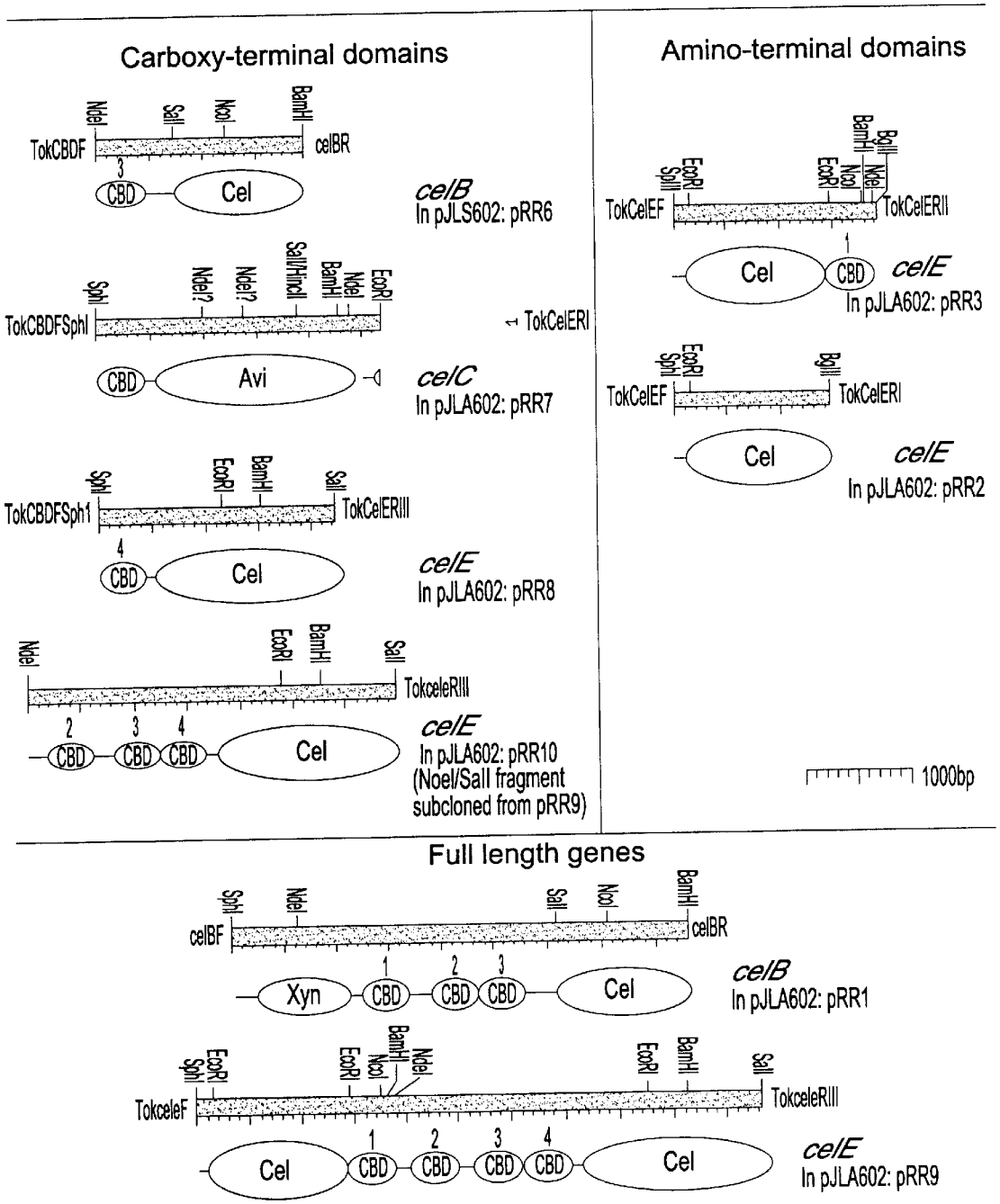

FIG. 8 is a diagram of the genes and gene fragments transferred into pJLA602 controlled expression plasmid vectors.

Figure 9:
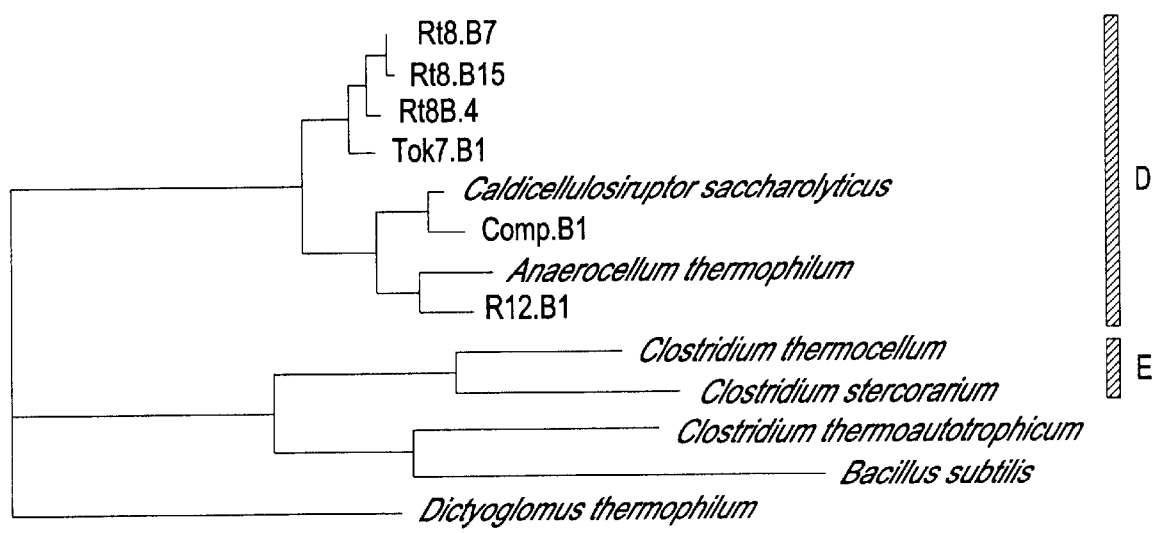

FIG. 9 is a phylogenetic analysis of the Tok7B.1 organism.

Figure 10:
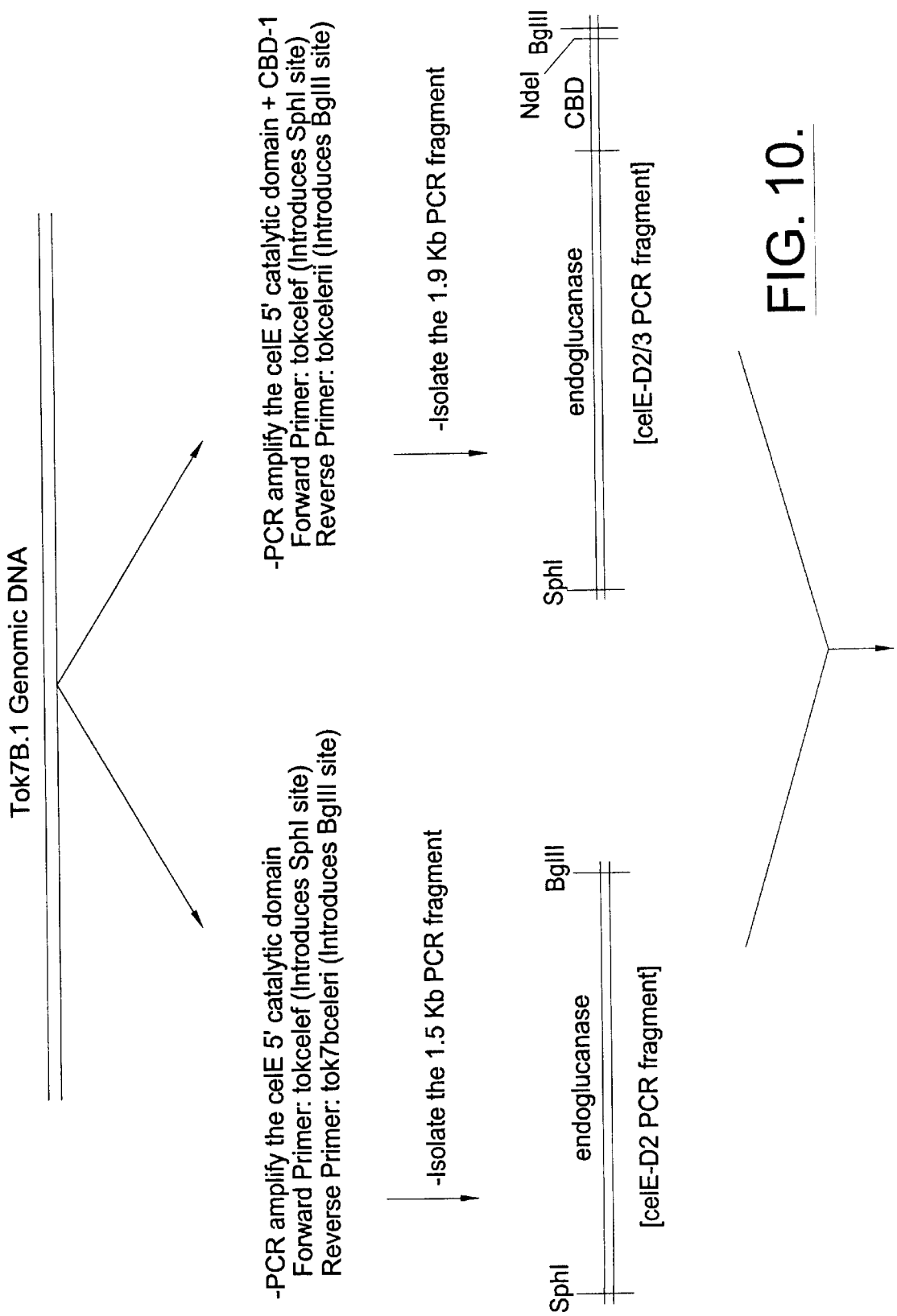
Figure 11:
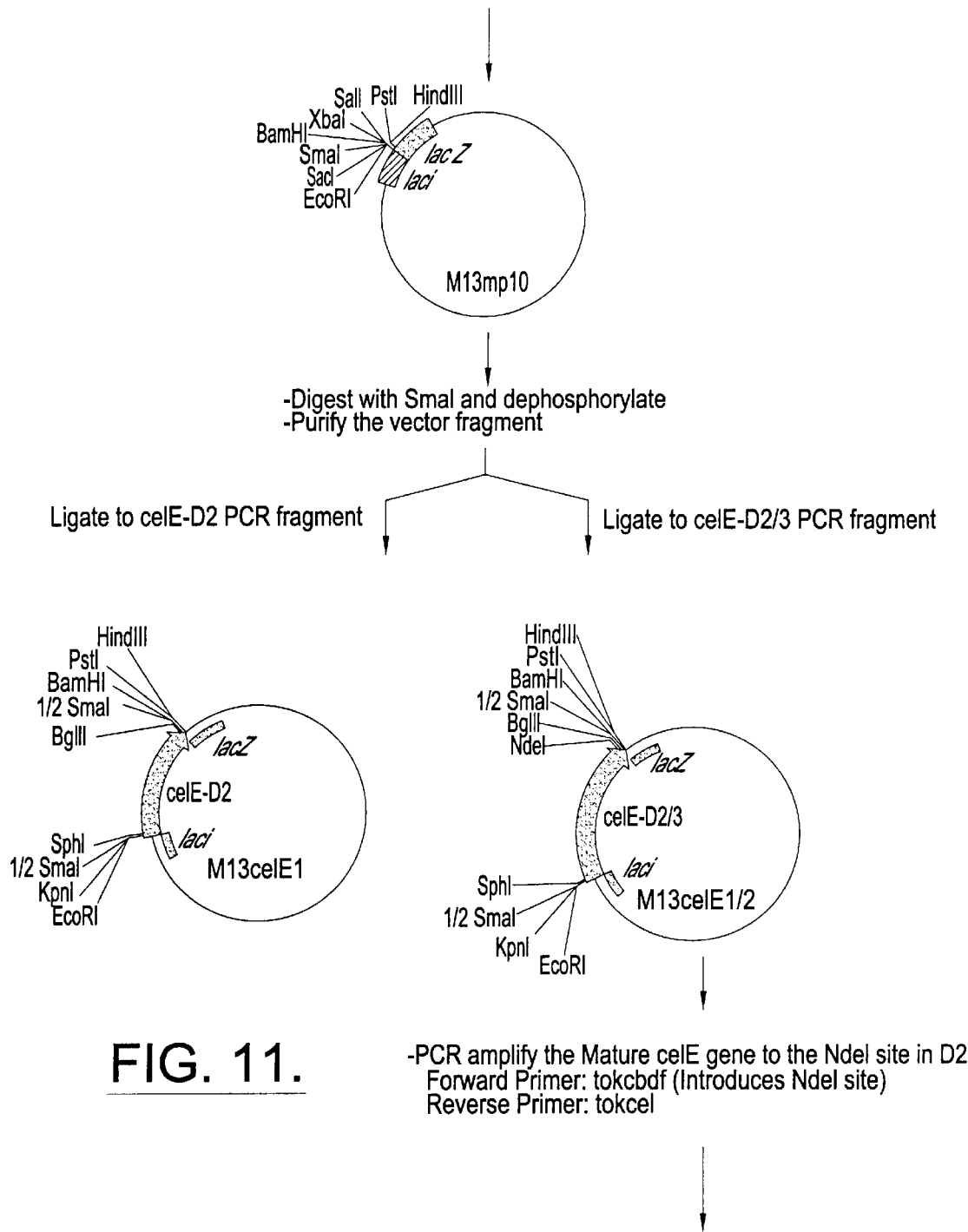
Figure 12:
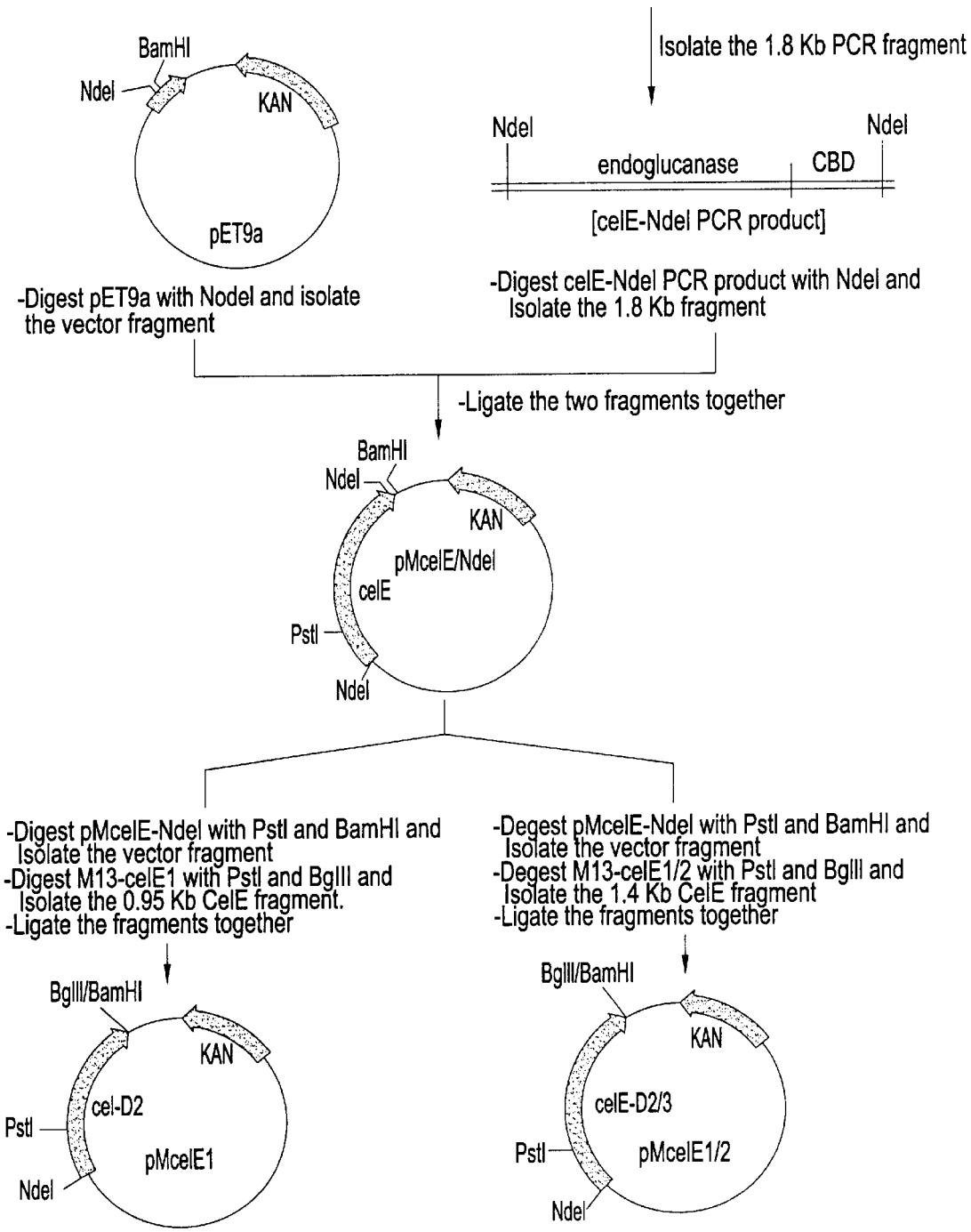

FIGS. 10–12 are flow diagrams for construction of the expression plasmids of pMcelE-1 and pMcelE1-2.

Figure 13:
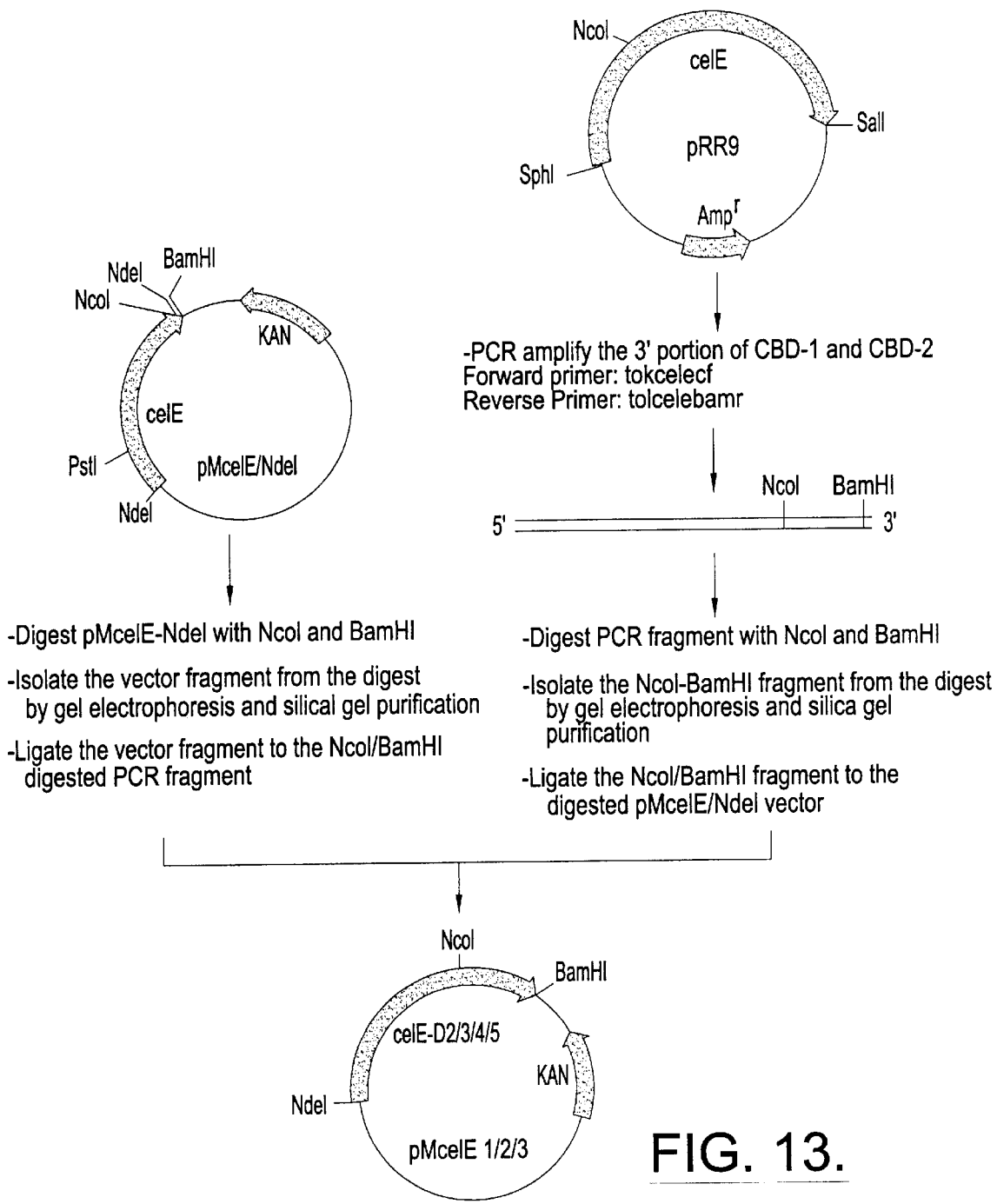

FIG. 13 is a flow diagram for construction of the expression plasmid pMcelE1-2-3.

Figure 14:
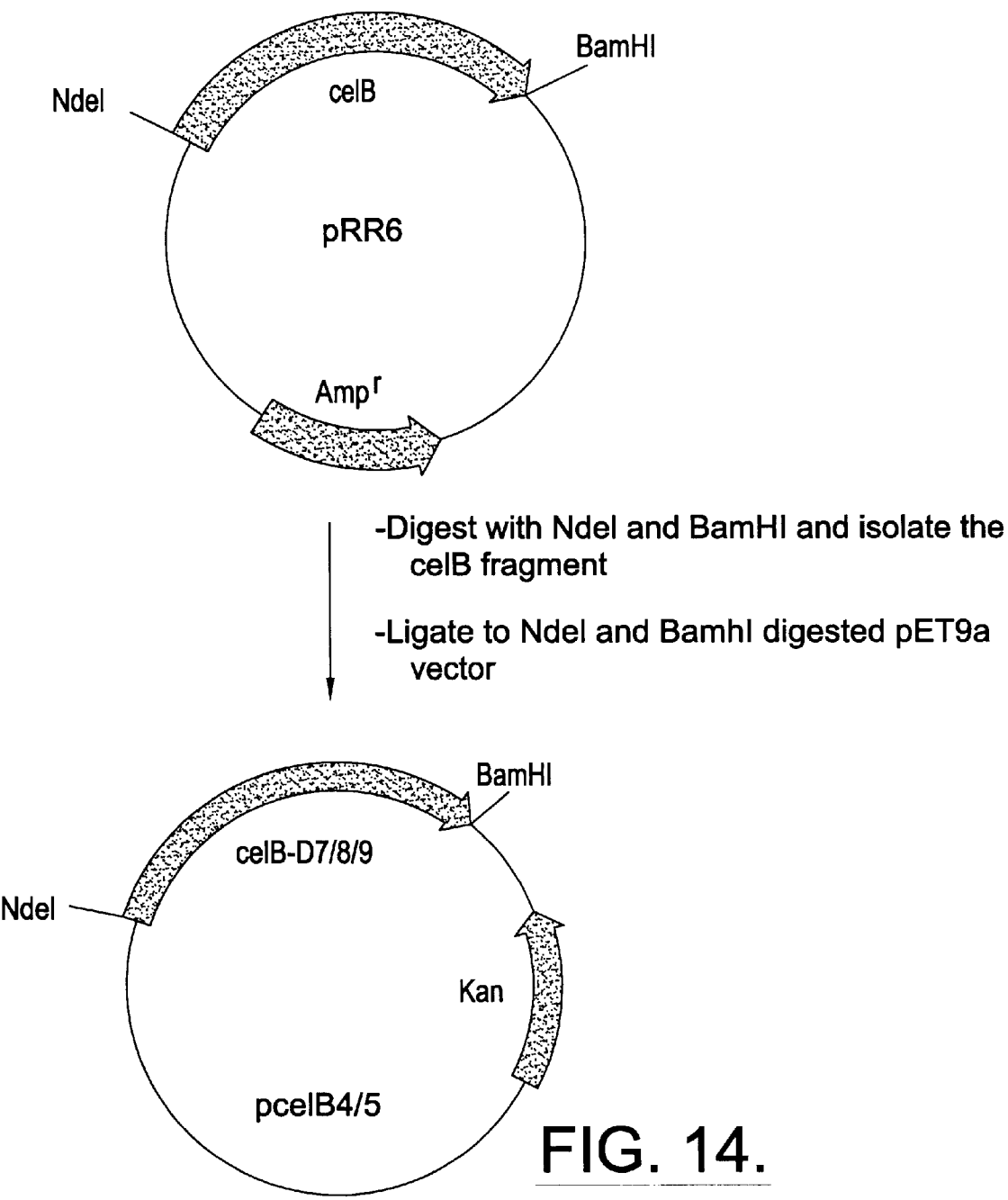

FIG. 14 is a flow diagram for construction of the expression plasmid of pcelB4-5.

FIG. 14A is a flow diagram for construction of the expression plasmid of pcelE3/B5.

FIG. 15 shows the sequence analysis and MALDI-TOF of the expressed cellulases.

TABLE I lists the oligonucleotide primers designed and synthesized for study of the cellulase genes in the Tok7B.1 organism.

TABLE II lists the oligonucleotides designed for PCR amplification and directional ligation of the Tok7B.1 genes into controlled expression vectors.

TABLE III shows the gene constructs expressed in *E. coli* by a T-7 promoter.

TABLE IV is a summary T-7 expressed cellulases, their pH rate profiles, thermal stabilities and effectiveness in the stonewash application.

G. DETAILED DESCRIPTION OF THE INVENTION

I. Definitions

"Cotton-containing fabric" means sewn or unsewn fabrics made of pure cotton or cotton blends including cotton woven fabrics, cotton knits, cotton denims, cotton yarns and the like. When cotton blends are employed, the amount of cotton in the fabric should be at least about 40 percent by weight cotton; preferably, more than about 60 percent by weight cotton; and most preferably, more than about 75 percent by weight cotton. When employed as blends, the companion material employed in the fabric can include one or more non-cotton fibers including synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramide fibers. "Cellulose containing fabric" means any cotton or noncotton containing cellulosic fabric or cotton or non-cotton containing cellulose blend including natural cellulosics and manmade cellulosics (such as Jute, flax, ramie, rayon, and the like). Included under the heading of manmade cellulose containing fabrics are regenerated fabrics that are well known in the art such as rayon. Other manmade cellulose containing fabrics include chemically modified cellulose fibers (e g., cellulose derivatized by acetate) and solvent-spun cellulose fibers (e.g. lyocell). Of course, included within the definition of cellulose containing fabric is any garment or yarn made of such materials. Similarly, "cellulose containing fabric" includes textile fibers made of such materials.

"Treating composition" means a composition comprising a truncated cellulase component which may be used in treating a cellulose containing fabric. Such treating includes, but is not limited to, stonewashing, modifying the texture, feel and/or appearance of cellulose containing fabrics or other techniques used during manufacturing of cellulose containing fabrics. Additionally, treating within the context of this invention contemplates the removal of "dead cotton", from cellulosic fabric or fibers, i.e. immature cotton which is significantly more amorphous than mature cotton. Dead cotton is known to cause uneven dyeing. Additionally, "treating composition" means a composition comprising a truncated cellulase component which may be used in washing of a soiled manufactured cellulose containing fabric. For example, truncated cellulase may be used in a detergent composition of, washing laundry. Detergent compositions useful in accordance with the present invention include special formulations such as pre-wash, pre-soak and home-use color restoration compositions. Treating compositions may be in the form of a concentrate which requires dilution or in the form of a dilute solution or form which can be applied directly to the cellulose containing fabric.

It is Applicants' present belief that the action pattern of cellulase upon cellulose containing fabrics does not differ significantly whether used as a stonewashing composition during manufacturing or during laundering of a soiled manufactured cellulose containing fabric. Thus, improved properties such as abrasion, redeposition of dye, strength loss and improved feel conferred by a certain cellulase or mixture of cellulases are obtained in both detergent and manufacturing processes incorporating cellulase. Of course, the formulations of specific compositions for the various textile applications of cellulase, e.g., stonewashing or laundry detergent or pre-soak, may differ due to the different applications to which the respective compositions are directed, as indicated herein. However, the improvements effected by the addition of cellulase compositions will be generally consistent through each of the various textile applications.

II. Preparation of Truncated Cellulase Enzymes

The present invention relates to the use of truncated cellulases and derivatives of truncated cellulases. These enzymes are preferably prepared by recombinant methods. Additionally, truncated cellulase proteins for use in the present invention may be obtained by other art recognized means such as chemical cleavage or proteolysis of complete cellulase protein.

The invention provides recombinant cellulase proteins which are alkalophilic and thermophilic and highly active and useful in washing applications, or in any applications including textile processing in which it is desirable to break down cellulose or cellulosic materials. It further provides DNA, free from its native genomic source, which encodes the recombinant cellulase active proteins in accord with the invention. In another preferred embodiment of this invention, we also provide genomic DNA which can be used in recombinant expression vectors and expression systems to produce enhanced alkali and/or temperature stability properties in cellulases other than those specifically described.

Also provided by the invention are bacteria cells capable of producing a native cellulase in accord with the invention and from which DNA encoding cellulases in accord with the invention may be obtained. Also provided is the native cellulase purified with respect to its native origins and associated native proteins such as by having a high protein purity or even absolute purity of at least 50%, e.g. 75%.

By way of specific preferred embodiments, this invention provides the following five particularly highly active cellulase proteins: E1, E1/2, B4/5, B5, and E3/B5.

E1 has an amino acid sequence of 446 amino acids extending from amino acid position No Y39 through amino acid position No D481 as given in Seq. ID No 44, or a function equivalent analogue thereof. DNA encoding this cellulase may vary in accord with the genetic code and a specific embodiment of such a DNA sequence comprises the DNA extending from nucleotide position No 748 through nucleotide position No 2076 as given in Sequence ID No 2.

E1/2 has an amino acid sequence of 600 amino acids extending from amino acid position No Y 39 through amino acid position No G635 as given in Seq. ID No 44, or a function equivalent analogue thereof. DNA encoding this cellulase may vary in accord with the genetic code and a specific embodiment of such a DNA sequence comprises the DNA extending from nucleotide position No 748 through nucleotide position No 2538 as given in Sequence ID No 2.

B4/5 has an amino acid sequence of 645 amino acids extending from amino acid position No K635 through amino acid position No N 1426 as given in Seq. ID No 43, or a function equivalent analogue thereof. DNA encoding this cellulase may vary in accord with the genetic code and a specific embodiment of such a DNA sequence comprises the DNA extending from nucleotide position No 8601 through nucleotide position No 10532 as given in Sequence ID No 1.

B/5 has an amino acid sequence of 418 amino acids extending from amino acid position No A 1001 through amino acid position No P 1424 as given in Seq. ID No 43, or a function equivalent analogue thereof. The B-5 protein can also end at K 1425 or N 1426, to include 419 or 420 amino acids, respectively. DNA encoding this cellulase may vary in accord with the genetic code and a specific embodiment of such a DNA sequence comprises the DNA extending from nucleotide position No 9255 through nucleotide position No 10526 as given in Sequence ID No 1.

E3/B5 has an amino acid sequence of 616 amino acids, and is a hybrid protein formed from sequences taken from the E and the B portions of the native sequences. The cel B sequence is that described from amino acid position No K635 through amino acid position No N 1426 as given in Seq. ID No 43. DNA encoding this hybrid cellulase may vary in accord with the genetic code, but a specific embodiment of such a DNA sequence comprises the DNA starting from the celE gene at G2659, ending at G3123, as given in Sequence ID No 2; then joined to a segment taken from the celB gene starting at G9153 and ending at A10,532., as given in Sequence ID No 1., or functional equivalent analogues thereof. This E3/B5 protein and its nucleotide sequence are described in Seq ID Nos 46 and 47 respectively.

As will be recognized by those skilled in the art, DNA encoding active cellulases in accord with the invention may be modified in various ways to produce such cellulases for practical usage. For example, the DNA encoding a signal sequence may be removed and replaced by the codon ATG encoding for Met at amino acid position No. 31, using known techniques. The resulting DNA which lacks a signal sequence may be used to express active cellulase in accord with the invention, more particularly in E coli, which cellulase product depending on the host strain will produce a cellulase with or without Met at its N-terminus, or mixtures of such products. Similarly, the signal sequence may be replaced by known techniques with other signal sequences to improve production, particularly secretion into the production media, and/or to adapt the DNA to particular hosts for production.

The cellulase gene-containing inserts cloned and provided in accord with our invention contain all the control or regulatory sequences necessary for expression of the structural gene in bacterial hosts, particularly Bacillus and E. coli hosts. These sequences, such as promoter sequences, ribosome binding site sequences and the like may also be modified or replaced in whole or in part by other control sequences using known techniques to improve production and/or to adapt the DNA to particular hosts for production. When such a change is made, the resulting DNA sequence is deemed to involve the structural gene in sequence with heterologous DNA.

The DNA encoding an active alkalophilic and thermophilic cellulase in accord with the invention may be incorporated into a wide variety of vectors for various purposes such as replication of such DNA or expression of the structural gene or for purposes of causing incorporation of the DNA into the genome of a host cell for ultimate expression of the encoded gene. Such vectors will typically involve DNA sequences containing the DNA encoding the active cellulase recombined with other heterologous DNA. The terms heterologous DNA and the like as used herein generally refer to a DNA sequence which has a functional purpose and which is either different from the sequences in or obtained from a source other than the native Tok7B.1 DNA from which the instant gene was cloned, thereby creating a continuous sequence which is not found or associated with the cellulase gene in the native Tok7B.1 source. Examples of such functional sequences are many and include for purposes of illustration origins of replications, genes for antibiotic resistance and also various control sequences, such promoter sequences to be used for effecting expression of the structural gene itself, as well as flanking sequences suitable for causing insertion of DNA containing the gene coding sequence into a host genome. Such vectors include for illustration only those commonly referred to plasmids and those which are viral vectors. The construction of vectors is well-known and DNA sequences of widely different origins and/or recombinations are available for such construction, such sequences also commonly called plasmids, viral vectors and the like. For example, a vector in accord with the invention and used by us can be obtained from the known plasmid pUC18 which contains the pBR 322-derived ampicillin resistance gene and origin of replication, together with a portion of the E. coli lacZ gene (lacZ') encoding the a-complementation peptide. This lacZ' fragment has been engineered to contain a multiple cloning site (MCS). DNA inserted into the MCS inactivates the lacZ' gene, providing blue/white color selection of recombinants when appropriate hosts and indicator plates are used. The complete gene or clone we obtained can be inserted or ligated into the MCS and expressed in an E. coli host by operation of its own native control sequences.

In general, the vectors of the invention are constructed with reference to suitability for incorporation into particular host cells, and such transformed cells are also a part of the invention. As used herein, the term "transformed" and the like means the incorporation of vector DNA into a host cell independent of the purpose in terms of replication of the recombinant gene or its expression, or both, and whether the vector DNA remains intact in the cell or its contained cellulase encoding gene is incorporated for expression into the cell genome. The vectors of the invention may be transformed into any of a variety of cell types such as bacterial cell, yeast cells, insect and mammalian cells. Preferably, the transformed cells are bacteria or yeast cells, and more preferably are gram negative bacteria such as E. coli or gram positive bacteria such as Streptomyces or Bacillus cells where such Bacillus cells are not of thermophilic source, such preferred Bacillus types including *Bacillus subtilis* and the like. Methods for transforming cells with vectors are generally well-known.

The invention also provides a process for producing the recombinant cellulase active proteins of the invention comprising culturing cells transformed with a recombinant expression vector of the invention comprising promoter DNA operatively controlling expression of the DNA encoding the cellulase protein. Methods of culturing such transformed cells to effect their multiplication and expression of the cellulase encoding gene of the transformed vector DNA are also well-known. Procedures for recovery of the recombinantly produced proteins are also known and may be used to obtain the cellulase of the invention in the more practical forms for use. In general, the recombinantly produced cellulase as expressed by the transformed cells may be retained within the cells and/or secreted into the culture media. When retained in quantity within the cells, the cells are lysed such as in a Waring Blender, sonifier or pressure cell to liberate the cellulase into the culture media which is then usually treated to separate cellular debris and preferably filtered to obtain the cellulase in the resulting aqueous supernatant or filtrate. When secreted into the media, the culture liquid media or supernatant containing the cellulase is simply separated from the cells. Such filtrates and supernatants may then be used as a basis for a product for treatment of cellulosic materials, typically after concentration. Such cellulase-containing liquids may also be treated, for example by microfiltration, to separate undesired materials including lower molecular weight proteins. The resulting aqueous cellulase-containing compositions may also be treated to enhance their storage or use properties, for example, by addition of buffers to enhance stability of the cellulase. Hence, the cellulase products may be buffered between pH 5 to 10, preferably pH 7 to 9, using, for example, Tris buffer.

The cellulases of the present invention have been found to be particularly useful for additives used in the cleaning or treatment of cellulose fabrics, including cotton-containing fabrics. They exhibit high activity even at high temperatures or high pH, thereby facilitating their suitability of aqueous detergent solutions and formulations.

It will be recognized that the cellulases of the invention are obtained from a microorganism characteristic of those which are thermophilic and alkalophilic and which produce a variety of enzymes which may be similarly classified by favoring conditions encountered in natural thermally heated alkaline pools. A variety of microorganisms have been identified in such pools. The cellulases of this invention originate from a particular strain of unknown species which most closely resembles those in the Caldicellulosiruptor genus and which has been called by us, Tok7B.1.

III Deposits

We have under the Budapest Treaty conditions, deposited with the Northern Regional Research Center (NRRL) at Peoria, Illinois, USA, a biologically pure culture of the cells indicated below, which deposits were assigned the Accession Numbers given below along with their date of deposit.

| Identification and Content of Deposit | Accession No. | Deposit Date |
| --- | --- | --- |
| 1) E. coli BL21 (DE3) Cel E | ATCC 98523 | August 29, 1997 |
| 2) E. coli DH αF' 1Q Cel B | ATCC 98524 | August 29, 1997 |
| 3) Tok7B.1 bacterial strain | ATCC 202028 | September 10, 1997 |

As will be recognized, any of the above deposits may be cultured under condition to cause expression of a cellulase of the invention in accord with the experiments described herein and such cellulase products recovered in a variety of product forms for use as also described herein. Alternatively, cultures of the deposited cells may be grown to multiple the number of copies of their contained plasmidal clones and the cellulase gene and coding sequence may be separated from the plasmids by the use of restriction enzymes, preferably by partial digest with Sau3Al, and the DNA encoding the cellulase (for example, an approx. 1.57 Kb fragment upon Sau3Al partially digest) used for a variety of purposes including production of active cellulase protein of the invention in a wide variety of other expression systems.

IV. Methods Of Treating Cellulose Containing Fabric Using Truncated Cellulase Enzymes As noted above, the present invention pertains to methods for treating cellulose containing fabrics with a truncated cellulase enzyme. The use of the truncated cellulase composition of this invention provides the novel and surprising result of effecting a relatively low level of dye redeposition while maintaining an equivalent level of abrasion compared to prior art cellulase treatment. Because the level of abrasion acts as an indicator of the quality and effectiveness a of particular cellulase treatment techniques, e.g., stonewashing or laundering, the use of the instant invention provides a surprisingly high quality textile treatment composition. In the laundering context, abrasion is sometimes referred to as color clarification, defuzzing or biopolishing.

The present invention specifically contemplates the use of truncated cellulase core, alone or in combination with additional cellulase components, to achieve excellent abrasion with reduced redeposition when compared to non-truncated cellulase. Additionally, naturally occurring cellulase enzymes which lack a binding domain are contemplated as within the scope of the invention. It is also contemplated that the methods of this invention will provide additional enhancements to treated cellulose containing fabric, including improvement in the feel and/or appearance of the fabric.

a. Methodology for Stonewashing With Truncated Cellulase Compositions

According to one aspect of the present invention, the truncated cellulase compositions described above may be employed as a stonewashing composition. Preferably, the stonewashing composition of the instant invention comprises an aqueous solution which contain a an effective amount of a truncated cellulase together with other optional ingredients including, for example, a buffer, a surfactant, and a scouring agent.

An effective amount of truncated cellulase enzyme composition is a concentration of truncated cellulase enzyme sufficient for its intended purpose. Thus an "effective amount" of truncated cellulase in the stonewashing composition according to the present invention is that amount which will provide the desired treatment, e.g., stonewashing. The amount of truncated cellulase employed is also dependent on the equipment employed, the process parameters employed (the temperature of the truncated cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of truncated cellulase can be readily determined by the skilled artisan based on the above factors as well as the desired result. Preferably the truncated cellulase composition is present in a concentration of from 1–1000 PPM, more preferably 10–400 PPM and most preferably 20–100 PPM total protein.

Optionally, a buffer is employed in the stonewashing composition such that the concentration of buffer is that which is sufficient to maintain the pH of the solution within the range wherein the employed truncated cellulase exhibits activity which, in turn, depends on the nature of the truncated cellulase employed. The exact concentration of buffer employed will depend on several factors which the skilled artisan can readily take into account. For example, in a preferred embodiment, the buffer as well as the buffer concentration are selected so as to maintain the pH of the final truncated cellulase solution within the pH range required for optimal cellulase activity. Preferably, buffer concentration in the stonewashing composition is about 0.001 N or greater. Suitable buffers include, for example, citrate and acetate.

In addition to truncated cellulase and a buffer, the stonewashing composition may optionally contain a surfactant. Preferably, the surfactant is present in a concentration in the diluted wash mediums of greater than 100 PPM, preferably from about 200–15,000 PPM. Suitable surfactants include any surfactant compatible with the cellulase and the fabric including, for example, anionic, non-ionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known in the art.

In a preferred embodiment, a concentrated stonewashing composition can be prepared for use in the methods described herein. Such concentrates would contain concentrated amounts of the truncated cellulase composition described above, buffer and surfactant, preferably in an aqueous solution. When so formulated, the stonewashing concentrate can readily be diluted with water so as to quickly and accurately prepare stonewashing compositions according to the present invention and having the requisite concentration of these additives.

Preferably, such concentrates will comprise from about 0.1 to about 50 weight percent of a cellulase composition described above (protein); from about 0.1 to about 80 weight percent buffer; from about 0 to about 50 weight percent surfactant, with the balance being water. When aqueous concentrates are formulated, these concentrates can be diluted so as to arrive at the requisite concentration of the components in the truncated cellulase solution as indicated above. As is readily apparent, such stonewashing concentrates will permit facile formulation of the truncated cellulase solutions as well as permit feasible transportation of the concentration to the location where it will be used. The stonewashing concentrate can be in any art recognized form, for example, liquid, emulsion, gel, or paste. Such forms are well known to the skilled artisan.

Other materials can also be used with or placed in the stonewashing composition of the present invention as desired, including stones, pumice, fillers, solvents, enzyme activators, and other anti-redeposition agents. The cellulose containing fabric is contacted with the stonewashing composition containing an effective amount of the truncated cellulase enzyme or derivative by intermingling the treating composition with the stonewashing composition, and thus bringing the truncated cellulase enzyme into proximity with the fabric. For example, if the treating composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor.

The cellulose containing fabric is incubated with the stonewashing solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature which allow the truncated cellulase enzyme to react efficiently with cellulose containing fabric. The reaction conditions for truncated cellulase core, and thus the conditions effective for the stonewashing compositions of the present invention, are substantially similar to well known methods used with corresponding non-truncated cellulases. Similarly, where a mixture of truncated and non-truncated cellulase is utilized, the conditions should be optimized similar to where a similar combination may have been used. Accordingly, it is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from 5:1 to about 20:1, and most preferably from about 10:1 to about 15:1. Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature which temperature is dependent on the nature of the cellulase used. Thus, if the reaction temperature is permitted to go too high, then the cellulolytic activity is lost as a result of the denaturing of the cellulase As a result, the maximum reaction temperatures employed herein are generally about 65° C. In view of the above, reaction temperatures are generally from about 30° C. to about 65° C.; preferably, from about 35° C. to about 60° C.; and more preferably, from about 35° C. to about 55° C.

Reaction times are dependent on the specific conditions under which the stonewashing occurs. For example, pH, temperature and concentration of truncated cellulase will all effect the optimal reaction time. Generally, reaction times are from about 5 minutes to about 5 hours, and preferably from about 10 minutes to about 3 hours and, more preferably, from about 20 minutes to about 1 hour.

Cellulose containing fabrics treated in the stonewashing methods described above using truncated cellulase compositions according to the present invention show reduced redeposition of dye as compared to the same cellulose containing fabrics treated in the same manner with an non-truncated cellulase composition.

b. Methodology for Treating Cellulose Containing Fabrics With A Detergent Composition Comprising Truncated Collulase Enzyme According to the present invention, the truncated cellulase composition described above may be employed in detergent compositions. The detergent compositions according to the present invention are useful as pre-wash compositions, pre-soak compositions, or for detergent cleaning during the regular wash cycle. Preferably, the detergent composition which can be dry mixed or in an aqueous liquid formulation, of the present invention comprises an effective amount of truncated cellulase, and a surfactant, and optionally include other ingredients and additives commonly employed in detergent formulations. An effective amount of truncated cellulase employed in the detergent compositions of this invention is an amount sufficient to impart improved anti-graying, anti-staining, anti-backstaining, or anti-soil deposition of cotton or cellulosic containing fabrics. Preferably, the truncated cellulase employed is in a concentration of about 0.001% to about 25%, more preferably, about 0.02% to about 10% by weight percent of detergent. The specific concentration of truncated cellulase enzyme employed in the detergent composition is preferably selected so that upon dilution into a wash medium, the concentration of truncated cellulase enzyme is in a range of about 0.1 to about 1000 PPM, preferably from about 0.2 PPM to about 500 PPM, and most preferably from about 0.5 PPM to about 250 PPM total protein. Thus, the specific amount of truncated cellulase enzyme employed in the detergent composition will depend on the extent to which the detergent will be diluted upon addition to water so as to form a wash solution. At lower concentrations of truncated cellulase enzyme, i.e., concentrations of truncated enzyme lower than 20 PPM, the decreased backstaining or redeposition with equivalent surface fiber abrasion when compared to prior art compositions will become evident after repeated washings. At higher concentrations, i.e., concentrations of truncated cellulase enzymes of greater than 40 PPM, the decreased backstaining with equivalent surface fiber removal will become evident after a single wash. This invention is illustrated by the following procedures and examples.

Applications of cellulases for textile processing and in commercial detergents demand proteins that are stable under conditions of alkaline pH and elevated temperatures.

V. EXAMPLES

Isolation of Cellulase Secreting Microorganisms from Alkaline Thermal Pools To identify thermal stable glycolytic proteins, microorganisms were isolated from the water and sediment samples taken from geothermal pools in the central volcanic region of New Zealand's North Island. The criteria for the pools sampled were temperatures of at least 50° C. and pH values of greater than 6.0. A total of twenty samples were collected from geothermal pools that met the criteria. Each of the samples contained a complex mixture of microorganisms. In order to enrich the samples for microorganisms that expressed cellulase genes with desired cellulase activity 1 mL volumes of the collected sample were inoculated into 10 mL of 2/1 medium in Hungate tubes containing either amorphous cellulose (7 g/L) or unbleached cotton fabric (approximately 1 cm square) as cellulose substrate, at pH 7.0 and pH 8.5. These tubes were incubated at 70° C. and the cultures viewed microscopically after 4 days. The enrichment strategy was based on the assumption that the presence of the cellulosic fibers would induce expression of the cellulase genes in the microorganisms, and that those microorganisms would flourish under these conditions. From this collection of organisms the anaerobic, cellulase producer, Tok7B.1 was isolated from a water/sediment sample take from Tokaanu Pool 7, situated in the central volcanic region of the North Island, New Zealand. The pH and temperature of this particular pool at the time of sampling were pH 7.5 and 60° C., respectively.

The 2/l medium and amorphous cellulose, pH 7.0 proved the most favorable for the growth of the anaerobic rods from the Tok7B. 1 sample, and after further subculturing, PAHBAH (p-hydroxybenzoic acid hydrazide) assays (Lever, 1973) on the concentrated supernatant confirmed the presence of cellulase-producing organisms. The substrate for these PAHBAH assays was 0.2% carboxymethyl cellulose (low viscosity) in 100 mM Taps buffer pH 8.8 at 20° C.

A pure culture of Tok7B.1 was obtained using a version of the Roll Tube method described by Hungate (1969). Serial dilutions of the positive cultures were make in Hungate tubes containing the growth medium +18 g/l agar. The agar/culture mixture was solidified around the inside of the sealed tube by rolling in a flat dish containing iced water. Tubes were incubated at 70° C. and single colonies removed aseptically using a Pasteur pipette with the tip bent a right angles. A plug of agar was placed in liquid medium and the cells released by crushing against the side of the tube. Positive identification of a cellulase producer was again confirmed by PAHBAH assays of the culture supernatants. To detect secreted cellulases supernatants from the cultures were concentrated approximately ten fold prior to being assayed for cellulase activity using CMCase assay.

The Tok7B.1 cellulases were identified in a secondary screening assay that served to evaluate the biostone washing effectiveness of the cellulases secreted into the sample supernatant. Each of the cultures selected for screening was fermented in sufficient quantity and the supernatants concentrated in order to provide sufficient activity for the biostone wash testing, approximately 10,000 CMCase units. The supernatants were tested in a 2L drum denim assay at equivalent levels of CMCase activity. The cellulases were tested under the following conditions; pH 7.0 for 60 minutes at 50° C. using 135 g of blue denim samples were washed for 1 h at pH 7.0. The light reflectance value on the blue denim cloth and from a swatch of white cloth included in the wash were determined by measuring the level of denim abrasion and backstaining, respectively. Blue denim samples that demonstrated a reflectance value of above 15 and a dose dependent effect with increasing concentrations of fermentation supernatants were considered to contain candidate cellulases. White cloth swatches that have a reflectance of below 4 were acceptable for backstaining. Based on these tests the Tok7B.1 organism was found to produce the most effective cellulases, giving the highest abrasion with the lowest backstaining of the samples tested.

Strategy for Identifying Industrially Useful Cellulases

Our strategy was to identify industrially useful cellulases secreted from the Tok7B.1 organism, then to identify the individual genes responsible for that activity. The following steps were carried out to clone the individual genes, express these genes in an intermediary expression system and test the individual cellulases in the application. The first step in the strategy was to identify the individual proteins secreted by the Tok7B.1 bacterium. Identification of the individual cellulases secreted by the bacterium was important because identification of the genes effective in the application would limit the number of cellulase genes and gene constructs that would have to be expressed and tested.

Cellulase Nomenclature

Genes and genetic constructs are designated in small letters and are italicized, for example the genes that encode the CelE proteins are designated celE. Conversely proteins are designated by capitalizing the first letter and are not italicized, for example, CelE1. The Tok7B.1 cellulase genetic domains are designated in FIG. 6, and one should be careful not to confuse these with the protein designations shown in the third column of Table III. For example the CelE1 protein is comprised of the second genetic domain in the celE gene.

Identification of N-terminal Sequences of Tok7B.1 Cellulases

The culture supernatant from the Tok7B.1 strain was chromatographed on a Mono-S column (Pharmacia) at pH 5.0 in 10 mM sodium acetate buffer at a flow rate of 1 ml/min. The bound proteins were eluted with a 30 ml linear gradient of NaCl from 0–250 mM. Each of the fractions collected was assayed for CMCase activity. 73% of the total CMCase activity was collected into fractions and 27% of the activity was found in the column flow-through. The proteins from fractions that demonstrated CMCase activity were electrophoresed on an 8% SDS polyacrylamide gel. Protein bands in fractions containing cellulase activity could be observed in a Coomassie-stained 8% SDS polyacrylamide gel. The cellulase activity of these bands was confirmed in part by overlaying the SDS polyacrylamide gel with an agarose gel containing carboxymethyl cellulose (CMC). Cellulases not denatured by the SDS degrade the CMC in the agarose gel. These areas of degraded CMC can be identified by staining with Congo Red using the methods of Beguin (1983) and Mackenzie and Williams (1984). Proteins of interest were blotted from the SDS-PAGE gel onto an Immobilon membrane and then the amino terminal sequences determined by Edman degradation (Matsudaria, 1987). The sequences determined for each of the individual bands are shown in a composite drawing (FIG. 1). CMCase activity that was not captured on the Mono-S column was subsequently buffer-exchanged into 12 mM Tris buffer pH 9.0, chromatographed on a Q sepharose column (1.5×6 cm), and eluted with a 30 mL linear gradient of 0–250 mM NaCl. Fractions that contained CMCase activity were electrophoresed on an 8% SDS PAGE and gave a protein band with identical apparent molecular weight and N-terminal sequence to the B5 band (FIG. 1) previously identified from the S-sepharose column.

The N-termini of each of these proteins was determined by Edman degradation. Only two different amino acid sequences were determined from the six proteins N-terminally sequenced. The N-terminus of the celE gene product was homologous with four of the proteins identified and the N-terminus of the celB gene product wash homologous with the two remaining protein bands. The amino acid sequence information served first to identify the genes that were expressing the cellulases useful for the applications. Second, the N-terminal sequences were compared with the protein sequences in GenBank using the Basic Linear Alignment Search Technique (BLAST. Jauris, et al., 1990). This confirmed that the two proteins sequenced belonged to the glycosyl-hydrolase family. The celB gene product has an amino-terminal sequence which shares significant homology with a general class of xylan degrading enzymes referred to as Family F beta-glycanases (Gilkes et al., 1991) or Family 10 glycosyl-hydrolase (Henrisatt, 1991). The CelE gene product shares homology with family E beta-glycanases/ Family 9 glycosyl-hydrolases.

Strategy for the Cloning of the Cellulase Genes

Our strategy for identifying the Tok7B.1 glycolytic genes was to employ two approaches simultaneously. 1) Polymerase chain reaction (PCR) with primers based on the sequence information obtained from the BLAST search was used PCR to amplify gene sequences from the Tok7B.1 genomic DNA preparations. 2) An expression library of the Tok7B.1 genomic DNA was constructed and screened for the expression of proteins able to degrade CMC.

Methods and Prior Art

Agarose gel electrophoresis, plasmid isolation, M13 mp10 single stranded DNA isolation, use of DNA modifying enzymes and E. coli transformation were performed as described by Sambrook et al. (1989).

Genomic DNA Preparation

Tok7B.1 genomic DNA was prepared from a cell culture which had been grown under anaerobic conditions for 1–2 days without shaking at 70° C. in 2/l media. Cells were harvested from the growth media by centrifugation at 5000 rpm for 10 minutes, then resuspended in 50 ml TES buffer before a second centrifugation step. Cell pellets were then resuspended in 5 ml 50 mM Tris pH 8.0, mixed with 374 µl 0.5M EDTA and incubated for 20 minutes at 37° C. After the addition of 550 µl freshly prepared lysozyme (10 mg/ml), the mixture was incubated at 70° C. for 20 minutes, mixed with 250 µl Streptomyces griseus protease (40 mg/ml) and 310 µl 10% SDS, then left to incubate overnight at 70° C. After allowing the lysed cells to cool to room temperature, the resulting clear solution was phenol extracted 2–5 times until no material could be seen to partition at the interface. The remaining volume of the sample was estimated and a 1/10 volume of 3M Sodium acetate was added and mixed, then 2.5 volumes of 95–100% ethanol gently layered onto the top of the sample. DNA could being seen as a stringy white precipitate at the interface of the two liquids and could be removed by spooling onto the end of a Pasteur pipette. Spooled DNA was transferred into a 1.5 ml microcentrifuge tube and washed in 70% ethanol before air drying for 1–3 hours. The resulting DNA pellet was resuspended in TE buffer and left overnight to fully dissolve. All genomic DNA preparations were stored at 4° C.

Isolation of the Tok7B.1 celE Gene using Consensus PCR and Genomic Walking PCR

Figure 3:
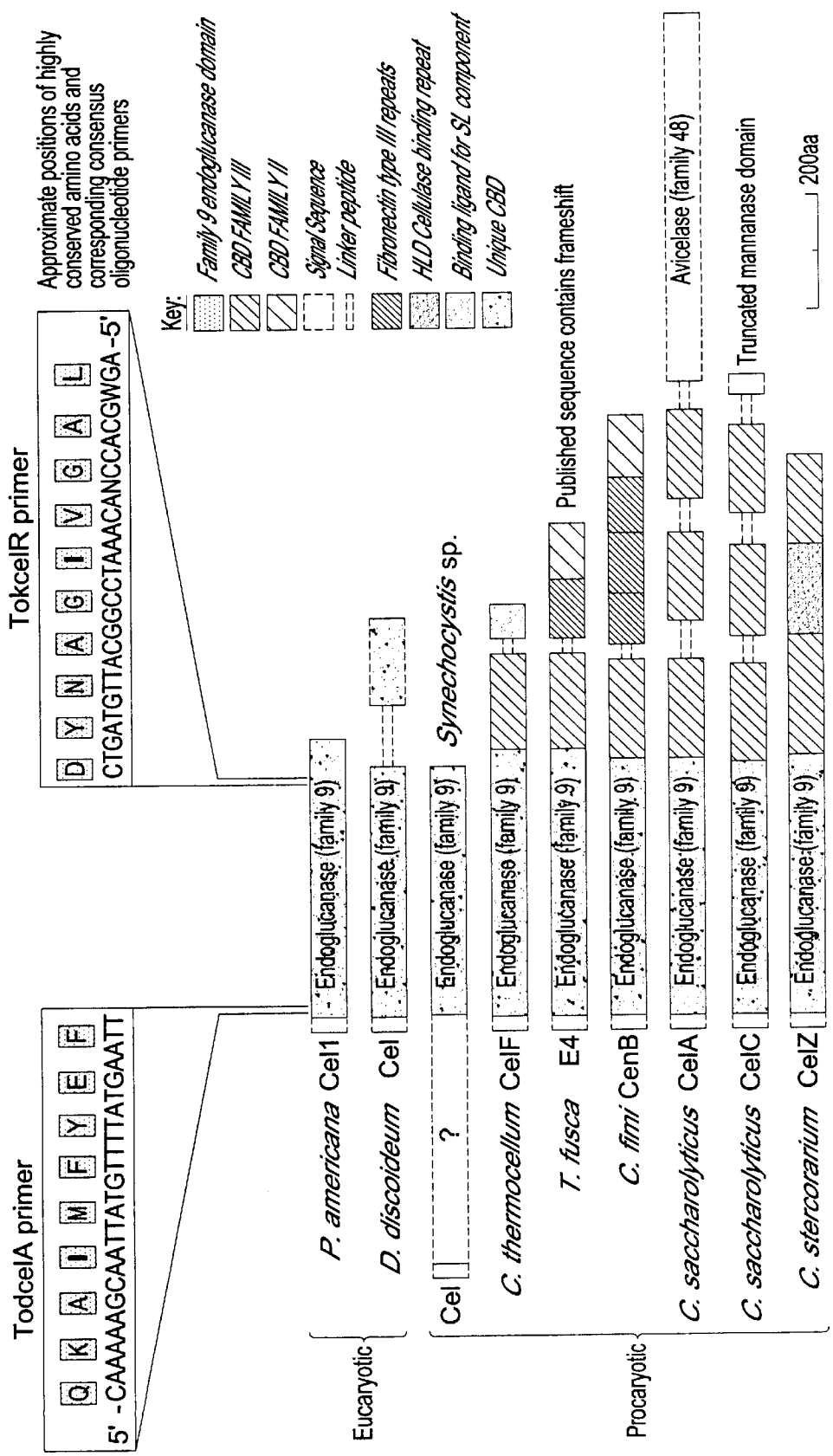
FIG. 3 is a diagram of two consensus primers TokcelA and TokcelB and their relationship to other family 9 cellulases.

The Tok7B.1 celE gene, gene product CelE, was identified by amino-terminal sequencing of cellulolytic peptides secreted by Tok7B.1 (FIG. 2). The celE gene codes for a family 9 glycosyl hydrolase based on comparison to translated gene sequences in the GenBank database. The CelE peptide sequence shared highest similarity to family 9 glycosyl hydrolases from other thermophilic Clostridial microorganisms. Homology alignments of family 9 genes indicated that it would be possible to design consensus oligonucleotide primers which would bind to DNA coding for clusters of highly conserved amino acids found in all thermophilic Clostridial family 9 glycosyl hydrolases. These consensus primers could then be used in PCR to amplify family 9 glycosyl hydrolase genes from Tok7B.1. Two primers were designed, the first, tokcela, bound to DNA coding for the peptide sequence QKAIMFYEF, and tokcelr, which bound in the reverse orientation (with respect to the gene sequence) to DNA coding for the peptide sequence DYNAGFVGAL (FIG. 3).

The tokcela and tokcelr primers were used to amplify an approximately 1300 bp PCR product from Tok7B.1. This product was ligated into M13 mp10 (Messing, 1983), transformed in E coli strain JM101 and plated to give individual recombinant plaques. In order to test whether the PCR product was generated from a single gene, or from multiple genes, PCR product was reamplified from individual plaques using the M13 forward and reverse primers then mapped by restriction digestion with Tsp509I. A total of 12 individual PCR products were restriction mapped and all showed identical restriction patterns. Six of these PCR products were sequenced and all showed identical DNA sequence. This data indicated that all cloned PCR products were amplified from a single family 9 glycosyl hydrolase gene present on the genome of Tok7B.1. In order to obtain the complete celE gene sequence, new PCR primers were designed to allow genomic walking upstream and downstream of the region covered by the 1300 bp PCR product (FIG. 4A). Standard subcloning and DNA sequencing techniques were used to obtain 6416 bp of DNA sequence containing the entire celE gene sequence plus flanking upstream and downstream sequence (FIG. 4B). The complete DNA sequence and translated peptide sequence of the celE gene is given in Sequence #2.

Genomic Library Construction and Screening

Genomic DNA from Tok7B.1 was partially digested with the restriction endonuclease Tsp509I to give DNA fragments in the size range of 6–8 kb. These fragments were then ligated into XhoI-digested λZapII (Stratagene, 11011 North Torrey Pines Road, La Jolla, Calif. 92037, USA) then packaged and plated according to protocols supplied by Stratagene. Individual plaque isolates shown to contain genomic inserts using the blue/white lacZ complementation system present in λZapII were replated, and a total of 1600 genomic insert containing plaques were screened for thermophilic cellulase and xylanase activity at 70° C. using the substrate overlay method of Teather and Wood (1982). Cellulase activity was detected using the soluble cellulose derivative carboxymethyl cellulose (CMC). Plaques were also screened for cellolobiohydrolase activity using the chromogenic substrate methylumbelliferyl cellobioside (MUC) as described by Saul et al. (1990).

Two positive λZapII plaques, designated W2-4 and N17, were isolated which expressed thermophilic xylanase and/or cellulase activity (FIG. 5A). These recombinant phage were converted to Bluescript SK- plasmids using the standard Exassist excision procedure described by Stratagene. Each plasmid was restriction mapped using a range of restriction endonucleases. Common restriction endonuclease digestion patterns indicated that W2-4 and N17 contained common overlapping DNA from the same region of the Tok7B.1 genome (FIG. 5A).

DNA Sequencing and Sequence Analysis of the Tok7B.1 celB and celA Genes

The recombinant DNA from W2-4 and N17 was partially sequenced by creating simple plasmid deletions using known restriction sites within the plasmid insert (Gibbs, et al. 1991). Initial DNA sequence homology comparison data indicated a gene coding for a multidomain enzyme with a xylanase and a cellulase domain and several internal cellulase binding domains (CBD). The Genomic DNA contained by W2-4 was sequenced in full, and portions of N17, by subcloning and sequencing internal restriction fragments and using synthesized DNA oligonucleotide primers (primers are listed in Table I). Analysis of the complete sequence of W2-4 showed that the DNA contained a complete gene, celB, coding for a nine-domain protein designated CelB. The 3'-portion of a further gene was observed to lie upstream of the celB gene. This gene, designated celA, shared at least 1 domain in common with the celB gene. The complete coding sequence of celA was obtained using Genomic Walking PCR (GW-PCR) as described by Morris et al. (1994). Representative GW-PCR products spanning the region of the celA gene are depicted in FIG. 5B. The complete DNA sequence containing the celA and celB genes is depicted in FIG. 5C, with each gene shown according to its translated domain structure. The complete DNA sequence and translated peptide sequence of the celA and celB genes is given in Sequence #1. The translated product of the celB gene matches perfectly with two amino-terminal sequences obtained for native cellulolytic peptides secreted by Tok7B.1 (FIG. 2, peptides B2 and B4), implying that the celB gene expresses one of the major cellulases secreted by Tok7B.1. A complete summary of the protein domain structures of CelA and CelB is given in FIG. 6.

The complete celE gene was observed to code for a large multidomain-multicatalytic enzyme with a putative length of 1751 amino-acids (unprocessed) and is composed of at least 10 discrete functional domains based on homology comparisons (FIG. 6). The family 9 glycosyl hydrolase domain is the amino-terminal domain of the full length CelE, while the central domains of CelE (domains 4–9, FIG. 6) are virtually identical to the central domains of CelB (domains 3–8, FIG. 6), the only exception being the relative lengths of each PT-linker. The carboxy-terminal domain of CelE (domain 10, FIG. 6) is homologous to the carboxy-terminal endoglucanase domain (family 44 glycosyl hydrolase) of ManA from C. saccharolyticus. This domain can degrade xylan as well as carboxymethylcellulose (Gibbs et al. 1991) and activity assays have shown that the carboxy-terminal domain of Tok7B.1 CelE is also an endoglucanase with weak xylanase activity.

Identification of Further Tok7B.1 Cellulase Genes Using GW-PCR, celC and celH

In the process of obtaining the complete coding sequence of the Tok7B.1 celE gene further ORFs were identified upstream of this gene. Homology comparisons indicated that these genes also coded for cellulolytic enzymes. GW-PCR was used to obtain DNA sequence from upstream of the celE (FIG. 7A.) Two further genes were identified in this way. Both of these genes, designated celC and celH, code for multidomain, multicatalytic proteins, with the same general structure as CelA, CelB and CelE. As the DNA sequence obtained was not contiguous, long-template PCR (Expand Long template PCR System, Boehringer Mannheim, Australia Pty. Ltd.) was used to amplify DNA between the sequenced regions to confirm that they were contiguous (FIG. 7A). Approximately 13500 bp of genomic DNA upstream of the celE gene was partially sequenced.

Identification of celF and celG

During the isolation of the complete celA gene sequence the primer N17a was used as a genomic walking primer. A number of PCR products were obtained which did not match DNA sequence already obtained for the celB and celA genes. It was clear from these results that the N17a primer was CelB. Upstream of this second xydanase domain a further gene was identified coding for an enzyme with a carboxy-terminal family 48 glycosyl hydrolase domain. These genes were designated celF and celG respectively (FIG. 7B). Oligonucleotide primers specific to the carboxy-terminal end of the celG gene and the amino-terminal end of the celF gene were synthesized and used in combination with oligonucleotide PCRs which bound to DNA coding for the CBDs found in celA, celB, celE, celC and celH. The amplification of PCR products indicated that celG and celF coded for the proteins with the same basic domain structure of the other Tok7B.1 cellulolytic genes. The amino-terminal domain of celG was not identified, the carboxy-terminal of celF was identified as a family 48 glycosyl hydrolase with high homology to the carboxy-terminal domains of celG and celC.

Transfer of Tok7B.1 Genes into Controlled-Expression Plasmid Vectors

To facilitate the transfer of Tok7B.1 cellulase genes into controlled-expression plasmid vector the general method of Gibbs et al. (1991) was used. PCR was used to amplify full length cellulase genes (and portions of cellulase genes). Oligonucleotide primers corresponding to each end of the gene were engineered to contain restriction sites allowing directional ligation of restriction digested PCR product into plasmid multiple cloning sites. Table II. lists the oligonucleotides designed for PCR amplification and directional ligation of the various Tok7B.1 genes into controlled expression vectors. Each primer contains one or more restriction endonuclease site(s) to facilitate ligation of PCR product into plasmid vector predigested with the same restriction enzyme, resulting in an in-frame gene fusion between each thermophilic gene and a signal peptide sequence encoded on the vector. The various genes and gene fragments transfer into pJLA602 by this method are shown in FIG. 8.

Phylogenetic Analysis of Tok7B.1

The 16S SSU rRNA gene was isolated using PCR. A PCR product was generated using oligonucleotide primers designed to amplify the 16S SSU rRNA gene from all known prokaryotic species. An approximately 1800 bp PCR fragment was obtained which was cloned into M13 mp10 in the forward and reverse orientation, and sequenced (Seq #3). The SSU rRNA gene sequence obtained was compared to all genes in the GenBank database. Close homologs of the Tok7B.1 SSU rRNA gene were aligned using the GCG multiple alignment software 'Pileup'. Resulting aligned sequence files were subsequently analyzed using parsimony methods (Swofford, 1993). FIG. 9 shows the phylogenetic position of Tok7B.1 amongst cluster D of thermophilic Clostridia (Rainey et al., 1993).

Cloning of Individual genes into an E. coli Expression Vector

From the celE and celB genes a number of new truncated genes containing either individual cellulase catalytic domains Cel E1 or catalytic domains connected to cellulose binding domains by linker sequences, Cel E1/2, CelE1/2/3 and CelB4/5 have been constructed (Table III). Each of the genes have been individually expressed in E. coli using the bacteriophage T-7 RNA polymerase/promoter system (Studier and Moffatt, 1986).

Expression Cloning of the CelE Domains D2

The N-terminal CelE endoglucanase catalytic domain (FIG. 6) and the first cellulose-binding domain (CBD) (FIG. 6) were used to construct expression plasmids pcelE1 and pcelE1/2 respectively. These celE gene domains were obtained from the M13-mp10 clones, M13celE1 and M13celE1/2. The first step in the cloning process was the PCR amplification of domain 2 or domains 2 plus 3 of the celE gene from Tok7B.1 genomic DNA (FIG. 10). Unique restriction endoglucanase sites were introduced by the PCR primers at the 5' and 3' ends of the gene fragments. An SphI site was incorporated at the 5' end of the native gene at the predicted translational start site, which encodes the translational ATG start codon, and BgIII sites were incorporated at the 3' ends of the specific gene domains at convenient locations. Translational stop codons were introduced just upstream of the BgIII sites. The PCR fragments were blunt end ligated directly into SmaI digested M13mp10 vector, (Messing, 1983) to give the clones M13-celE1 and M13-celE1/2 (FIG. 11).

Using the pET9a vector (Novagen) E. coli expression plasmids were constructed. The plasmid utilizes the T7 Polymerase promoter for gene expression, (Studier, et al., 1990). An intermediate construct was employed to facilitate the cloning process. The celE1/2/3 gene was amplified using PCR, the forward direction primer tokcbdf, and the reverse direction primer tokcel (FIG. 11). The forward primer, tokcbdf introduces a NdeI site at the 5' end of the mature celE gene and thereby encodes the translational ATG start codon. The introduction of the NdeI restriction site changed the first two amino acids encoded in the mature sequence from GT to AA Table III. The reverse PCR primer, tokcel, was homologous to the native gene sequence at the NdeI site in CBD domain 3. The PCR fragment was digested with NdeI and gel-purified with silica gel technology using a Qiaex II gel extraction kit from Qiagen Inc. The fragment was ligated into the NdeI site of the pET9a vector (FIG. 12). The resulting plasmid, pMcelE-NdeI, was digested with PstI and BamHI and the vector fragment was isolated from the digest by agarose gel electrophoresis and silica gel purification. The M13-celE1 and M13-celE1/2 clones were digested with PstI and BgII and the resulting celE gene fragments, celE1 and celE1/2, were isolated from the digest by agarose gel electrophoresis and silica gel purified (FIG. 12). The fragments were ligated to the PstI-BamHI digested pcelE-NdeI plasmid to form the final clones, pMcelE1 and pMcelE1/2 (FIG. 12). Both the BgIII and BamHI restriction enzymes produce compatible sticky ends but these sites are lost upon ligation.

Expression Cloning of the CelE D2/3/4/5

The pcelE1/2/3 plasmid encodes the first catalytic domain of the celE gene plus the first two cellulose-binding domains D3 and D5 (Table III) in a pET9a expression vector. The catalytic domain D2 and CBD D3 used in the construction of the pcelE1/2/3 expression plasmid was obtained from the pcelE1/2 plasmid. The second cellulose-binding domain D5 was obtained from the pRR9 plasmid (FIG. 8). The construction of the final plasmid required a three-way ligation that is outlined in FIG. 13.

The entire native celE gene was amplified by PCR from genomic Tok7B. 1 DNA using the tocelef forward primer and the tokceler3 reverse primer Table II. The PCR primers contained an SphI site in the forward primer, which introduces the ATG translational start codon, and a SalI site in the reverse primer. The PCR fragment was digested with SphI and SalI and cloned into the SphI and SalI sites of the polylinker of the *E. coli* expression vector pJLA602, to produce the pRR9 plasmid (FIG. 8). To obtain the gene fragment encoding domains 4 and 5 for ligation with the pcelE1/2 plasmid, the region from the NcoI site in D3 through D5 was PCR amplified from the pRR9 plasmid (FIG. 13). Tokcelef, the forward primer, was homologous to the celE sequence at the NcoI site and the tokcelebamr reverse primer was homologous to the end of D5, the second CBD in celE and introduced a BamHI cloning site. This PCR fragment was digested with NcoI and BamHI and purified. The celE fragment from D2 to the 5' end of D3 at the NcoI site was isolated from the plasmid pcelE1/2 (FIG. 13). The plasmid was digested with NdeI and NcoI and the celE fragment was isolated from the vector fragment by gel electrophoresis and silica gel technology. The vector, pET9a, was digested with NdeI and BamHI and purified by gel electrophoresis and silica gel technology. The two celE fragments were ligated to the pET9a expression vector in a three-part ligation to produce the pcelE1/2/3 plasmid (FIG. 13).

Expression Cloning of CelB4/5

A plasmid that expressed the CelB4/5 protein of the Tok7B.1 celB gene was constructed in the *E. coli* expression vector, pET9a, as described below. Domains 7, 8 and 9 containing a CBD and catalytic domain were PCR amplified from the Tok7B.1 genomic DNA using primers tokcbdf and tokcelbr. These primers incorporated into the PCR fragment a unique 5' NdeI site by the forward primer and a unique 3' BamHI site (FIG. 8). The fragment was digested with NdeI and BamHI and ligated into the NdeI and BamHI digested pJLA602 expression vector to produce the pRR6 plasmid (FIG. 14). The pRR6 plasmid was digested with NdeI and BamHI and the celB gene was purified from the vector fragment by gel electrophoresis and silica gel technology. The pET9a vector was digested with NdeI and BamHI and purified by gel electrophoresis and silica gel technology. The two fragments were ligated together to produce the pcelB4/5 plasmid (FIG. 14).

Expression Cloning of CelB3/4/5

The CBDs of the celE gene, domains 4 & 5, (FIG. 8) are very homologous to the CBDs of the celB gene, domains 3 & 4, (FIG. 8). Also, the two CBDs within the genes are very homologous to each other. This homology is useful for the construction of the pcelB3/4/5 construct in the *E. Coli* expression vector pET9a. A homologous region of domain 3 of the celB gene is cloned from the celE gene construct. This is done by taking advantage of a BglII site in each of the homologous celE CBD domains 4 & 5. This BglII fragment is isolated by restriction digest from the celE construct pRR10 which encodes domains 3,4,5, & 6 of the celE gene, FIG. 8, in the pJLA602 expression vector. This BglII fragment contains the 3' portion of celE Domain 3 and the 5' portion of celE Domain 4. This BglII fragment is ligated into the BglII site of Domain 4, the CBD, of pcelB4/5. The resulting plasmid is pcelB3/4/5.

Expression Cloning of CelE3/B5

This clone is constructed in the *E. Coli* expression vector pET9a. Domain 3 of the celE gene is PCR amplified from pcelE1/2/3. The forward and reverse primers incorporated into the PCR fragment provide unique 5' NdeI and 3' BstEII sites. The PCR fragment is digested with NdeI and BstEII and ligated to the pcelB4/5 vector which is digested with NdeI and BstEII and gel purified (FIG. 14A). The NdeI and BstEII digest of the pcelB4/5 results in the removal of the native celB CBD as well as 29 amino acids from the PT linker.

Fermentation of the *E. coli* Expressing Cloned Cellulase Genes

The pcel E1, pcel E1/2, pcel E1/2/3, pcelB4/5, pcelB3/4/5 and pcel E3/B5 expression plasmids were transformed into *E. coli* DE3-BL21 (Stratagene Corp.). Transformants were grown at 37° C. to an OD600 of 1.0 in 250 mL of L-broth containing 50 µg/ml Kanamycin. The 250 ml of L-broth was then used to inoculate a 20 L Chemap fermentor containing 12 liters of media. The fermentation media consisted of 12 g/L of tryptone, 24 g/L yeast extract, $KH_2PO_4$ 2.3 g/L, 12.5 g/L $K_2HPO_4$, 1 mL/L Antifoam 289 (Sigma), 4 g/L glycerol, 1 mL/L 1.0 M $MgSO_4.7H_2O$ and 50 µg/mL Kanamycin. The transformants were grown at 37° C. to an OD600 of approximately 12 and then expression was induced by the addition of IPTG at a concentration of 95 mg/L. After a 3h induction the cells were harvested by centrifugation in 500 ml bottles at 7,000×g for 10 min. A typical yield from a 12-L fermentation was 300 g of wet cell paste. Cell pellets were then frozen at −80° C. prior to lysis and purification of the recombinant proteins.

Purification of the Cel E1 and Cel E1/2 Cellulases

The *E. coli* fermentation cell pellets were thawed by resuspending the frozen cells in two volumes of 20 mM Tris buffer pH 8.0. The cells were homogenized with a Virtis Virtishear 1200 for 20 min., then lysed by one passage through a Microfluidizer (Microfluidics Corp.) at a pressure of 9600 psi. The lysate was centrifuged at 43,000×g for 30 min. The pellet was discarded and the supernatant was combined with sufficient ammonium sulfate to make a 1 molar solution. The ammonium sulfate solution was stored overnight at 4° C. then centrifuged at 15,000×g for 20 minutes. The supernatant was then chromatographed on phenyl sepharose. The column (5×10 cm) was washed with 10 mM Tris pH 8.0, 1.0 M ammonium sulfate. After the column effluent had an A280 of less than 0.1 AU, the protein was eluted with a 300 mL linear gradient from 1.0 M to 0 M ammonium sulfate. This column eluent was used in the application testing. Each of the constructs tested in the application was electrophoresed on a 12% polyacrylamide gel and then blotted to an Immobilon membrane and N-terminally sequenced. FIG. 16 shows the expected N-terminal sequenced versus the sequence found upon Edman degradation.

Purification of the CelB5 and CelB4/5 Cellulases

When the Cel B4/5 protein purification described below is carried out in the presence of a protease inhibitor cocktail consisting of phenymethyl sulfonyl fluoride, EDTA and Aprotinin, the full length protein, CelB4/5, consisting of the CBD, PT linker region and catalytic domain is purified. However, in the absence of the protease cocktail, the linker region is cleaved to yield the Cel B5 endoglucanase domain alone, without the CBD or PT linker domains.

For purification of the CelB4/5, 280 g of cells expressing celB4/5 were thawed in three volumes of 10 mM Tris, pH 7.0 in the presence of the protease cocktail described above. The thawed cells were virtisheared for 20 min. then lysed as before by a single pass on the Microfluidizer. The lysate was centrifuged for 10 min. at 3,500×g. The resulting supernatant (820 ml) was heated in a 50° C. water bath for 10 minutes, then centrifuged for 20 minutes at 3,000×g. Sufficient (NH$_4$)$_2$SO$_4$ was added to give a 20% saturated solution, the solution was centrifuged for 30 min. at 3,000×g and the pellet discarded. More (NH$_4$)$_2$SO$_4$ was added to the supernatant until the solution was 35% saturated, the solution was centrifuged for 30 min. at 3,000×g and the supernatant discarded. The pellet was resuspended in 10 mM Tris pH 8.0, 0.5 mM EDTA, 1 mM Aprotinin. The solution was chromatographed on a 430 ml DEAE column (5 cm×20 cm) and eluted with a two-step NaCl gradient. Step one of the elution profile was 0 to 150 mM NaCl wash in 300 ml, step two was a wash of 150 mM to 260 mM NaCl linear gradient in 1200 ml. The CMCase activity eluted between 750–950 ml and gave 1.5 g of CelB4/5 protein.

CelB5 was purified in an identical manner except the only protease inhibitor added to the cell lysate supernatant was 1 mM PMSF. CelB5 eluted in an identical manner from the DEAE column. The total protein purified was 1 g from about 280 g of cells.

Purification of CelB3/4/5

400 g of frozen cells are thawed in 800 ml of 10 mM Tris, pH 8.0, 0.5 mM EDTA. The cells are lysed by one pass through the Microfluidizer at 12,000 psi. The lysed sample is then centrifuged at 7,800×g for 50 min. To the supernatant (950 ml) is added slowly 100.7 g of ((NH$_4$)$_2$SO$_4$ to give a 20% saturated solution. The solution is stirred overnight for 12 h at 4° C. The precipitated proteins were removed by centrifugation for 30 minutes at 14,000×g. The remaining supernatant is brought up to 40% (NH$_4$)$_2$SO$_4$ and left to stir for 48 h at 4° C. The precipitate is pelleted by centrifugation for 30 min at 15,000×g. The pellet is resuspended in 20 mM Mes pH 6.0. The conductivity is reduced to less than 3 ohms/cm$^2$ by diafiltration using a 30 kD Filtron membrane. The dialysate is centrifuged to remove any precipitate and chromatographed on S-sepharose (10 cm×6 cm) and eluted with a linear salt gradient from 0.1 M to 0.35M. Fractions containing activity of greater than 200 units/mL are pooled. The final pool contains 720 mg of protein which is approximately 52% pure as determined by densitometry scanning of a Coomassie stained 12% SDS PAGE of the pool.

Purification of CelE3/B5

400 gm of E. coli DE3-Bl21 are thawed in 10 mM Tris, pH 8.0, 0.5 mM EDTA. The cells are lysed by passage through the microfluidizer at 12,000 psi. The precipitate is removed by centrifugation of the lysate for 30 min at 8,000×g. To the supernatant is then added solid (NH$_4$)$_2$SO$_4$ to give a 20% saturated solution. The precipitate is removed by centrifugation at 14,000×g for 30 min and the supernatant was loaded on a phenyl sepharose column 6 cm×10 cm. The protein is eluted with a 2L reverse linear gradient from 1 M to 0 M (NH$_4$)$_2$SO$_4$ in lysis buffer. The bulk of the activity is collected in three fractions. Each of the fraction contains 250 ml. Each of the fraction is analysed for the activity. The conductivity is reduced to less than 3 ohms/cm2 by diafiltration using a 30 kD Filtron membrane with a 10 mM Immidazole pH 7.0. The dialysate is chromatographed on S-sepharose (10 cm×6 cm) and eluted with a linear salt gradient from 0 M to 0.23 M. Fractions containing activity of greater than 250 units/mL are pooled. The final pool contains 720 mg of protein which is approximately 86.9% pure as determined by densitometry scanning of a Coomassie stained 12% SDS PAGE of the pool.

pH Rate Profiles of Purified Cellulases

The pH rate profiles and thermostability of the cellulases were determined. These data serve to define the pH extremes at which an enzyme could be used in an application. Cellulases were assayed at 50° C. for the determination of the pH rate profiles. The catalyzed rates of reaction at each pH are expressed as fractions of the fastest observed rate. This is calculated by dividing the rate of reaction at each pH by the highest reaction rate observed at any pH, the highest reaction rate is therefore plotted as 1.0. The CMC substrate and buffer in each case was made with an appropriate buffer for each pH being tested. The following buffers were employed for each of the assays, at pH 3.0 sodium tartrate (25 mM), pH 4.0 sodium tartrate (50 mM), pH 5.0 sodium acetate (50 mM), pH 7.0 sodium phosphate (50 mM), pH 9.0 glycine (50 mM), pH 10.0 glycine (50 mM), pH 11.0 CAPS (50 mM), pH 12.0 sodium phosphate (50 mM). 2% CMC was made up at each pH in the buffers listed. No more than 10 µl of enzyme was added to the total reaction mixture of 0.5 ml so that the pH of the reaction would not be effected.

Thermal Stability of Cellulases

The thermal stability of these proteins is summarized in Table IV. The addition of CBDs to the catalytic domains has different effects on the thermal stability of the protein constructs. The CelE1 was dramatically stabilized by the addition of the cellulose binding domains, there is a 25° C. increase in the stability of the CelE1/2 relative to CelE1.

Assays to determine the thermostability of the cellulases with time were carried out in one of two ways depending on the temperature at which the studies were done and the time of incubation. At temperatures of up to 80° C. or if the samples were incubated for less than two minutes then stability studies were done by protocol 1. An aliquot (40 µl) of the purified cellulase was diluted into an aliquot (200 µL) of incubation buffer, 50 mM sodium phosphate buffer at pH 7.0, that was preheated in an 80° C. water bath. At the specified time points aliquots (25 µl) were withdrawn from the diluted sample incubated at the designated temperature and diluted into 475 µl of ice cold incubation buffer. Each of the time points was then assayed to determine the remaining cellulase activity using the standard CMCase assay.

Protocol 2 was used when incubations of above 80° C. were done for a time in which any assay point exceeded two minutes of incubation time. In this case sufficient cellulase for an individual CMCase assay was placed in a tube and preheated to 80° C. At time 0 the samples were then transferred to a water bath at a higher temperature for example 85° C. or 90° C. At the designated time points the samples were withdrawn and placed in an ice water bath. Each of the time end points was then assayed to determine the remaining cellulase activity with time using the standard CMCase assay.

Structural Characterization of Purified Cellulases

Characterization of the CelB5 protein by MALDI-TOF and N-terminal sequencing shows the linker domain is clipped between T999 and A1000 in the full length CelB protein sequence and that the two C-terminal amino acids K1424 and N1425 are also proteolyzed (FIG. 15). The N-terminal sequence of the expressed proteins were determined using the techniques of Matsudaria (1987) in which proteins were electrophoresed on SDS PAGE, blotted to PVDF membranes and then N-terminally sequenced by Edman degradation (FIG. 15).

Application Testing of Tok7B.1 Cellulase Constructs

The purified enzymes were tested in the denim stonewash application, under the same conditions that were used in the initial evaluation of the cellulase supernatants. Results are shown in Table IV. Cellulase constructs that gave a stonewashing effect and showed a dose dependent increase in abrasion with increasing concentrations of enzyme were lacking a cellulose binding domain. Results demonstrated the CelB5 and CelE1 protein constructs gave the best stonewash effect.

REFERENCES

P. Beguin, Nalan. Biochme. 131, 333 (1983)

C. R. Mackenzie and R. E. W. Williams, Can. J. Microbiol. 30, 1522 (1984)

Jauris, S., et al. Mol. Gen. Genet. 223: 258–267 (1990)

Gilkes N. R., Henrissat B., Kilburn D. G., Miller M. C. and Warren R. A. J. (1991) Domains in microbial beta-1,4-glycanases: Sequence conservation, function, and enzyme families. Microbiological Reviews 55:2303–2315

Henrissat B. (1991) A classification of glycosyl hydrolases based on amino acid sequence similarities. Biochem. J. 280:309–316 Gibbs, M. D., D. J. Saul, E. Luthi and P. L. Bergquist. The beta-mannanase from 'Caldocellum saccharolyticum' is part of a multidomain enzyme. AppI. Env. Microbiol., 58, 3864–3867, 1992.

Gilkes N. R., Henrissat B., Kilburn D. G., Miller M. C. and Warren R. A. J. (1991) Domains in microbial beta-1,4-glycanases: Sequence conservation, function, and enzyme families. Microbiological Reviews 55:2303–2315

Giorda, R., Ohmachi, T., Shaw, D. R. and Ennis, H. L. (1990) A shared internal threonine-glutamic acid-threonine-proline repeat defines a family of Dictyostelium discoideum spore germination specific proteins. Biochemistry 29:7264–7269. Accession No. M33862.

Henrissat B. (1991) A classification of glycosyl hydrolases based on amino acid sequence similarities. Biochem. J. 280:309–316

Jauris, S., Rucknagel, K. P., Schwarz, W. H., Kratzsch, P., Bronnenmeier, K. and Staudenbauer, W. L. (1990) Sequence analysis of the Clostridium stercorarium celZ gene encoding a thermoactive cellulase (Avicelase I): identification of catalytic and cellulose-binding domains. Mol. Gen. Genet. 223:258–267. Accession No. X55299.

Kaneko, T., Sato, S., Kotani, H., Tanaka, A., Asamizu, E., Nakamura, Y., Miyajima, N., Hirosawa, M., Sugiura, M., Sasamoto, S., Kimura, T., Hosouchi, T., Matsuno, A., Muraki, A., Nakazaki, N., Naruo, K., Okumura, S., Shimpo, S., Takeuchi, C., Wada, T., Watanabe,A., Yamada, M., Yasuda, M. and Tabata, S. (1996) Sequence analysis of the genome of the unicellular cyanobacterium Synechocystis sp. strain PCC6803. II. Sequence determination of the entire genome and assignment of potential protein-coding regions. DNA Res. 3:109–136. Accession No. D64003.

Lao,G., Ghangas, G. S., Jung, E. D. and Wilson, D. B. (1991) DNA sequences of three beta-1,4-endoglucanase genes from Thernomonospora fusca. J. Bacteriol. 173:3397–3407. Accession No. M73322.

Matsudaria, P. (1987) Sequence from picomole quantities of proteins electroblotted onto polyvinydifluoride membranes, J. Biol. Chem. 262 10035–10038.

Meinke, A., Braun, C. J., Gilkes, N. R., Kilburn, D. G., Miller, R. C. Jr. and Warren, R. A. J. (1991) Unusual sequence organization in CenB, a inverting endoglucanase from Cellulomonas fimi. J. Bacteriol. 173:308–314. Accession No. M64644.

Messing, J. (1983) Methods in Enzymology 101 (partC); Recombinant DNA, 20–78. Wu, R., Grsssman, L., Moldave, K. (eds) Academic Press, New York.

Morris, D., R. A. Reeves, M. D. Gibbs, D. S. Saul and P. L. Bergquist (1995). Correction of the celC pseudogene from Caldicellulosiruptor saccharolyticus and the activity of the gene product on kraft pulp. Appl. Environ. Microbiol. 61, 2262–2269, 1995.

Navarro, A., Chebrou, M. C., Beguin, P. and Aubert, J. P. (1991) Nucleotide sequence of the cellulase gene celF of Clostridium thermocellum. Unpublished. Accession No. X60545.

Rainey F., Ward N., Morgan H., Toalster R. and Stackebrandt E. (1993). Phylogenetic analysis of anaerobic thermophilic bacteria: Aid for their reclassification. J. Bact. 175:4772–4779

Sakka K., Yoshikawa K., Kojima Y., Karita S., Ohmiya K. and Shimada K. (1993). Nucleotide sequence of the Clostridium stercorarium xylA gene encoding a bifunctional protein with beta-xylosidase and alpha-L-arabinofurancsidase activities, and properties of the translated product. Biosci. Biotech. Biochem. 57:268–272

Sambrook J., Fritsch E. F. and Maniatis T. (1989). Molecular cloning: A laboratory manual. Cold Spring Harbor Laboratory Press, New York, U.S.A.

Saul D. J., Williams L. C., Grayling R. A., Chamley L. W., Love D. R. and Bergquist P. L. (1990). celB, a gene coding for a bifunctional cellulase from the extreme thermophile "Caldocellum saccharolyticum". Appl. Environ. Microbiol. 56:3117–3124

Studier, F. W. Rosenberg, A. H., Dunn, J. J. and Dubendorff, J. W. (1990) Methods in Enzymology 185: 60–89.

Studier, F. W. and Moffat, B. A. (1986) Use of a bacteriophage T7 RNA polymerase to direct selective high-level expression of cloned genes. J. Mol. Biol. 189:113.

Swofford D. (1993). Phylogenetic analysis using parsimony (PAUP), version 3.1.1 for the Macintosh. Smithsonian Institution (Pub), Washington D.C., U.S.A.

Teather R. M. and Wood P. J. (1982) Use of Congo Red polysaccharide interaction in enumeration and characterization of cellulolytic bacteria from the bovine rumen. Appl. Environ. Microbiol. 43:777–780

Teo V. S. J., Saul D. J., Bergquist P. L. (1995) cela, another gene coding for a multidomain cellulase from the extreme thermophile Caldocellum saccharolyticum. Appl. Microbiol. Biotechnol. 43:291–296. Accession No. L32742.

Tomme P., Warren, R. A. J. and Gilkes, N. R. (1995). Cellulose Hydrolysis by bacteria and fungi. Adv. Microbiol. Physiol. 37:1–81

Tucker, M. L. and Milligan, S. B. (1991) Sequence analysis and comparison of avocado fruit and bean abscission cellulases. Plant Physiol. 95:928–933. Accession No. M57400.

Winterhalter C., Heinrich P., Candussio A., Wich G. and Liebl W. (1995) Identification of a novel cellulose-binding domain within the multidomain 120 kDa xylanase XynA of the hyperthermophilic bacterium Thermotoga maritima. Mol. Microbiol. 15:431–444

What is claimed is:

1. A cellulase active protein substantially free of proteinases of native thermophilic and alkalinophilic origin and consisting of the (Cel B5) amino acid sequence extending from amino acid position No. A1001 through amino acid position No. P1424 or K1425 or N1426 in SEQ. ID No. 43.

* * * * *

SEQUENCE LISTING (1) GENERAL INFORMATION:

(iii) NUMBER OF SEQUENCES: 49

(2) INFORMATION FOR SEQ ID NO: 1:

(i) SEQUENCE CHARACTERISTICS:
      (A) LENGTH: 11707 base pairs
      (B) TYPE: nucleic acid
      (C) STRANDEDNESS: single
      (D) TOPOLOGY: linear (xi) SEQUENCE DESCRIPTION: SEQ ID NO: 1:

```
CCAATCTGTG TCATGTGCTG AAACAGCGGT TGCTGTACA CACTCGATGT GCCCACCGGC      60

GAAAAATCAA ATACAGAAAT ATATCGCCAG CTCTGAGCAG TTTTCCATCT TCTATTCGCA     120

GCAAATTTCA AAATGATTCT GGTTTATCTT ACTCGTACGC GTCTTTGTCA GCTCCTGCAA     180

TTGTTGATGA TGTTCGCTCG ATACTTACAT TCTGGCAGGA TTCGATATTA AGCAAAAAAG     240

ATGAGATTAG AAACATGGTT GGTGGAGATT GGAAAAAACC TCCTGCAGAG CAGGTTGTTG     300

CTGGACCACC TGCTGAATAC AAGTGGTATG CAACTGCTCA AATCAATGAC AGCGATTTTT     360

ACAACTCAAA TCTCATACCT CCGTTGCAAA GTGGTGACAG TCTCGTACTT ATGACAACAC     420

AGGGTATTGA TATGAGTCCT TCTGGAAATG TAATTAGAAA TGGTGTTTTT ATTTCACTTG     480

CTGAATATAC AGGATTCAAT GTCAATAGCA ACGGTGATCT AAAAATTATA TGGGACAGAC     540

CGAGCCAGCA AACAATAAAT GAAATTACCA ATGATTTGAA TTTGCCAATT GTTCCAACAC     600

CAACGCCTGT GCCAACAGCA AATGTAACCA CGGGTACCAC AAACAATTTC CAAATAATAA     660

ATCGAAGAAT GAGTATAGAG TAAGAAGGTT ATATTTTAAA ATAGTAGTCA AAAAGGGAAG     720

TGAGGAAGAT GAAGAAGAGG GTAATTTCAA TTCTTTCTTT ATTGTTTTTT TTAATAAACA     780

CGCTTGTAGG TACTTTGATA TTTCATCAGG AAGCAAAAGC AGCAGCATAT ACTGTTGATT     840

TTGAAGGTGC TGATACTTTA TCTTACTTTG CTTATGAAA ATCGAGCATA GCAGTTGACA     900

TGGGCAATGC ATATAATGGT AAAAGTAGTG TCAGGGTGTC AAATAGAAGT TCAATATGGG     960

ATGGAGTTGC AGTTGACGTT AAAAACATTA TGAACAATGG AACCACATGG GTAGTTTCAG    1020

CGTATGTAAA ACATAGCTAC CAGAAGCCGG TTGCATTTGG TATCTCAGCG GTTTACGACG    1080

ATGGAAGTGG GGTTAAGAGT ACTCTCATAG GTGAGGTTGT GGCTATTCCA AATTATTGGA    1140

AGAAAATTGT TGGTAAATGG ACTCCAAATA TTAGCAATGT CAGGAATTTG TTAATTGTAA    1200

TACACACAAT TGTAGAAAGC GAAGTAGATT ATAATGTTGA CTATATCCAA ATAATGGATG    1260

ATAATAGTTA CCTATCAAAT GCAGTGACAT TTTCAAGTGG ATTTGAAAGT GGCACTACCG    1320

AGGGTTGGCA GGCAAGGGGA AGCGGTGTTA CAGTAAAACC AGATAGCGTT GTGGCATATA    1380

GTGGCAAGTA TAGTTTGTAC GTCAGTGGAA GAACGTCAAA TTGGCATGGT GCACAGATTC    1440

CGGTAGATAC AATTTTGGAA CAGGGTAAAG TGTATAAAAT AAGTGTTTGG GTTTATCAGA    1500

ACAGTGGTTC AACTCAAAAA ATGTCATTAA CTATGCAAAG AAGATTTGCT ACAGATCCTT    1560

CAACAAGCTA TGAAAATCTG ATATATAACA GGGATGTACC GAGTAATACG TGGGTTGAGC    1620

TGAGTGGAAG CTACTCAATT CCTGCTGGTG TTACAGTTAG CGAGTTGTTG CTTTATGTTG    1680

AGGCACAAAA TGCAAATTTG GCTTTCTGGG TTGATGATTT AAAGATTTAT GATTTATCCA    1740

AGTTGGCTGA ACCTGAATGG GAGATACCAT CTTTGATAGA AAAGTATAGA GATTATTTCA    1800

AGTAGGAGT AGCTTTGTCT TACAAAAGCA TTGCCTCTGA TACAGAAAAG AAGATGGTTT    1860
```

-continued

```
TGAAGCATTT CAATAGTATT ACTGCAGGGA ACGAAATGAA ACCATCAGAG TTACTTGTCG    1920

ATGAAAATAC TTACAACTTT AGCAAAGCAG ACGAATTTGT AAATTTTGCA ACAAGTAACA    1980

ACATTGCCAT CAGAGGTCAT ACACTGGTTT GGCATGAGCA ACACCCGAC TGGTTTTCA      2040

AGGACACAAA TGGAAATACG TTGAGCAAGG ATGCATTGCT AAGCAGATTA AAACAGTATA    2100

TTTATACGGT AGTGGGAAGA TATAAAGGGA AGGTTTATGC ATGGGATGTG GTAAATGAAG    2160

CAATAGATGA AAGTCAAGGT GATGGATTCA GGAGATCTAA CTGGTACAAC ATTTGTAGTC    2220

CCGAATATAT TGAGAAGGCT TTTATATGGG CACATGAAGC CGATCCAGAC GCAAAATTGT    2280

TTTACAACGA TTACAACACA GAAAACAGTC AGAAGAGACA GTTTATTTAC AACATGATTA    2340

AGAGTCTCAA GGAAAAAGGT GTTCCAATTC ATGGAATAGG ATTGCAGAGT CATATAAATC    2400

TTGATTGGCC CTCGATTAGC GAGATAGAGA ACACCATAAG ATTGTTCAGC TCTATACCTG    2460

GATTGGAGAT ACACATTACG GAGCTTGATA TGAGTTTTTA TCAGTGGGGT TCGAGTACCA    2520

GTTACTCAAC GCCACCAAGA GATCTCCTGA TAAAACAGGC AATGAGATAT AAGGAGTTAT    2580

TTGATTTGTT TAAAAAGTAC AACAATGTAA TAACAAGTGT AACATTCTGG GGACTGAAGG    2640

ATGATTACTC ATGGCTGAGT CAAAACTTTG GAAAAGTGA TTACCCGTTG TTATTTGATG     2700

AAAACTATAA ATCAAAATAT GCCTTTTGGA GCCTGATTGA GCCAACTGTG ATACCGGCCA    2760

ACTCAACATT GCCAGCACCA CCAGCTATTC AAATACCTAC ACCAACTCCC ACACCAACCC    2820

CGACACCGAC AGTGAGTGCA ACGCCAACAC CAGCACCGAC GGCATCACCG GTAGGTGGCA    2880

GTTACTGGAC GCCGAGTGAG AGTTACAGTG CGCTGAAGGT ATGGTATGCG AATGGGAATT    2940

TAAGCAGCCC GACGAATGTA TTGAATCCTA AGATAAAGAT AGAGAATGTT GGACGACAG     3000

CGGTAGATCT TAGCAGGGTG AAGGTAAGAT ACTGGTACAC GATAGATGGT GAGGCAACAC    3060

AGAGTGTAAG TGTAACAAGC AGCATAGATC CTGCGTATAT AGATGTGAAG TTTGTGAAGC    3120

TTGGAGCGAA CGCAGGCGGA GCGGATTACT ATGTGGAGAT AGGCTTTAAG AGTGGAGCAG    3180

GGGTTTTGGC AGCAGGGCAA AGCACGAAGG AGATAAGACT TAGCATACAG AAGGGCAGTG    3240

GCAGCTACAA TCAGTCAAAT GACTATTCGG TGAGGAGTGC AACAGGCTAT ATAGAGAACG    3300

AGAAGGTAAC AGGGTATATA GATGATGTAC TTGTATGGGG AAGAGAGCCG AGCAGGAACG    3360

CCCAGATCAA GGTATGGTAT GCGAATGGGA ATTTAAGCAG CCCGACGAAT GTATTGAATC    3420

CTAAGATAAA GATAGAGAAT GTTGGGACGA CAGCGGTAGA TCTTAGCAGG GTGAAGGTAA    3480

GATACTGGTA CACGATAGAT GGTGAGGCAA CACAGAGTGT AAGTGTAACA AGCAGCATAA    3540

ACCCTGCGTA TATAGATGTG AAGTTTGTGA AGCTTGGAGC AAATGCAGGT GGAGCGGATT    3600

ACTATGTGGA GATAGGCTTT AAGAGTGGAG CAGGGGTTTT GGCAGCAGGG CAGAGCACGA    3660

AGGAGATAAG ACTTAGCATA CAGAAGGGCA GTGGCAGCTA CAATCAGTCA AATGACTATT    3720

CGGTGAGGAG TGCAACAGGC TATATAGAGA ACGAAGGTAA CGGGGTAT ATAGATGGTG      3780

CGATAGTGTG GGGAAGAGAG CCGAGCAGGG GTACAAAGCC GGCGGGAGTA GTAACACCGA    3840

CACCGGCACC GACCCCGACA TCGACGCCGA CACCAACACC TACAACCACA CCTGCACCGA    3900

CATCAGCCCC GACACCGAGC CCAACAGTGA CAGCAACGCC GACTCCAACG CCGACGCCGA    3960

CAGTGACGGT TACTGTGACT CCGACACCGA CACCAACACC GACGCCGACA CCGACAGGGA    4020

CACCTGGCAC GGGAAGTGGT TTGAAGGTAC TATACAAGAA CAATGAGACA AGTGCGAGCA    4080

CAAGTTCTAT AAGGCCGTGG TTTAAGATAG TGAATGGAGG CAGCAGCAGT GTTGATCTTA    4140

GCAGGGTTAA GATAAGATAC TGGTACACAG TGGATGGTGA CAAGCCACAG AGTGCGGTAT    4200
```

```
GTGACTGGGC ACAGATAGGG GCAAGCAATG TGACATTCAA TTTTGTGAAG CTGAGCAGCG    4260
GAGTGAGTGG AGCGGATTAT TACTTGGAGG TAGGATTTAG CAGTGGAGCT GGGCAGTTGC    4320
AGCCTGGTAA GGACACAGGG GATATACAGG TAAGGTTTAA CAAGAATGAC TGGAGCAATT    4380
ACAATCAGGC AGACGACTGG TCATGGTTGC AGAGCATGAC GAATTATGGA GAGAATGCGA    4440
AGGTAACGCT GTATGTAGAT GGTGTTCTGG TATGGGGCA GGAGCCGGGC GGAGCGACAC     4500
CTGCACCGAC AAGCACAGCA ACACCAACGC CAACTCCGAC AGCAACAGCA ACACCGACGC    4560
CGACAGCAAC GCCAACGTCT ACACCGACAC CGACAGCAAC ACCAACCCCA ATACCAACAC    4620
CCACAACGCC TCCTACAAAA CCGGTGGGTA AGATTCCACC AAATAACAAC CCGCTGATTT    4680
CACACAAGTT CGGTGCGGAC CCGGCAGTCC TTGTTTATGG TGGCAGAGTT TATATGTATC    4740
TTACAAATGA CATTCTGGAG TATGATGAAA ATGGAAATGT GAAGGATAAC TCATACAGCA    4800
AAATAAACAA AATAACAGTT ATATCATCGG ATGACCTTGT AAACTGGACA GACCATGGCG    4860
AGATTGAAGT TGCAGGTCCG AACGGGGTTG CAAAATGGGC AAGTCTTTCA TGGGCACCGG    4920
CTGTTGCATG CAAAAAGATT AACGGAAAAG ACAGGTTCTT CCTTTACTTT GGCAACAGCG    4980
GTGGTGGCAT AGGTGTAATA ACGGCAGACT CACCAACCGG TCCGTGGTCA GACCCGCTTG    5040
GAAGACCGCT TATCACATGG TCAACACCCG GTGTGCAGGG TGTTGTCTGG TTGTTTGACC    5100
CTGCAGTGCT GGTGGATGAT GACGGGAAAG CATATATTTA TTTTGGTGGA GGAGTTCCAC    5160
AGGGGCAGGA TGCTATGCCA AACACGGCAC GTGTGATGCA GCTGGGAGAT GATATGATAA    5220
GTGTTGTTGG GAGTGCTGTT ACAATTCCAG CACCATACAT GTTGAGGAT TCCGGGATAA     5280
ACAAGATAGG GAATACCTAC TATTACTCCT ACTGCACAAA CTTTGCACAA AGACCGCAGG    5340
GCAGCCCACC GGCGGGTGCT ATAGCGTACA TGACAGGCAG AAGTCCAATG GGACCCTGGG    5400
AATACCGCGG GGTTATACTC AGAAATCCGG GGAATTTCTT TGGAGTTGGT GGCAATAACC    5460
ATCACCAGCT GTTTGAATTT AATGGCAAAT GGTATATTGC ATACCACGCA CAGACACTTG    5520
CAAAAGATTT GGGAGTTGCA AAGGGTTACA GGTCACCGCA TATAAACTAT GTGCAGATTG    5580
AAAATGGTAC GATAAAAAAA GTAACAGCCG ACTACAAAGG AGTGGCACAG GTGAAGAATT    5640
TTGACCCGTA CAGGATGGTT GAGGCGGAGA CATTTGCATG GTGTGCAGGG ATTTCGACAA    5700
AGAAGGCAAA TGCGAGCAAT AATATGTGCT TGACAGGTAT AGACAGTGGA GACTGGATTG    5760
CACTTTCCAA GGTTGACTTT GGTAATGCAG GTCCACAGAA ATTTGAGGCG CAGGTTTCCA    5820
GCATCAACGG CAAAGGGTAT ATAGAACTCA GGATAGACTC GGTTGATGGT AGAACCATTG    5880
CAGTTGCAGA GGTTCTGCCA CAGAGTGGTT CTTCTTCGCA GTGGGTCAAA GTAGAGGCAA    5940
ATGTTGAGAA TGTAACAGGT GTGCATGATT TGTATCTTGT GTTCAGAGGT GAAAAGAAGA    6000
GCAACCTGTT TGACATGGAT TGGTGGAGAT TTGTGAGGTA AATAGCATTA GTCAACGCGA    6060
GATATTAATA CTGCTTTAGC AGTCAGTAAA TGAATGAATA AAGGAATTTT AGCGGGGTAG    6120
CACATCTATA GGAAAGATGT GCTGCTTCGC TAAAGTCCTA TATATGGGTG TTTCAAAAGT    6180
AGCACAAAAG ATAATTGGTT TTAACAGTCA AAATGTACAA GTAAAGTAA ACAAGCAGGA     6240
GGGGAGTTAG TGAAATGAAA AAGAGAGTTT TAAGGTTTGT TCCCGGTTA ATATTGGCAG     6300
TGTTTATTAT GAGCATAAGT TTAGTGGGAT CAATGAGTTA TTTTCCTGTA AAGACCGAAG    6360
CTGCACCTGA CTGGAGTATA CCGAGTTTAT GGGAGAGTTA TAAGAATGAT TTTAAGATAG    6420
GGGTAGCGAT ACCTGCGAGA TGTTTGAGCA ATGATACAGA CAAGCAAATG GTGTTGAAGC    6480
ATTTTAACAG TATTACAGCA GAGAATGAGA TGAAGCCTGA AAGTTTATTG GCGGGGCAGA    6540
CAAGCACGGG ATTGAGTTAC AGGTTTAGCA CAGCTGATAC GTTTGTTAAC TTTGCGAATA    6600
```

```
CGAACAATAT AGGGATTAGA GGGCATACAC TGGTATGGCA TAATCAAACA CCTGATTGGT   6660

TTTTTAGAGA CAGCAGTGGG CAGATGTTAT CGAAAGATGC ACTGTTAGCG AGGCTGAAGC   6720

AATACATTTA TGATGTTGTT GGCAGGTATA AGGGTAAGGT ATATGCATGG GACGTTGTAA   6780

ATGAGGCTAT AGATGAGAGT CAGCCTGATG GATATAGACG TTCGACATGG TATCAAATCT   6840

GTGGTCCGGA GTATATAGAG AAGGCATTCA TATGGGCGCA CGAAGCCGAT CCGAATGCGA   6900

AGCTGTTTTA TAATGACTAT AATACAGAGA TTTCAACAAA GAGAGATTTC ATATACAACA   6960

TGGTAAAGAA TTTAAAATCC AAGGGTGTGC CGATTCATGG TATAGGGATG CAGAGCCATA   7020

TAAACGTGAA CTGGCCATCG GTGAGTGAGA TAGAGAACAG TATAAAACTG TTTAGTTCGA   7080

TACCTGGGAT TGAGATTCAC ATTACAGAGC TTGACATGAG TTTATACAAC TATGGATCAA   7140

ACGAGAATTA TTCAACACCG CCGCAGGATT TGCTTCAGAG GCAGGCACAG AAGTACAAAG   7200

ATATATTTAC AATGCTGAGG AAATACAAAG GTATTGTAAC ATGTGTTACA TTCTGGGGTT   7260

TGAAGGATGA CTATTCATGG CTGAACTCAT CCAGTAAGAG GGATTGGCCG CTGTTGTTTT   7320

TTGATGATTA CAGTGCAAAG CCGGCGTATT GGTCGGTGAT TGAGGCAGCA GGTGCAAGTG   7380

CATCTCCAAG CCCGACAGTG ACAGCAACGC CGACGCCGAC TCCGACGCCG ACAGTGACTG   7440

TTACGGCGAC TCCGACACCG ACACCAACAG GGACACCTGG TACGGGAAGT GGTTTGAAGG   7500

TACTATACAA GAACAATGAG ACCAGTGCGA GCACAGGTTC TATAAGGCCG TGGTTTAAGA   7560

TAGTGAATGG AGGCAGCAGC AGTGTTGATC TTAGCAGGGT TAAGATAAGA TACTGGTACA   7620

CAGTGGATGG TGACAAGCCA CAGAGTGCGG TATGTGACTG GCACAGATA GGTGCAAGCA   7680

ATGTGACATT CAATTTTGTG AAGCTGAGCA GCGGAGTGAG TGGAGCGGAT TATTACTTGG   7740

AGGTAGGATT TAGCAGTGGA GCTGGGCAGT TGCAGCCTGG TAAGGACGCA GGGGATATAC   7800

AGGTAAGGTT TAACAAGAAT GACTGGAGCA ATTACAATCA GGCAGACGAC TGGTCATGGT   7860

TGCAGAGCAT GACGGATTAT GGAGAGAATG CGAAGGTGAC GCTGTATGTA GATGGTGTTC   7920

TGGTATGGGG GCAGGAGCCG GGAGGAGCGA CACCTGCACC GACAGCGACA GCAACACCAA   7980

CGCCAATTCC GACAGCAACA GTAACACCGA CGCCGACAGC AACTCCAACG TCTACACCGA   8040

GACCGACAGC GACAGCGACC CCGACACCGA CAGTGAGTGC AACGCCAACA CCGGCACCGA   8100

CGGCATCACC GGTAGGTGGC AGTTACTGGA CGCCGAGTGA GAGTTACGGT GCGCTGAAGG   8160

TATGGTATGC GAATGGGAAT TTAAGCAGCC CGACGAATGT ATTGAATCCT AAGATAAAGA   8220

TAGAGAATGT TGGGACGACA GCGGTAGATC TTAGCAGGGT GAAGGTAAGA TACTGGTACA   8280

CGATAGATGG TGAGGCAACA CAGAGTGTAA GTGTAGCGAG CAGCATAAAT CCTGCGTATA   8340

TAGATGTGAA GCTTGGAGCG AACGCAGGCG GAGCGGATTA CTATGTAGAG ATAGGGTTTA   8400

AGAGTGGAGC AGGTGTTTTG GCAGCAGGGC AGAGCACGAA GGAGATAAGA CTTAGCATAC   8460

AGAAGGGCAG TGGCAGCTAC AATCAGTCAA ATGACTATTC GGTGAGGAGT GCAACAGGCT   8520

ATATAGAGAA CGAGAAGGTA ACGGGGTATA TAGATGATGT ACTTGTATGG GGGAGAGAGC   8580

CGAGCAGGAA CGCCCAGATC AAGGTATGGT ATGCGAATGG GAATTTAAGC AGCCCGACGA   8640

ATGTATTGAA TCCTAAGATA AAAATAGAGA ATGTTGGGAC GACAGCGGTA GATCTTAGCA   8700

GGGTGAAGGT AAGATACTGG TACACGATAG ATGGTGAGGC AACACAGAGT GTAAGTGTAA   8760

CAAGCAGCAT AAATCCTGCG TATATAGATG TGAAGTTTGT GAAGCTTGGA GCAAATGCAG   8820

GCGGAGCGGA TTACTATGTA GAGATAGGGT TTAAGAGTGG AGCAGGTGTT TTGGCAGCAG   8880

GGCAGAGCAC GAAGGAGATA AGGCTTAGCA TACAGAAGGG CAGTGGCAGC TACAATCAGT   8940
```

```
CAAATGACTA TTCGATAAGA AGTGCGAATA GCTATATAGA GAACGAGAAG GTAACAGGGT    9000
ATATAGATGG TGCGATAGTG TGGGGAAGAG AGCCGAGCAG GGGTACAAAG CCGGCGGGAG    9060
TAGTAACACC GACACCGGCA CCGACCCCGA CATCGACGCC AACACCGATA CCTACAACCA    9120
CACCGACACC GACACCGACA CCGACTGTGA CGGTGACCCC AACTTCTACA CCCACACCGG    9180
TTTCATCATC CACTCCTACA CCAACAGCAA CGCCAACACC TACACCTTCT ATCACGATAA    9240
CACCAGCGCC AACTGCAACA CCCACTCCGA CTCCTTCTGT CACAGATGAT ACAAATGATG    9300
ATTGGTTATT TGCGCAGGGT AACAAAATAG TCGACAAGGA TGGCAAACCT GTATGGTTAA    9360
CAGGAGTTAA TTGGTTTGGA TTTAATACAG GAACGAATGT GTTTGATGGT GTGTGGAGTT    9420
GTAATCTTAA AAGTGCATTA GCTGAGATTG CAAACAGAGG ATTTAATTTG CTAAGAGTAC    9480
CGATTTCAGC AGAGCTGATT TTGAATTGGT CGAAAGGAAT TTATCCAAAA CCAAATATCA    9540
ATTATTATGT TAACCCTGAG TTAGAAGGTC TGACGAGTTT AGAGGTATTT GATTTTGTAG    9600
TAAAAACATG CAAAGAAGTT GGACTGAAAA TTATGTTGGA TATTCATAGT GCAAAAACTG    9660
ATGCGATGGG GCATATATAT CCGGTATGGT ATACAGATAC TATAACGCCA GAAGATTATT    9720
ATAAAGCATG TGAATGGATC ACAGAGAGAT ATAAAAATGA TGATACAATT GTAGCATTTG    9780
ATTTGAAGAA TGAGCCACAT GGTAAACCAT GGCAAGATAG TGTTTTTGCA AAATGGGACA    9840
ATTCAACAGA TATTAACAAC TGGAAATATG CAGCTGAGAC CTGTGCGAAG AGAATACTTG    9900
CAAAAAATCC AAACATGTTA ATAGTAATTG AAGGAATAGA AGCTTATCCA AAAGATGATG    9960
TTACGTGGAC TTCTAAATCA TCAAGTGACT ATTATTCTAC CTGGTGGGGC GGCAACTTAC   10020
GGGGTGTTAA AAAGTATCCA ATAAACCTTG GACAGTATCA GAACAAAGTG GTTTATTCAC   10080
CACATGATTA TGGACCATTG GTTTACCAGC AACCCTGGTT TTATCCTGGA TTTACCAAAG   10140
ATACGCTTTA CAATGATTGC TGGAGGGATA ATTGGACTTA TATTATGGAT AATGGGATAG   10200
CTCCGTTGCT CATTGGTGAA TGGGGTGGTT ACTTAGATGG TGGCGATAAT GAAAAGTGGA   10260
TGACTTATTT GAGAGATTAT ATTATAGAAA ACCATATTCA TCATACATTC TGGTGTTACA   10320
ATGCAAATTC TGGTGATACT GGAGGATTGG TGGGATATGA TTTTTCGACG TGGGATGAAC   10380
AGAAGTACAA TTTCTTAAAA CCAGCTTTAT GGCAGGATAG TAAAGGAAGA TTTGTTGGGC   10440
TTGATCACAA GAGACCACTG GGTACAAATG GAAGAATAT AAATATAACT ATTTATTACC   10500
AGAACGGTGA AAAACCGCCT GTCCCAAAGA ATTAATAAAT GGATGAATAC TTCTTTTGTA   10560
AATGTGATGG AGGCTACTCA AAGTTGATTT GGTAGCCTCT ATCTTTTTAA AAAAGTGGCT   10620
CTATAATAAA TATTATTGTG GGGAGAAAGG GAAAAATATA GCACTTATTC TGAATGCCTG   10680
CTAAATAGAA ACTGTTTTAT GACAAAAGAA CACTCAAAAA GAAAGGAGGC ATCCAGAATA   10740
AGTGCTTAAA TCTAATTATA TCACTGGACT TTTAAAATCG AAAGATATCA TTCTTCTTCA   10800
AATGGATGAG AATGAAAGTG AAATAGAACT TCACATAAGT TACAAGCAAG GTACATGATT   10860
ATCACACGCA GAAGGTAAAA GACATACCTA GACATACCTA TAATAATGGG CAAGAAAACA   10920
ATTTGATTAT AAGAAAGAGA AGATATGTCT GCAAAGCATG TGGGAAGAAG TTTTTTGACC   10980
ACATAAGTTT TATAGGCAAA TCTCAAAGGA TGACAAATAG ACTTGCAGCA TATATTATAA   11040
GTCAACTTGG AAGTTTAACA AGTATGAAAG AGATAGCAAA ACACACAAAT GTTTCAGATG   11100
TAGCAGTTAT GAGATTGTTT GATAAAGTAA ACCCTGGTCA AACTCTAGAT GAGTTTTCTT   11160
CTGAAGCAAT ATGGGCAGAA TAGTTTAAAG GCAATGCTTT TGCAAATTTC TGATGCACTT   11220
AAAAAAATGA CAGATTCCAT GCAAAAGTTC AAAGATTATT TTGAAGGATA CAAAAACACA   11280
AATGTATTCT ATGTGCCACC CGGGGCTTTT GAAAGCAGTA ATTTTGAAAA AGCACTGGAT   11340
```

```
TCATACATGG ATAAGAGCAG AAAAATAACA AAAATTATCC TTATCCTTGA CACCAATCCT    11400

TATACAAACA AAGCAATAGA TATTGTTGAC AGTGTTGAAA AGGTATTGAA AAACTCTTTG    11460

GAGTTTGTTG ATACAAAATT CACTGAATTT GGTGTTGGCG AATATCGTC  AAGCAATCAC    11520

GATTTGAGAA GCATCTATTT TAAAGATTTT AGGACTTTGA GACTCATAAT GATAATTAGC    11580

ATTTTGCTTT TGATGTTCAT AATTTCAAGA TCAATATTCA ATGCGGCAGC GGTTGTGGCA    11640

ATAGTTTTTA TTGATTACTA CCTTGCACTT TCTATTACAG ATGATTTT   CAAAGGTATT    11700

TTCAATT                                                             11707

(2) INFORMATION FOR SEQ ID NO: 2:

(i) SEQUENCE CHARACTERISTICS:
        (A) LENGTH: 6416 base pairs
        (B) TYPE: nucleic acid
        (C) STRANDEDNESS: single
        (D) TOPOLOGY: linear (xi) SEQUENCE DESCRIPTION: SEQ ID NO: 2:

GTCGACACTT GACTGRRGCG GGCAGCCGGA TACATGGAAT GGGACATATA CGGGCAATCC      60

AAATCTGCAT GTGAAGATAG TGGATTATGG AACAGATTTG GGTATAACTG CATCACTTGC    120

GAATGCGCTT TTGTACTACA GTGCGGCGAC GAANGAGTAT GGAGTATCTG ATGAGGCAGC    180

GAANAATTTA GCGAAAGAGC TGCTGGACAG GATGTGAAAC TTATACAGGG ATGACAAGGG    240

CTTGTCGGCA CCCGAGAAGA GAGGAGATTA CAAGAGGTTC TTTGAGCAAG AGGTATACAT    300

TCCAGCGGGC TGGACAGGGA AGATGCCGAA TGGAGATGTA ATAAAGAGTG GAGTGAAGTT    360

TATAGACATA AGGAGCAAGT ACAAACAGGA TCCTGACTGG CAGAAGCTGG TTTCGGCATA    420

CAATGCAGGA GAGGCACCGG AGTTCAGGTA TCACAGATTC TGGGCACAGT GTGATATAGC    480

AATTGCCAAT GCAACATATG AAATCCTGTT CGGCAATCGA TAAGTCAAAA GTGGGTGTGT    540

GAAAGATATT AGGAAGGGAA GTAGCACCGC TCTGTGCTAC TTCCCCAATT TGAAAAGTTA    600

AATAAAAACA AAGTTAATTA AGAGAGGGGT AGGATGCAAG AAATGAAAGC AATTAAGAGG    660

GTTGTCTCGA TAACTGCTCT ACTTGTTTTG ACACTTTCAT TATGTTTTCC TGGTATCATG    720

CCTGTGAAAG CTTATGCAGG GGGAACATAT AATTACGGTG AGGCACTACA GAAAACAATA    780

ATGTTCTATG AATTCCAGAT GTCAGGGAAA CTACCTTCCT GGGTAAGGAA CAACTGGAGA    840

GGTGACTCTG GCTTAGATGA TGGCAAGGAT GTAGGGCTTG ATTTAACAGG TGGCTGGCAT    900

GACGCAGGTG ATCACGTAAA GTTTAACCTG CCAATGTCGT ATAGCGCCTC AATGCTGGGG    960

TGGGCTGTTT ATGAATATAA GGATGCATTT GTAAAGAGCA AACAATTGGA GCACATTTTA   1020

AATCAAATAG AGTGGGCAAA TGACTACTTT GTGAAGTGTC ATCCATCAAA ATATGTATAC   1080

TATTATCAGG TTGGTGATCC AACTGTAGAT CACAATTTTT GGGACCTGC  AGAAGTAATG   1140

CAAATGAAAC GTCCAGCGTA TAAGTGTGAT TTATCAAACC CAGCATCTTC TGTAGTGGCA   1200

GAAACAGCTG CATCACTTGC GGTGGCTTCA GTTGTAATAA AGGAAAGAAA TTCTCAGAAA   1260

GCAGCTTCTT ATCTCCAACA TGCCAAAGAC CTGTTTGAAT TTGCCGATAC CACAAGAAGT   1320

GATGCGGGGT ATACTGCTGC AACAGGTTTC TACACATCGG GTGGTTTTAT TGATGACCTT   1380

GGATGGGCTG CTGTATGGCT TTATATTGCG ACAAATGACA GTAGTTATTT GACGAAAGCT   1440

GAAGAGTTGA TGTCAGAATA TGCTAATGGT ACTAATACAT GGACACAATG CTGGGATGAT   1500

GTTCGATATG GAACATTGAT CATGCTTGCA AAGATTACAG GGAAAGAGTT ATATAAAGGA   1560

GCTGTGGAAA GAAACTTAGA CCATTGGACT GACAGAATTA CGTATACGCC GAAAGGGATG   1620
```

-continued

```
GCATATCTGA CAGGATGGGG TTCATTAAGA TATGCGACAA CAGCTGCATT TTTAGCATGT   1680

GTCTATGCAG ACTGGTCAGG GTGCGATTCG AACAAAAAGA CCAAATATTT GAACTTTGCA   1740

AAAAGCCAGA TTGACTATGC ACTGGGTTCC ACAGGTAGAA GTTTTGTAGT AGGATTTGGC   1800

ACCAATTATC CACAACATCC GCATCACAGG AATGCGCATA GTTCATGGGC TAACAGCATG   1860

AAAATACCAG AGTATCACAG ACACATATTA TATGGAGCAC TGGTTGGTGG TCCTGGTAGT   1920

GATGATAGTT ATAATGATGA CATTACCGAT TATGTACAAA ATGAGGTTGC CTGCGATTAT   1980

AATGCTGGAA TTGTTGGTGC ACTGGCAAAG ATGTACCAGT TATATGGAGG TGAACCTATT   2040

GATGATTTTA AAGCAATTGA AACACCCACA AATGATGAAA TTTTTGTTGA ATCAAAATTT   2100

GGGAATTCAC AGGGTCCAAA TTATACCGAA GTAATTTCCT ATATCTATAA TCGAACAGGA   2160

TGGCCACCAA GGGTAACTGA TAAACTAAGT TTTAAATATT TTATAGACCT AACCGAATTA   2220

ATCCAGGCAG GGTATTCGCC TGATGTTGTC AAAGTTGACA CATACTACAT CGAAGGAGGT   2280

AAAATTAGCG GTCCTTACGT ATGGGACAAA ATAGGAATA TATACTATGT TCTTGTGGAT   2340

TTTAGTGGAA CCAAGATATA TCCTGGCGGT GAAGTTGAAC ACAAAAAGCA GGCTCAATTT   2400

AAAATATCTG TTCCGCAGGG GTATCCATGG GATCCTACCA ATGATCCTTC ATATAAGGGA   2460

TTAACCAGTC AATTAGAAAA GAATAAATAT ATTGCCGCAT ATGATAATAA TAATCTGGTA   2520

TGGGGTTTAG AGCCGGGTGC GGCAACATCC ACACCTGCAC AACATCAAC ACCAACACCA   2580

ACCCCGACCC CAACACCAAC AGTGACAGCA ACGCCGACGC CGACTCCTAC ACCGACACCG   2640

ACGGGGTCAC CTGGTACGGG AAGTGGTGTG AAGGTACTGT ACAAGAACAA TGAGACAAGT   2700

GCGAGCACAC GTTCTATAAG GCCGTGGTTT AAGATAGTGA ATGGAGGCAG CAGCAGTGTT   2760

GATCTTAGCA GGGTTAAGAT AAGATACTGG TACACAGTGG ATGGTGACAA GCCACAGAGT   2820

GCGGTATGTG ACTGGGCACA GATAGGGGCA AGCAATGTGA CATTCAATTT TGTGAAGCTT   2880

AGCAGCGGAG TGAGTGGAGC GGATTATTAC CTGGAGGTAG GATTTAGCAG TGGAGCTGGG   2940

CAGTTGCAGC CTGGTAAGGA CACAGGGGAT ATACAGGTAA GGTTTAACAA GAATGACTGG   3000

AGCAATTACA ATCAGGCAGA CGACTGGTCA TGGTTGCAGA GCATGACGAA TTATGGAGAG   3060

AATGCGAAGG TGACGCTGTA TGTAGATGGT GTTCTGGTAT GGGGGCAGGA GCCGGGAGGA   3120

GCGACACCTG CACCGACAAG CACAGCAACA CCAACGCCAA CTCCGACAGC AACCCCAACA   3180

CCTACACCTA CACCGACCCC GACACCGACA GTGAGTGCAA CGCCAACACC GGCACCGACG   3240

GCATCACCGG TAGGTGGCAG TTACTGGACG CCGAGTGAGA GTTACGGTGC GCTGAAGGTA   3300

TGGTATGCGA ATGGGAATTT AAGCAGCCCG ACGAATGTAT TGAATCCTAA GATAAAGATA   3360

GAGAATGTTG GGACGACAGC GGTAGATCTT AGCAGGGTGA AGGTAAGATA CTGGTACACG   3420

ATAGATGGTG AGGCGACACA GAGTGTAAGT GTAGCGAGCA GCATAAATCC TGCGTATATA   3480

GATGTGAAGT TTGTGAAGCT TGGAGCGAAC GCAGGCGGAG CGGATTACTA TGTGGAGATA   3540

GGCTTTAAGA GTGGAGCAGG TGTTTTGGCA GCAGGGCAGA GCACGAAGGA GATAAGGCTT   3600

AGCATACAGA AGGGCAGTGG CAGCTACAAT CAGTCAAATG ACTATTCGGT AAGGAGTGCG   3660

AATAGCTATA TAGAGAACGA GAAGGTAACA GGGTATATAG ATGATGTACT TGTATGGGGA   3720

AGAGAGCCGG GCAGGAACGC CCAGATCAAG GTATGGTATG CGAATGGGAA TTTAGGCAGC   3780

ATGACGAATG TATTGAATCC TAAGATAAAG ATAGAGAATG TTGGGACGAC AGCGGTAGAT   3840

CTTAGCAGGG TGAAGGTAAG ATACTGGTAC ACGATAGATG GTGAGGCGAC ACAGAGTATA   3900

AGTGTAACAA GCAGCATAAA TCCTGCGTAT ATAGATGTGA AGTTTGTGAA GCTTGGAGCA   3960
```

```
AATGCAGGTG GAGCGGATTA CTATGTGGAG ATAGGGTTTA AGAGTGGAGC AGGTGTTTTG    4020

GCAGCAGGGC AGAGCACGAA GGAGATAAGG CTTAGCATAC AGAAGGGCAG TGGCAGCTAC    4080

AATCAGTCAA ATGACTATTC GGTAAGAAGT GCGACAGGCT ATATAGAGAA CGAGAAGGTA    4140

ACAGGGTATA TAGATGGTGC GATAGTGTGG GGAAGAGAGC CGAGCAGGGG TACAAAGCCG    4200

GCGGGAGGAG TGACACCGAC ACCGGCACCG ACGCCGACAT CGACGCCAAC ACCAACACCT    4260

ACAACCACAC CGACACCGAC ACCGACTGTG ACGGTGACCC CAACTCCTAC ACCTGCGGTA    4320

ACCCCCGATG TTAAAATATC GATCGATACG TCCAGGGGAA GAACAAAGAT AAGCCCGTAT    4380

ATTTATGGAG CAAATCAGGA TATCCAGGGT GTTGTTCACC CTGCAAGACG ACTTGGTGGG    4440

AACAGATTGA CGGGTTACAA TTGGGAGAAC AATATGTCCA ATGCAGGGAG TGACTGGTAT    4500

CATTCAAGCG ATGATTATAT GTGTTATATT ATGGGTATAA CAGGGAATGA TAAGAACGTT    4560

CCAGCAGCTG TTGTAAGCAA ATTTCACGAG CAGTCAATAA AGCAAAATGC ATATTCAGCC    4620

ATCACATTAC AGATGGTAGG TTATGTGGCA AAGGATGGGA ATGGTACAGT GAGCGAGTCA    4680

GAGACAGCTC CGTCGCCGAG ATGGGCTGAG GTCAAGTTTA AAAAAGATGG TGCACTGTCA    4740

TTGCAGCCTG ACGTGAATGA TAACTATGTA TATATGGATG AGTTTATTAA CTATCTGATT    4800

AATAAGTATG GTCGATCATC GTCTGCAACG GGAATTAAAG GATATATACT TGACAACGAG    4860

CCGGACTTAT GGTTTACTAC TCATCCGCGA ATTCATCCAC AGAAGGTAAC CTGCAGTGAA    4920

TTGATAAATA AATCGGTGGA GCTGGCGAAA GTAATAAAGA CACTTGATCC AGATGCAGAA    4980

ATTTTTGGAC CTGCATCGTA TGGTTTTGTG GGATATTTAA CATTGCAGGA TGCACCTGAC    5040

TGGAATCAGG TTAAAGGAAA TCACAGATGG TTTTTGAGCT GGTACCTTGA GCAGATGAAG    5100

AAAGCATCGG ATAGTTTTGG GAARAGGTTA TTGGATGTAC TTGACATACA CTGGTACCCG    5160

GAGGCGCAGG TTGGCGGTGT GCGAATATGC TTTGACGGTG AAAATAGTAC TTCAAGGGAT    5220

GTGGCAATAG CGAGGATGCA GGCACCGAGA ACGCTATGGG ATCCGACATA TAAAACCACC    5280

CAGAAAGGTC AGATAACAGC GGGAGAAAAT AGCTGGATAA ACCAATGGTT TCCAGAGTAT    5340

CTTCCACTGC TTCCCAATAT AAAGGCAGAT ATAGACAAGT ATTATCCTGG TACCAAACTT    5400

GCTATAACTG AGTTTGATTA TGGAGGGAAG GACCATATAT CGGGAGGAAT AGCTTTAGCA    5460

GATGTGTTAG GGATATTCGG CAAGTATGGA GTATACATGG CAGCAAGATG GGGAGATTCG    5520

GGGAGCTATG CACAGGCGGC GTACAACATT TATCTCAACT ATGATGGGAA AGGTTCGAGA    5580

TACGGTTCAA CGTGTGTGAG CGCTGAGACA ACTGACGTTG AGAACATGCC GGTATATGCT    5640

TCAATTGAGG GAGAAGATGA TTCGACTGTG CATATTATAT TAATTAACAG GAATTATGAC    5700

AGGAAACTGA AGGCAGAGAT AAAGATGAAT AATACCAGGG TATACACAGG TGGAGAGATA    5760

TACGGATTTG ACAGTACAAG CTCTCAGATC AGGAAGATGG GAGTGCTCAG TAATATACAA    5820

AACAACACAA TCACCATAGA AGTTCCAAAT CTGACGGTAT ACCATATTGT TTTAACTTCT    5880

TCAAAGTAGA TTAAAGAATA AAAATGGAGA CACTGCTGCA TGGTAAAAGT TGAGATGTGC    5940

AGCAGTGTCT CATAATCACT AATCTAATAC AGTTAGAGAT GTTAAATTAT AAAACAGACG    6000

ATAACTTTGT TTTAAATGAT TGNNAGTCGG ANTTCTNNTG ATTAAAACAT NAGAAANTTG    6060

TNATANTNGA CTTTAATTNT NGCNNATAAA CGTAAATGGA TTCAATNACN WTACRATTTN    6120

CRTAATCTAW AAGRAGCACA GAGAAATATT ACATAGGAGG ATGTATCAAT AAATGATAGA    6180

TAAAAAGATA ATTGCTGTTA CAATTTTART AATGGTAACA TACTTTTTAG TACAAATATC    6240

RACTATAGGT GCACGGAATA TACCAGAGAC ATANTGGATA CCGCTGGATA TAGATACAAT    6300

AAGTATTGAC CTGGGCWAGN AGCCATATGT GANAGAATTT ATAGTATATT TTGGATATGG    6360
```

CGGAGGCAAA ATAGASTGTC WGTTTTATAG AGACAATACT TTGGCATTMT ACATCA        6416

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 3:

CCTTTATGAA TTCATTTACT GACTGCTA        28

(2) INFORMATION FOR SEQ ID NO: 4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 4:

CTTCCCTCGA GAATTCACAC ACCCACTTTT G        31

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 5:

TACCCCTCGA GAATTCCTAT TTACTCATTA        30

(2) INFORMATION FOR SEQ ID NO: 6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 6:

CTACACCCAT GGTAACCCCC GATGTTAA        28

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 7:

AAATGCTCGA GTAAAAGTGA ACAAGCA        27

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 8:

```
ATGTGTCCAT GGCATTAATT ATTTTTGTTG                                    30
```

(2) INFORMATION FOR SEQ ID NO: 9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 9:

```
ATGCAAGGCA TGCAAGCAAT TAAGAGGGTT G                                  31
```

(2) INFORMATION FOR SEQ ID NO: 10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 10:

```
TCAACAAAGA TCTAATCATT TGTGGGTGTT TC                                 32
```

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 11:

```
GTGCAGCTCG AGCTCCTCCC GGCTCCTGCC CCCA                               34
```

(2) INFORMATION FOR SEQ ID NO: 12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 12:

```
GAGGAACGGT CATATGAAGG TATGGTATGC GAATGGGAA                          39
```

(2) INFORMATION FOR SEQ ID NO: 13:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 13:

```
GAGGAGGAGC ATGCAGATCA AGGTATGGTA TGCGAATG                           38
```

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 14:

```
TTTAGCATGC TGAGGAAATA CAAAG                                         25
```

(2) INFORMATION FOR SEQ ID NO: 15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 15:

```
AGTTAGTGGC ATGCAAAAGA GAGTTTTAAG G                                31
```

(2) INFORMATION FOR SEQ ID NO: 16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 16:

```
GAAGTATGGA TCCATTTATT AATTCTTTGG G                                31
```

(2) INFORMATION FOR SEQ ID NO: 17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 17:

```
TACAATTTTA GCCATGGTAA CATACTTTTT AG                               32
```

(2) INFORMATION FOR SEQ ID NO: 18:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 18:

```
GCAGCAGTGT CGACATTTTT ATTCTTTAAT CTAC                             34
```

(2) INFORMATION FOR SEQ ID NO: 19:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 19:

```
GTGGATGAGA TCTAACCCGG CTCTAAACCC CA                               32
```

(2) INFORMATION FOR SEQ ID NO: 20:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 20:

```
TTGAACTTCC CCATGGCAGA ATTTTTACAA ATTGG                            35
```

(2) INFORMATION FOR SEQ ID NO: 21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 21:

```
TGTATCCCAT GCCGTCTT                                              18
```

(2) INFORMATION FOR SEQ ID NO: 22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 22:

```
CAAAAAGCAA TTATGTTTTA TGAATT                                     26
```

(2) INFORMATION FOR SEQ ID NO: 23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 23:

```
TGGTGCTGGC AATGTTGAGT TGGC                                       24
```

(2) INFORMATION FOR SEQ ID NO: 24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 24:

```
TCGGTAGTGC CACTTTCAAA TCCA                                       24
```

(2) INFORMATION FOR SEQ ID NO: 25:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 25:

```
CAAAGCAGAC GAATCTGTGC GTGGTATGCA ATATAC                          36
```

(2) INFORMATION FOR SEQ ID NO: 26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 26:

```
AGCTGAGCAG CGGAGTGA                                              18
```

(2) INFORMATION FOR SEQ ID NO: 27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 27:

TCCACTCACT CCGCTGCT                                                  18

(2) INFORMATION FOR SEQ ID NO: 28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 28:

GTTCTGATAC TGTCCAAG                                                  18

(2) INFORMATION FOR SEQ ID NO: 29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 29:

ACAGGCGGCG TACAACAT                                                  18

(2) INFORMATION FOR SEQ ID NO: 30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 30:

TTGAGGGATA TGGTGACC                                                  18

(2) INFORMATION FOR SEQ ID NO: 31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 31:

GAGAAACATA TCCTGCAA                                                  18

(2) INFORMATION FOR SEQ ID NO: 32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 32:

CCCATTTTAT ACCCAGGC                                                  18

(2) INFORMATION FOR SEQ ID NO: 33:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO: 33:

TCTTGAGCAG CCATTGGA                                                      18

(2) INFORMATION FOR SEQ ID NO: 34:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 34:

GATGGCCAGT TCACGTTTAT ATGG                                               24

(2) INFORMATION FOR SEQ ID NO: 35:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 35:

AGCACTGGTT GGTGGTCCTG GTAG                                               24

(2) INFORMATION FOR SEQ ID NO: 36:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 36:

GATTGACGGG TTACAATTGG GAGAAC                                             26

(2) INFORMATION FOR SEQ ID NO: 37:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO: 37:

AGWGCACCNA CAAATCCGGC ATTGTARTC                                          29

(2) INFORMATION FOR SEQ ID NO: 38:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO: 38:

CTCCAGAATG TCATTTGTAA GATACAT                                            27

(2) INFORMATION FOR SEQ ID NO: 39:

(i) SEQUENCE CHARACTERISTICS:
           (A) LENGTH: 35 base pairs
           (B) TYPE: nucleic acid
           (C) STRANDEDNESS: single
           (D) TOPOLOGY: linear (ii) MOLECULE TYPE: Other (xi) SEQUENCE DESCRIPTION: SEQ ID NO: 39:

GGGAATTCCA TATGGCGGCG TATAATTACG GTGAG                                          35

(2) INFORMATION FOR SEQ ID NO: 40:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: Other (xi) SEQUENCE DESCRIPTION: SEQ ID NO: 40:

TATTATTATC ATATGCGGC                                                            19

(2) INFORMATION FOR SEQ ID NO: 41:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: Other (xi) SEQUENCE DESCRIPTION: SEQ ID NO: 41:

CCAGAGTATC ACAGACAC                                                             18

(2) INFORMATION FOR SEQ ID NO: 42:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: Other (xi) SEQUENCE DESCRIPTION: SEQ ID NO: 42:

CCTGGATCCC TACGCTCCTC CCGGCTC                                                   27

(2) INFORMATION FOR SEQ ID NO: 43:

(i) SEQUENCE CHARACTERISTICS:
           (A) LENGTH: 1426 amino acids
           (B) TYPE: amino acid
           (C) STRANDEDNESS: single
           (D) TOPOLOGY: linear (ii) MOLECULE TYPE: None (xi) SEQUENCE DESCRIPTION: SEQ ID NO: 43:

Met Lys Lys Arg Val Leu Arg Phe Val Ser Arg Leu Ile Leu Ala Val
 1               5                  10                  15

Phe Ile Met Ser Ile Ser Leu Val Gly Ser Met Ser Tyr Phe Pro Val
                20                  25                  30

Lys Thr Glu Ala Ala Pro Asp Trp Ser Ile Pro Ser Leu Trp Glu Ser
            35                  40                  45

```
Tyr Lys Asn Asp Phe Lys Ile Gly Val Ala Ile Pro Ala Arg Cys Leu
 50                  55                  60

Ser Asn Asp Thr Asp Lys Gln Met Val Leu Lys His Phe Asn Ser Ile
 65                  70                  75                  80

Thr Ala Glu Asn Glu Met Lys Pro Glu Ser Leu Leu Ala Gly Gln Thr
                 85                  90                  95

Ser Thr Gly Leu Ser Tyr Arg Phe Ser Thr Ala Asp Thr Phe Val Asn
                100                 105                 110

Phe Ala Asn Thr Asn Asn Ile Gly Ile Arg Gly His Thr Leu Val Trp
                115                 120                 125

His Asn Gln Thr Pro Asp Trp Phe Arg Asp Ser Ser Gly Gln Met
    130                 135                 140

Leu Ser Lys Asp Ala Leu Leu Ala Arg Leu Lys Gln Tyr Ile Tyr Asp
145                 150                 155                 160

Val Val Gly Arg Tyr Lys Gly Lys Val Tyr Ala Trp Asp Val Val Asn
                165                 170                 175

Glu Ala Ile Asp Glu Ser Gln Pro Asp Gly Tyr Arg Arg Ser Thr Trp
                180                 185                 190

Tyr Gln Ile Cys Gly Pro Glu Tyr Ile Glu Lys Ala Phe Ile Trp Ala
                195                 200                 205

His Glu Ala Asp Pro Asn Ala Lys Leu Phe Tyr Asn Asp Tyr Asn Thr
    210                 215                 220

Glu Ile Ser Thr Lys Arg Asp Phe Ile Tyr Asn Met Val Lys Asn Leu
225                 230                 235                 240

Lys Ser Lys Gly Val Pro Ile His Gly Ile Gly Met Gln Ser His Ile
                245                 250                 255

Asn Val Asn Trp Pro Ser Val Ser Glu Ile Glu Asn Ser Ile Lys Leu
                260                 265                 270

Phe Ser Ser Ile Pro Gly Ile Glu Ile His Ile Thr Glu Leu Asp Met
                275                 280                 285

Ser Leu Tyr Asn Tyr Gly Ser Asn Glu Asn Tyr Ser Thr Pro Pro Gln
    290                 295                 300

Asp Leu Leu Gln Arg Gln Ala Gln Lys Tyr Lys Asp Ile Phe Thr Met
305                 310                 315                 320

Leu Arg Lys Tyr Lys Gly Ile Val Thr Cys Val Thr Phe Trp Gly Leu
                325                 330                 335

Lys Asp Asp Tyr Ser Trp Leu Asn Ser Ser Lys Arg Asp Trp Pro
                340                 345                 350

Leu Leu Phe Phe Asp Asp Tyr Ser Ala Lys Pro Ala Tyr Trp Ser Val
                355                 360                 365

Ile Glu Ala Ala Gly Ala Ser Ala Ser Pro Ser Pro Thr Val Thr Ala
    370                 375                 380

Thr Pro Thr Pro Thr Pro Thr Pro Thr Val Thr Val Thr Ala Thr Pro
385                 390                 395                 400

Thr Pro Thr Pro Thr Gly Thr Pro Gly Thr Gly Ser Gly Leu Lys Val
                405                 410                 415

Leu Tyr Lys Asn Asn Glu Thr Ser Ala Ser Thr Gly Ser Ile Arg Pro
                420                 425                 430

Trp Phe Lys Ile Val Asn Gly Ser Ser Ser Val Asp Leu Ser Arg
    435                 440                 445

Val Lys Ile Arg Tyr Trp Tyr Thr Val Asp Gly Asp Lys Pro Gln Ser
    450                 455                 460

Ala Val Cys Asp Trp Ala Gln Ile Gly Ala Ser Asn Val Thr Phe Asn
```

```
465                 470                 475                 480
    Phe Val Lys Leu Ser Ser Gly Val Ser Gly Ala Asp Tyr Tyr Leu Glu
                        485                 490                 495
    Val Gly Phe Ser Ser Gly Ala Gly Gln Leu Gln Pro Gly Lys Asp Ala
                    500                 505                 510
    Gly Asp Ile Gln Val Arg Phe Asn Lys Asn Asp Trp Ser Asn Tyr Asn
                515                 520                 525
    Gln Ala Asp Asp Trp Ser Trp Leu Gln Ser Met Thr Asp Tyr Gly Glu
            530                 535                 540
    Asn Ala Lys Val Thr Leu Tyr Val Asp Gly Val Leu Val Trp Gly Gln
    545                 550                 555                 560
    Glu Pro Gly Gly Ala Thr Pro Ala Pro Thr Ala Thr Ala Thr Pro Thr
                        565                 570                 575
    Pro Ile Pro Thr Ala Thr Val Thr Pro Thr Pro Thr Ala Thr Pro Thr
                    580                 585                 590
    Ser Thr Pro Arg Pro Thr Ala Thr Ala Thr Pro Thr Pro Thr Val Ser
                595                 600                 605
    Ala Thr Pro Thr Pro Ala Pro Thr Ala Ser Pro Val Gly Gly Ser Tyr
            610                 615                 620
    Trp Thr Pro Ser Glu Ser Tyr Gly Ala Leu Lys Val Trp Tyr Ala Asn
    625                 630                 635                 640
    Gly Asn Leu Ser Ser Pro Thr Asn Val Leu Asn Pro Lys Ile Lys Ile
                        645                 650                 655
    Glu Asn Val Gly Thr Thr Ala Val Asp Leu Ser Arg Val Lys Val Arg
                    660                 665                 670
    Tyr Trp Tyr Thr Ile Asp Gly Glu Ala Thr Gln Ser Val Ser Val Ala
                675                 680                 685
    Ser Ser Ile Asn Pro Ala Tyr Ile Asp Val Lys Leu Gly Ala Asn Ala
            690                 695                 700
    Gly Gly Ala Asp Tyr Tyr Val Glu Ile Gly Phe Lys Ser Gly Ala Gly
    705                 710                 715                 720
    Val Leu Ala Ala Gly Gln Ser Thr Lys Glu Ile Arg Leu Ser Ile Gln
                        725                 730                 735
    Lys Gly Ser Gly Ser Tyr Asn Gln Ser Asn Asp Tyr Ser Val Arg Ser
                    740                 745                 750
    Ala Thr Gly Tyr Ile Glu Asn Glu Lys Val Thr Gly Tyr Ile Asp Asp
                755                 760                 765
    Val Leu Val Trp Gly Arg Glu Pro Ser Arg Asn Ala Gln Ile Lys Val
            770                 775                 780
    Trp Tyr Ala Asn Gly Asn Leu Ser Ser Pro Thr Asn Val Leu Asn Pro
    785                 790                 795                 800
    Lys Ile Lys Ile Glu Asn Val Gly Thr Thr Ala Val Asp Leu Ser Arg
                        805                 810                 815
    Val Lys Val Arg Tyr Trp Tyr Thr Ile Asp Gly Glu Ala Thr Gln Ser
                    820                 825                 830
    Val Ser Val Thr Ser Ser Ile Asn Pro Ala Tyr Ile Asp Val Lys Phe
                835                 840                 845
    Val Lys Leu Gly Ala Asn Ala Gly Gly Ala Asp Tyr Tyr Val Glu Ile
            850                 855                 860
    Gly Phe Lys Ser Gly Ala Gly Val Leu Ala Ala Gly Gln Ser Thr Lys
    865                 870                 875                 880
    Glu Ile Arg Leu Ser Ile Gln Lys Gly Ser Gly Ser Tyr Asn Gln Ser
                        885                 890                 895
```

```
Asn Asp Tyr Ser Ile Arg Ser Ala Asn Ser Tyr Ile Glu Asn Glu Lys
            900                 905                 910

Val Thr Gly Tyr Ile Asp Gly Ala Ile Val Trp Gly Arg Glu Pro Ser
        915                 920                 925

Arg Gly Thr Lys Pro Ala Gly Val Val Thr Pro Thr Pro Ala Pro Thr
        930                 935                 940

Pro Thr Ser Thr Pro Thr Pro Ile Pro Thr Thr Thr Pro Thr Pro Thr
945                 950                 955                 960

Pro Thr Pro Thr Val Thr Val Thr Pro Thr Ser Thr Pro Thr Pro Val
                965                 970                 975

Ser Ser Ser Thr Pro Thr Pro Thr Ala Thr Pro Thr Pro Thr Pro Ser
            980                 985                 990

Ile Thr Ile Thr Pro Ala Pro Thr Ala Thr Pro Thr Pro Thr Pro Ser
            995                 1000                1005

Val Thr Asp Asp Thr Asn Asp Asp Trp Leu Phe Ala Gln Gly Asn Lys
        1010                1015                1020

Ile Val Asp Lys Asp Gly Lys Pro Val Trp Leu Thr Gly Val Asn Trp
1025                1030                1035                1040

Phe Gly Phe Asn Thr Gly Thr Asn Val Phe Asp Gly Val Trp Ser Cys
            1045                1050                1055

Asn Leu Lys Ser Ala Leu Ala Glu Ile Ala Asn Arg Gly Phe Asn Leu
            1060                1065                1070

Leu Arg Val Pro Ile Ser Ala Glu Leu Ile Leu Asn Trp Ser Lys Gly
            1075                1080                1085

Ile Tyr Pro Lys Pro Asn Ile Asn Tyr Val Asn Pro Glu Leu Glu
            1090                1095                1100

Gly Leu Thr Ser Leu Glu Val Phe Asp Phe Val Val Lys Thr Cys Lys
1105                1110                1115                1120

Glu Val Gly Leu Lys Ile Met Leu Asp Ile His Ser Ala Lys Thr Asp
                1125                1130                1135

Ala Met Gly His Ile Tyr Pro Val Trp Tyr Thr Asp Thr Ile Thr Pro
            1140                1145                1150

Glu Asp Tyr Tyr Lys Ala Cys Glu Trp Ile Thr Glu Arg Tyr Lys Asn
            1155                1160                1165

Asp Asp Thr Ile Val Ala Phe Asp Leu Lys Asn Glu Pro His Gly Lys
            1170                1175                1180

Pro Trp Gln Asp Ser Val Phe Ala Lys Trp Asp Asn Ser Thr Asp Ile
1185                1190                1195                1200

Asn Asn Trp Lys Tyr Ala Ala Glu Thr Cys Ala Lys Arg Ile Leu Ala
            1205                1210                1215

Lys Asn Pro Asn Met Leu Ile Val Ile Glu Gly Ile Glu Ala Tyr Pro
            1220                1225                1230

Lys Asp Val Thr Trp Thr Ser Lys Ser Ser Ser Asp Tyr Tyr Ser
            1235                1240                1245

Thr Trp Trp Gly Gly Asn Leu Arg Gly Val Lys Lys Tyr Pro Ile Asn
            1250                1255                1260

Leu Gly Gln Tyr Gln Asn Lys Val Val Tyr Ser Pro His Asp Tyr Gly
1265                1270                1275                1280

Pro Leu Val Tyr Gln Gln Pro Trp Phe Tyr Pro Gly Phe Thr Lys Asp
            1285                1290                1295

Thr Leu Tyr Asn Asp Cys Trp Arg Asp Asn Trp Thr Tyr Ile Met Asp
            1300                1305                1310
```

```
Asn Gly Ile Ala Pro Leu Leu Ile Gly Glu Trp Gly Gly Tyr Leu Asp
        1315                1320                1325

Gly Gly Asp Asn Glu Lys Trp Met Thr Tyr Leu Arg Asp Tyr Ile Ile
        1330                1335                1340

Glu Asn His Ile His His Thr Phe Trp Cys Tyr Asn Ala Asn Ser Gly
1345                1350                1355                1360

Asp Thr Gly Gly Leu Val Gly Tyr Asp Phe Ser Thr Trp Asp Glu Gln
            1365                1370                1375

Lys Tyr Asn Phe Leu Lys Pro Ala Leu Trp Gln Asp Ser Lys Gly Arg
        1380                1385                1390

Phe Val Gly Leu Asp His Lys Arg Pro Leu Gly Thr Asn Gly Lys Asn
        1395                1400                1405

Ile Asn Ile Thr Ile Tyr Tyr Gln Asn Gly Glu Lys Pro Pro Val Pro
        1410                1415                1420

Lys Asn
1425

(2) INFORMATION FOR SEQ ID NO: 44:

(i) SEQUENCE CHARACTERISTICS:
        (A) LENGTH: 1751 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 44:

Met Gln Glu Met Lys Ala Ile Lys Arg Val Val Ser Ile Thr Ala Leu
1                   5                   10                  15

Leu Val Leu Thr Leu Ser Leu Cys Phe Pro Gly Ile Met Pro Val Lys
                20                  25                  30

Ala Tyr Ala Gly Gly Thr Tyr Asn Tyr Gly Glu Ala Leu Gln Lys Thr
            35                  40                  45

Ile Met Phe Tyr Glu Phe Gln Met Ser Gly Lys Leu Pro Ser Trp Val
        50                  55                  60

Arg Asn Asn Trp Arg Gly Asp Ser Gly Leu Asp Asp Gly Lys Asp Val
65                  70                  75                  80

Gly Leu Asp Leu Thr Gly Gly Trp His Asp Ala Gly Asp His Val Lys
                85                  90                  95

Phe Asn Leu Pro Met Ser Tyr Ser Ala Ser Met Leu Gly Trp Ala Val
                100                 105                 110

Tyr Glu Tyr Lys Asp Ala Phe Val Lys Ser Lys Gln Leu Glu His Ile
            115                 120                 125

Leu Asn Gln Ile Glu Trp Ala Asn Asp Tyr Phe Val Lys Cys His Pro
        130                 135                 140

Ser Lys Tyr Val Tyr Tyr Gln Val Gly Asp Pro Thr Val Asp His
145                 150                 155                 160

Asn Phe Trp Gly Pro Ala Glu Val Met Gln Met Lys Arg Pro Ala Tyr
                165                 170                 175

Lys Cys Asp Leu Ser Asn Pro Ala Ser Ser Val Val Ala Glu Thr Ala
                180                 185                 190

Ala Ser Leu Ala Val Ala Ser Val Val Ile Lys Glu Arg Asn Ser Gln
            195                 200                 205

Lys Ala Ala Ser Tyr Leu Gln His Ala Lys Asp Leu Phe Glu Phe Ala
        210                 215                 220
```

-continued

```
Asp Thr Thr Arg Ser Asp Ala Gly Tyr Thr Ala Ala Thr Gly Phe Tyr
225                 230                 235                 240

Thr Ser Gly Gly Phe Ile Asp Asp Leu Gly Trp Ala Ala Val Trp Leu
            245                 250                 255

Tyr Ile Ala Thr Asn Asp Ser Ser Tyr Leu Thr Lys Ala Glu Glu Leu
            260                 265                 270

Met Ser Glu Tyr Ala Asn Gly Thr Asn Thr Trp Thr Gln Cys Trp Asp
            275                 280                 285

Asp Val Arg Tyr Gly Thr Leu Ile Met Leu Ala Lys Ile Thr Gly Lys
290                 295                 300

Glu Leu Tyr Lys Gly Ala Val Glu Arg Asn Leu Asp His Trp Thr Asp
305                 310                 315                 320

Arg Ile Thr Tyr Thr Pro Lys Gly Met Ala Tyr Leu Thr Gly Trp Gly
            325                 330                 335

Ser Leu Arg Tyr Ala Thr Thr Ala Ala Phe Leu Ala Cys Val Tyr Ala
            340                 345                 350

Asp Trp Ser Gly Cys Asp Ser Asn Lys Lys Thr Lys Tyr Leu Asn Phe
            355                 360                 365

Ala Lys Ser Gln Ile Asp Tyr Ala Leu Gly Ser Thr Gly Arg Ser Phe
370                 375                 380

Val Val Gly Phe Gly Thr Asn Tyr Pro Gln His Pro His His Arg Asn
385                 390                 395                 400

Ala His Ser Ser Trp Ala Asn Ser Met Lys Ile Pro Glu Tyr His Arg
            405                 410                 415

His Ile Leu Tyr Gly Ala Leu Val Gly Gly Pro Gly Ser Asp Asp Ser
            420                 425                 430

Tyr Asn Asp Asp Ile Thr Asp Tyr Val Gln Asn Glu Val Ala Cys Asp
            435                 440                 445

Tyr Asn Ala Gly Ile Val Gly Ala Leu Ala Lys Met Tyr Gln Leu Tyr
450                 455                 460

Gly Gly Glu Pro Ile Asp Asp Phe Lys Ala Ile Glu Thr Pro Thr Asn
465                 470                 475                 480

Asp Glu Ile Phe Val Glu Ser Lys Phe Gly Asn Ser Gln Gly Pro Asn
            485                 490                 495

Tyr Thr Glu Val Ile Ser Tyr Ile Tyr Asn Arg Thr Gly Trp Pro Pro
            500                 505                 510

Arg Val Thr Asp Lys Leu Ser Phe Lys Tyr Phe Ile Asp Leu Thr Glu
            515                 520                 525

Leu Ile Gln Ala Gly Tyr Ser Pro Asp Val Val Lys Val Asp Thr Tyr
530                 535                 540

Tyr Ile Glu Gly Gly Lys Ile Ser Gly Pro Tyr Val Trp Asp Lys Asn
545                 550                 555                 560

Arg Asn Ile Tyr Tyr Val Leu Val Asp Phe Ser Gly Thr Lys Ile Tyr
            565                 570                 575

Pro Gly Gly Glu Val Glu His Lys Lys Gln Ala Gln Phe Lys Ile Ser
            580                 585                 590

Val Pro Gln Gly Tyr Pro Trp Asp Pro Thr Asn Asp Pro Ser Tyr Lys
            595                 600                 605

Gly Leu Thr Ser Gln Leu Glu Lys Asn Lys Tyr Ile Ala Ala Tyr Asp
            610                 615                 620

Asn Asn Asn Leu Val Trp Gly Leu Glu Pro Gly Ala Ala Thr Ser Thr
625                 630                 635                 640

Pro Ala Pro Thr Ser Thr Pro Thr Pro Thr Pro Thr Pro Thr Pro Thr
```

-continued

```
                645                 650                 655
Val Thr Ala Thr Pro Thr Pro Thr Pro Thr Pro Thr Gly Ser
                660                 665                 670
Pro Gly Thr Gly Ser Gly Val Lys Val Leu Tyr Lys Asn Asn Glu Thr
                675                 680                 685
Ser Ala Ser Thr Gly Ser Ile Arg Pro Trp Phe Lys Ile Val Asn Gly
                690                 695                 700
Gly Ser Ser Ser Val Asp Leu Ser Arg Val Lys Ile Arg Tyr Trp Tyr
705                 710                 715                 720
Thr Val Asp Gly Asp Lys Pro Gln Ser Ala Val Cys Asp Trp Ala Gln
                        725                 730                 735
Ile Gly Ala Ser Asn Val Thr Phe Asn Phe Val Lys Leu Ser Ser Gly
                740                 745                 750
Val Ser Gly Ala Asp Tyr Tyr Leu Glu Val Gly Phe Ser Ser Gly Ala
                755                 760                 765
Gly Gln Leu Gln Pro Gly Lys Asp Thr Gly Asp Ile Gln Val Arg Phe
                770                 775                 780
Asn Lys Asn Asp Trp Ser Asn Tyr Asn Gln Ala Asp Asp Trp Ser Trp
785                 790                 795                 800
Leu Gln Ser Met Thr Asn Tyr Gly Glu Asn Ala Lys Val Thr Leu Tyr
                        805                 810                 815
Val Asp Gly Val Leu Val Trp Gly Gln Glu Pro Gly Gly Ala Thr Pro
                820                 825                 830
Ala Pro Thr Ser Thr Ala Thr Pro Thr Pro Thr Pro Thr Ala Thr Pro
                        835                 840                 845
Thr Pro Thr Pro Thr Pro Thr Pro Thr Pro Thr Val Ser Ala Thr Pro
                850                 855                 860
Thr Pro Ala Pro Thr Ala Ser Pro Val Gly Gly Ser Tyr Trp Thr Pro
865                 870                 875                 880
Ser Glu Ser Tyr Gly Ala Leu Lys Val Trp Tyr Ala Asn Gly Asn Leu
                        885                 890                 895
Ser Ser Pro Thr Asn Val Leu Asn Pro Lys Ile Lys Ile Glu Asn Val
                900                 905                 910
Gly Thr Thr Ala Val Asp Leu Ser Arg Val Lys Val Arg Tyr Trp Tyr
                        915                 920                 925
Thr Ile Asp Gly Glu Ala Thr Gln Ser Val Ser Val Ala Ser Ser Ile
930                 935                 940
Asn Pro Ala Tyr Ile Asp Val Lys Phe Val Lys Leu Gly Ala Asn Ala
945                 950                 955                 960
Gly Gly Ala Asp Tyr Tyr Val Glu Ile Gly Phe Lys Ser Gly Ala Gly
                        965                 970                 975
Val Leu Ala Ala Gly Gln Ser Thr Lys Glu Ile Arg Leu Ser Ile Gln
                980                 985                 990
Lys Gly Ser Gly Ser Tyr Asn Gln Ser Asn Asp Tyr Ser Val Arg Ser
                        995                 1000                1005
Ala Asn Ser Tyr Ile Glu Asn Glu Lys Val Thr Gly Tyr Ile Asp Asp
                1010                1015                1020
Val Leu Val Trp Gly Arg Glu Pro Gly Arg Asn Ala Gln Ile Lys Val
1025                1030                1035                1040
Trp Tyr Ala Asn Gly Asn Leu Gly Ser Met Thr Asn Val Leu Asn Pro
                        1045                1050                1055
Lys Ile Lys Ile Glu Asn Val Gly Thr Thr Ala Val Asp Leu Ser Arg
                1060                1065                1070
```

```
Val Lys Val Arg Tyr Trp Tyr Thr Ile Asp Gly Glu Ala Thr Gln Ser
        1075            1080            1085

Val Ser Val Thr Ser Ser Ile Asn Pro Ala Tyr Ile Asp Val Lys Phe
        1090            1095            1100

Val Lys Leu Gly Ala Asn Ala Gly Gly Ala Asp Tyr Tyr Val Glu Ile
1105            1110            1115            1120

Gly Phe Lys Ser Gly Ala Gly Val Leu Ala Ala Gly Gln Ser Thr Lys
                1125            1130            1135

Glu Ile Arg Leu Ser Ile Gln Lys Gly Ser Gly Ser Tyr Asn Gln Ser
        1140            1145            1150

Asn Asp Tyr Ser Val Arg Ser Ala Thr Gly Tyr Ile Glu Asn Glu Lys
        1155            1160            1165

Val Thr Gly Tyr Ile Asp Gly Ala Ile Val Trp Gly Arg Glu Pro Ser
        1170            1175            1180

Arg Gly Thr Lys Pro Ala Gly Gly Val Thr Pro Thr Pro Ala Pro Thr
1185            1190            1195            1200

Pro Thr Ser Thr Pro Thr Pro Thr Pro Thr Thr Thr Pro Thr Pro Thr
                1205            1210            1215

Pro Thr Val Thr Val Thr Pro Thr Pro Thr Pro Ala Val Thr Pro Asp
                1220            1225            1230

Val Lys Ile Ser Ile Asp Thr Ser Arg Gly Arg Thr Lys Ile Ser Pro
        1235            1240            1245

Tyr Ile Tyr Gly Ala Asn Gln Asp Ile Gln Gly Val Val His Pro Ala
        1250            1255            1260

Arg Arg Leu Gly Gly Asn Arg Leu Thr Gly Tyr Asn Trp Glu Asn Asn
1265            1270            1275            1280

Met Ser Asn Ala Gly Ser Asp Trp Tyr His Ser Ser Asp Asp Tyr Met
                1285            1290            1295

Cys Tyr Ile Met Gly Ile Thr Gly Asn Asp Lys Asn Val Pro Ala Ala
        1300            1305            1310

Val Val Ser Lys Phe His Glu Gln Ser Ile Lys Gln Asn Ala Tyr Ser
        1315            1320            1325

Ala Ile Thr Leu Gln Met Val Gly Tyr Val Ala Lys Asp Gly Asn Gly
        1330            1335            1340

Thr Val Ser Glu Ser Glu Thr Ala Pro Ser Pro Arg Trp Ala Glu Val
1345            1350            1355            1360

Lys Phe Lys Lys Asp Gly Ala Leu Ser Leu Gln Pro Asp Val Asn Asp
                1365            1370            1375

Asn Tyr Val Tyr Met Asp Glu Phe Ile Asn Tyr Leu Ile Asn Lys Tyr
        1380            1385            1390

Gly Arg Ser Ser Ser Ala Thr Gly Ile Lys Gly Tyr Ile Leu Asp Asn
        1395            1400            1405

Glu Pro Asp Leu Trp Phe Thr Thr His Pro Arg Ile His Pro Gln Lys
        1410            1415            1420

Val Thr Cys Ser Glu Leu Ile Asn Lys Ser Val Glu Leu Ala Lys Val
1425            1430            1435            1440

Ile Lys Thr Leu Asp Pro Asp Ala Glu Ile Phe Gly Pro Ala Ser Tyr
                1445            1450            1455

Gly Phe Val Gly Tyr Leu Thr Leu Gln Asp Ala Pro Asp Trp Asn Gln
                1460            1465            1470

Val Lys Gly Asn His Arg Trp Phe Leu Ser Trp Tyr Leu Glu Gln Met
        1475            1480            1485
```

```
Lys Lys Ala Ser Asp Ser Phe Gly Lys Arg Leu Leu Asp Val Leu Asp
    1490                1495                1500

Ile His Trp Tyr Pro Glu Ala Gln Val Gly Gly Val Arg Ile Cys Phe
1505                1510                1515                1520

Asp Gly Glu Asn Ser Thr Ser Arg Asp Val Ala Ile Ala Arg Met Gln
                1525                1530                1535

Ala Pro Arg Thr Leu Trp Asp Pro Thr Tyr Lys Thr Thr Gln Lys Gly
            1540                1545                1550

Gln Ile Thr Ala Gly Glu Asn Ser Trp Ile Asn Gln Trp Phe Pro Glu
        1555                1560                1565

Tyr Leu Pro Leu Leu Pro Asn Ile Lys Ala Asp Ile Asp Lys Tyr Tyr
    1570                1575                1580

Pro Gly Thr Lys Leu Ala Ile Thr Glu Phe Asp Tyr Gly Gly Lys Asp
1585                1590                1595                1600

His Ile Ser Gly Gly Ile Ala Leu Ala Asp Val Leu Gly Ile Phe Gly
                1605                1610                1615

Lys Tyr Gly Val Tyr Met Ala Ala Arg Trp Gly Asp Ser Gly Ser Tyr
            1620                1625                1630

Ala Gln Ala Ala Tyr Asn Ile Tyr Leu Asn Tyr Asp Gly Lys Gly Ser
        1635                1640                1645

Arg Tyr Gly Ser Thr Cys Val Ser Ala Glu Thr Thr Asp Val Glu Asn
    1650                1655                1660

Met Pro Val Tyr Ala Ser Ile Glu Gly Glu Asp Asp Ser Thr Val His
1665                1670                1675                1680

Ile Ile Leu Ile Asn Arg Asn Tyr Asp Arg Lys Leu Lys Ala Glu Ile
                1685                1690                1695

Lys Met Asn Asn Thr Arg Val Tyr Thr Gly Gly Glu Ile Tyr Gly Phe
            1700                1705                1710

Asp Ser Thr Ser Ser Gln Ile Arg Lys Met Gly Val Leu Ser Asn Ile
        1715                1720                1725

Gln Asn Asn Thr Ile Thr Ile Glu Val Pro Asn Leu Thr Val Tyr His
    1730                1735                1740

Ile Val Leu Thr Ser Ser Lys
1745                1750

(2) INFORMATION FOR SEQ ID NO: 45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 45:

GCGTGGTATG CAATATAC                                                    18

(2) INFORMATION FOR SEQ ID NO: 46:

(i) SEQUENCE CHARACTERISTICS:
        (A) LENGTH: 2029 base pairs
        (B) TYPE: nucleic acid
        (C) STRANDEDNESS: single
        (D) TOPOLOGY: linear (xi) SEQUENCE DESCRIPTION: SEQ ID NO: 46:

ATGGGAAGTG GTGTGAAGGT ACTGTACAAG AACAATGAGA CAAGTGCGAG CACAGGTTCT     60
```

-continued

| | | | | | |
|---|---|---|---|---|---|
| ATAAGGCCGT | GGTTTAAGAT | AGTGAATGGA | GGCAGCAGCA | GTGTTGATCT | TAGCAGGGTT | 120 |
| AAGATAAGAT | ACTGGTACAC | AGTGGATGGT | GACAAGCCAC | AGAGTGCGGT | ATGTGACTGG | 180 |
| GCACAGATAG | GGGCAAGCAA | TGTGACATTC | AATTTTGTGA | AGCTTAGCAG | CGGAGTGAGT | 240 |
| GGAGCGGATT | ATTACCTGGA | GGTAGGATTT | AGCAGTGGAG | CTGGGCAGTT | GCAGCCTGGT | 300 |
| AAGGACACAG | GGGATATACA | GGTAAGGTTT | AACAAGAATG | ACTGGAGCAA | TTACAATCAG | 360 |
| GCAGACGACT | GGTCATGGTT | GCAGAGCATG | ACGAATTATG | GAGAGAATGC | GAAGGTGACG | 420 |
| CTGTATGTAG | ATGGTGTTCT | GGTATGGGGG | CAGGAGCCGG | GAGGAGCGGT | GACCCCAACT | 480 |
| TCTACACCCA | CACCGGTTTC | ATCATCCACT | CCTACACCAA | CAGCAACGCC | AACACCTACA | 540 |
| CCTTCTATCA | CGATAACACC | AGCGCCAACT | GCAACACCCA | CTCCGACTCC | TTCTGTCACA | 600 |
| GATGATACAA | ATGATGATTG | GTTATTTGCG | CAGGGTAACA | AAATAGTCGA | CAAGGATGGC | 660 |
| AAACCTGTAT | GGTTAACAGG | AGTTAATTGG | TTTGGATTTA | ATACAGGAAC | GAATGTGTTT | 720 |
| GATGGTGTGT | GGAGTTGTAA | TCTTAAAAGT | GCATTAGCTG | AGATTGCAAA | CAGAGGATTT | 780 |
| AATTTGCTAA | GAGTACCGAT | TTCAGCAGAG | CTGATTTTGA | ATTGGTCGAA | AGGAATTTAT | 840 |
| CCAAAACCAA | ATATCAATTA | TTATGTTAAC | CCTGAGTTAG | AAGGTCTGAC | GAGTTTAGAG | 900 |
| GTATTTGATT | TTGTAGTAAA | AACATGCAAA | GAAGTTGGAC | TGAAAATTAT | GTTGGATATT | 960 |
| CATAGTGCAA | AAACTGATGC | GATGGGGCAT | ATATATCCGG | TATGGTATAC | AGATACTATA | 1020 |
| ACGCCAGAAG | ATTATTATAA | AGCATGTGAA | TGGATCACAG | AGAGATATAA | AAATGATGAT | 1080 |
| ACAATTGTAG | CATTTGATTT | GAAGAATGAG | CCACATGGTA | AACCATGGCA | AGATAGTGTT | 1140 |
| TTTGCAAAAT | GGGACAATTC | AACAGATATT | AACAACTGGA | AATATGCAGC | TGAGACCTGT | 1200 |
| GCGAAGAGAA | TACTTGCAAA | AAATCCAAAC | ATGTTAATAG | TAATTGAAGG | AATAGAAGCT | 1260 |
| TATCCAAAAG | ATGATGTTAC | GTGGACTTCT | AAATCATCAA | GTGACTATTA | TTCTACCTGG | 1320 |
| TGGGGCGGCA | ACTTACGGGG | TGTTAAAAAG | TATCCAATAA | ACCTTGGACA | GTATCAGAAC | 1380 |
| AAAGTGGTTT | ATTCACCACA | TGATTATGGA | CCATTGGTTT | ACCAGCAACC | CTGGTTTTAT | 1440 |
| CCTGGATTTA | CCAAAGATAC | GCTTTACAAT | GATTGCTGGA | GGGATAATTG | GACTTATATT | 1500 |
| ATGGATAATG | GGATAGCTCC | GTTGCTCATT | GGTGAATGGG | GTGGTTACTT | AGATGGTGGC | 1560 |
| GATAATGAAA | AGTGGATGAC | TTATTTGAGA | GATTATATTA | TAGAAAACCA | TATTCATCAT | 1620 |
| ACATTCTGGT | GTTACAATGC | AAATTCTGGT | GATACTGGAG | GATTGGTGGG | ATATGATTTT | 1680 |
| TCGACGTGGG | ATGAACAGAA | GTACAATTTC | TTAAAACCAG | CTTTATGGCA | GGATAGTAAA | 1740 |
| GGAAGATTTG | TTGGGCTTGA | TCACAAGAGA | CCACTGGGTA | CAAATGGGAA | GAATATAAAT | 1800 |
| ATAACTATTT | ATTACCAGAA | CGGTGAAAAA | CCGCCTGTCC | CAAAGAATTA | ATAAATGGAT | 1860 |
| CCGGCTGCTA | ACAAAGCCCG | AAAGGAAGCT | GAGTTGGCTG | CTGCCACCGC | TGAGCAATAA | 1920 |
| CTAGCATAAC | CCCTTGGGGC | CTCTAAACGG | GTCTTGAGGG | GTTTTTTGCT | GAAAGGAGGA | 1980 |
| ACTATATCCG | GATATCCACA | GGACGGGTGT | GGTCGCCATG | ATCGCGTAG | | 2029 |

(2) INFORMATION FOR SEQ ID NO: 47:

(i) SEQUENCE CHARACTERISTICS:
        (A) LENGTH: 616 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 47:

-continued

```
Met Gly Ser Gly Val Lys Val Leu Tyr Lys Asn Asn Glu Thr Ser Ala
 1               5                  10                  15

Ser Thr Gly Ser Ile Arg Pro Trp Phe Lys Ile Val Asn Gly Gly Ser
             20                  25                  30

Ser Ser Val Asp Leu Ser Arg Val Lys Ile Arg Tyr Trp Tyr Thr Val
             35                  40                  45

Asp Gly Asp Lys Pro Gln Ser Ala Val Cys Asp Trp Ala Gln Ile Gly
         50                  55                  60

Ala Ser Asn Val Thr Phe Asn Phe Val Lys Leu Ser Ser Gly Val Ser
 65                  70                  75                  80

Gly Ala Asp Tyr Tyr Leu Glu Val Gly Phe Ser Ser Gly Ala Gly Gln
                 85                  90                  95

Leu Gln Pro Gly Lys Asp Thr Gly Asp Ile Gln Val Arg Phe Asn Lys
             100                 105                 110

Asn Asp Trp Ser Asn Tyr Asn Gln Ala Asp Asp Trp Ser Trp Leu Gln
             115                 120                 125

Ser Met Thr Asn Tyr Gly Glu Asn Ala Lys Val Thr Leu Tyr Val Asp
         130                 135                 140

Gly Val Leu Val Trp Gly Gln Glu Pro Gly Gly Ala Val Thr Pro Thr
145                 150                 155                 160

Ser Thr Pro Thr Pro Val Ser Ser Thr Pro Thr Pro Thr Ala Thr
             165                 170                 175

Pro Thr Pro Thr Pro Ser Ile Thr Ile Thr Pro Ala Pro Thr Ala Thr
             180                 185                 190

Pro Thr Pro Thr Pro Ser Val Thr Asp Asp Thr Asn Asp Asp Trp Leu
             195                 200                 205

Phe Ala Gln Gly Asn Lys Ile Val Asp Lys Asp Gly Lys Pro Val Trp
         210                 215                 220

Leu Thr Gly Val Asn Trp Phe Gly Phe Asn Thr Gly Thr Asn Val Phe
225                 230                 235                 240

Asp Gly Val Trp Ser Cys Asn Leu Lys Ser Ala Leu Ala Glu Ile Ala
             245                 250                 255

Asn Arg Gly Phe Asn Leu Leu Arg Val Pro Ile Ser Ala Glu Leu Ile
             260                 265                 270

Leu Asn Trp Ser Lys Gly Ile Tyr Pro Lys Pro Asn Ile Asn Tyr Tyr
             275                 280                 285

Val Asn Pro Glu Leu Glu Gly Leu Thr Ser Leu Glu Val Phe Asp Phe
             290                 295                 300

Val Val Lys Thr Cys Lys Glu Val Gly Leu Lys Ile Met Leu Asp Ile
305                 310                 315                 320

His Ser Ala Lys Thr Asp Ala Met Gly His Ile Tyr Pro Val Trp Tyr
             325                 330                 335

Thr Asp Thr Ile Thr Pro Glu Asp Tyr Tyr Lys Ala Cys Glu Trp Ile
             340                 345                 350

Thr Glu Arg Tyr Lys Asn Asp Asp Thr Ile Val Ala Phe Asp Leu Lys
             355                 360                 365

Asn Glu Pro His Gly Lys Pro Trp Gln Asp Ser Val Phe Ala Lys Trp
             370                 375                 380

Asp Asn Ser Thr Asp Ile Asn Asn Trp Lys Tyr Ala Ala Glu Thr Cys
385                 390                 395                 400

Ala Lys Arg Ile Leu Ala Lys Asn Pro Asn Met Leu Ile Val Ile Glu
             405                 410                 415

Gly Ile Glu Ala Tyr Pro Lys Asp Asp Val Thr Trp Thr Ser Lys Ser
```

```
                      -continued 420               425               430

Ser Ser Asp Tyr Tyr Ser Thr Trp Trp Gly Gly Asn Leu Arg Gly Val
        435                 440                 445

Lys Lys Tyr Pro Ile Asn Leu Gly Gln Tyr Gln Asn Lys Val Val Tyr
    450                 455                 460

Ser Pro His Asp Tyr Gly Pro Leu Val Tyr Gln Gln Pro Trp Phe Tyr
465                 470                 475                 480

Pro Gly Phe Thr Lys Asp Thr Leu Tyr Asn Asp Cys Trp Arg Asp Asn
                485                 490                 495

Trp Thr Tyr Ile Met Asp Asn Gly Ile Ala Pro Leu Leu Ile Gly Glu
                500                 505                 510

Trp Gly Gly Tyr Leu Asp Gly Gly Asp Asn Glu Lys Trp Met Thr Tyr
            515                 520                 525

Leu Arg Asp Tyr Ile Ile Glu Asn His Ile His His Thr Phe Trp Cys
    530                 535                 540

Tyr Asn Ala Asn Ser Gly Asp Thr Gly Gly Leu Val Gly Tyr Asp Phe
545                 550                 555                 560

Ser Thr Trp Asp Glu Gln Lys Tyr Asn Phe Leu Lys Pro Ala Leu Trp
                565                 570                 575

Gln Asp Ser Lys Gly Arg Phe Val Gly Leu Asp His Lys Arg Pro Leu
            580                 585                 590

Gly Thr Asn Gly Lys Asn Ile Asn Ile Thr Ile Tyr Tyr Gln Asn Gly
        595                 600                 605

Glu Lys Pro Pro Val Pro Lys Asn
    610                 615

(2) INFORMATION FOR SEQ ID NO: 48:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: Other (xi) SEQUENCE DESCRIPTION: SEQ ID NO: 48:

Gln Lys Ala Ile Met Phe Tyr Glu Phe
1               5

(2) INFORMATION FOR SEQ ID NO: 49:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: Other (xi) SEQUENCE DESCRIPTION: SEQ ID NO: 49:

Asp Tyr Asn Ala Gly Phe Val Gly Ala Leu
1               5                   10
```